US006838574B1

(12) United States Patent
Endo

(10) Patent No.: US 6,838,574 B1
(45) Date of Patent: Jan. 4, 2005

(54) DICARBA-CLOSO-DODECARBORANE DERIVATIVES

(75) Inventor: Yasuyuki Endo, Kanagawa (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 0 days.

(21) Appl. No.: 09/868,934

(22) PCT Filed: Jan. 21, 2000

(86) PCT No.: PCT/JP00/00285

§ 371 (c)(1),
(2), (4) Date: Oct. 4, 2001

(87) PCT Pub. No.: WO00/43016

PCT Pub. Date: Jul. 27, 2000

(30) Foreign Application Priority Data

Jan. 22, 1999 (JP) ............................................. 11/014261
Sep. 30, 1999 (JP) ............................................. 11/280257

(51) Int. Cl.[7] ........................... C07C 69/76; A01N 37/10
(52) U.S. Cl. ............................ 560/56; 560/41; 560/102; 560/106; 562/473; 562/475; 562/491; 562/433; 562/455; 568/4; 514/569
(58) Field of Search ............................................. 560/103

(56) References Cited

U.S. PATENT DOCUMENTS 4,824,659 A    4/1989  Hawthorne

FOREIGN PATENT DOCUMENTS

| EP | 0205326 | 12/1986 |
|----|---------|---------|
| JP | 55154982 | 12/1980 |
| JP | 5-163296 | 6/1993 |

OTHER PUBLICATIONS

Fox, M.A. et al., "Transmission of electronic effects by icosahedal carboranes; skeletal carbon–13 chemical shifts and ultraviolet–visible spectra of substituted arly–p–carboranes (1,12–dicarba–closo–dodecaboranes)", J. Chem. Soc., Dalton Trans., No. 3, pp. 401–411 (1998).
Colquhoun H.M. et al., "Polyetherketones based on para–carborane: synthesis, sulfonation, and membrane–forming characteristics", Polymer, vol. 38, No. 17, pp. 4539–4546 (1997).
Prashar J.K. et al., "Synthesis of Carboranyl Phenylalanine for potential us in neutron capture therapy of melanoma", J. Chem. Soc. Perkin. Trans., No. 9, pp. 1051–1053 (1993).
Brown D.A. et al., "Polymers and ceramics based on icosa–hedral carbranes, model studies of the formation an dhydrolytic stability of aryl ether, ketone, amide, and borae linlakages between carborane units", J. Mater. Chem., vol. 2, No. 8, pp. 793–804 (1992).
Nemoto H. et al., "The first alkylation of o–carbonranes under essentially neutral conditions. Aplication to the synthesis of B carriers", J. Org. Chem., vol. 55, No. 25, pp. 6065–6066 (1990).

Chemical Abstracts, vol. 89, No. 196733.
Chemical Abstracts, vol. 89, No. 6351.
Matochkin V.S. et al., "Molecular mobility in polyarylates having difenylcarborane fragments in the chain", Faserforsch. Textiltech., Bol. 26, No. 6, pp. 261–265 (1975).
Chemical Abstracts, vol. 82, No. 17164.
Valetskii P.M. et al., "Polyamides of 1,7–bis (p–carbosyphenyl) carborane", Vysokomol. Soedin., Ser. A, vol. 15, No. 6, pp. 1227–1233 (1973).
Chemical Abstracts, vol. 76, No. 46645.
Chemical Abstracts, vol. 65, No. 98063.
Zakharkin L.I. et al., "Ionization constants of 1–(p–and m–carboxyphenyl)–2–substituted o–carboranes", Xh. Obshch. Khim., vol. 41, No. 6, pp. 1300–1303 (1971).
Chemical Abstracts, vol. 71, No. 39047.
Chemical Abstracts, vol. 68, No. 39684.
Zh. Obshch. Khim., vol. 41, pp. 1516–1520 (1971).
Chemical Abstracts, Vo. 75, No. 98063.
English Language Abstract of JP 5–163296, Jun. 29, 1997.
English Language Abstract of JP 55–154982, Feb. 12, 1980.
Endo Y. et al., "Structure–activity study of estrogenic agonists bearing dicarba–closo–dodecaborane. Effect of geometry and separation distance of hydroxyl groups at the ends of molecules", Bioorg. Med. Chem. Lett., vol. 9, No. 23, pp. 3313–3318 (1999).
Endo Y. et al., "Estrogenic antagonists bearing sicarba–closo–dodecaborane as a hydrophobic pharmacophore", Bioorg. Med. Chem. Lett., vol. 9, No. 24, pp. 3387–3392 (1999).
Endo Y. et al., "Potent estrogenic agonists bearing dicarba–closo–dodecaborane as a hydrophobic Pharmacophore", J. Med. Chem., vol. 42, No. 9, pp. 1501–1504 (1999).
Endo Y et al., "Dicarba–closo–dodecaboranes as pharmacophore. Novel potent retinoidal agonists", Cham. Pharm. Bull., vol. 47, No. 4, pp. 585–587 (1999).
Iijima T. et al., "Dicarba–closo–dodecaboranes as a pharma–cophore. Retinoidal antagonists and potential agonists", Chem. Pharm. Bull., vol. 47, No. 3, pp. 398–404 (1999).
Chemical Abstracts, vol. 66, No. 95101.
Chemical Abstracts, vol. 65, Par. No. 16989,f–g.
Chemical Abstracts, vol. 65, Par. No. 10604,g–h.
Chemical Abstracts, vol. 64, Par. No. 11235,d–h.
Chemical Abstracts, vol. 63, Par. No. 17865,f–h.

Primary Examiner—Paul J. Killos
(74) Attorney, Agent, or Firm—Greenblum & Bernstein, P.L.C.

(57) ABSTRACT

A medicament comprising as an active ingredient a compound or a physiologically acceptable salt thereof represented by general formula (I):

$$R^1-X-\underset{R^2}{\bigcirc}$$

wherein $R^1$ represents a dicarba-closo-dodecaboran-yl which may be substituted with a lower alkyl group, a lower alkenyl group, carboxyl group or the like; $R^2$ represents carboxyl group, a lower alkoxycarbonyl group, or hydroxyl group; and X represents a single bond or a linking group such as $-CO-Y^1-$ wherein $Y^1$ represents oxygen or $-N(R^3)-$ wherein $R^3$ represents hydrogen or a lower alkyl.

3 Claims, No Drawings

DICARBA-CLOSO-DODECARBORANE DERIVATIVES

TECHNICAL FIELD

The present invention relates to a novel dicarba-closo-dodecaborane derivative. The present invention also relates to a medicament comprising said dicarba-closo-dodecaborane derivative as an active ingredient.

BACKGROUND ART

Dicarba-closo-dodecaborane (hereinafter abbreviated as "carborane" in the specification) is an icosahedral cluster containing two carbon atoms and ten boron atoms in which both atoms are hexacordinated. In caboranes, depending on the position of the carbon atoms in the cluster, 3 kinds of isomers exist, i.e., 1,2-dicarba-closo-dodecarobane (ortho-carborane), 1,7-dicarba-closo-dodecaborane (meta-carborane), and 1,12-dicarba-closo-dodeca borane (paracarborane). These structures are unique among boron compounds, namely they are characterized to have very high thermal stability and hydrophobicity comparable to hydrocarbons.

A major utility of compounds composed of a carborane so far has been an application to $^{10}$Boron-Neutron Capture Therapy (BNCT). $^{10}$Boron-Neutron Capture Therapy has been developed as a therapy mainly to glioma and melanoma. When $^{10}$B atom is irradiated with thermal neutron (slow neutron), an α ray with 2.4 MeV energy is emitted and the atom is decomposed to $^7$Li and $^4$He. The range of α ray is about 10 μm which corresponds to a diameter of cells. Therefore, effects are expected that only cells in which $^{10}$B atoms are uptaken are destroyed and other cells are not damaged. For the development of BNCT, it is important how to have cancer cells selectively uptake $^{10}$B atoms in a concentration capable of destroying cells with neutron radiation. For that purpose, ortho-carborane skeleton has been utilized which has low toxicity and a high $^{10}$B atom content, and is easy to be synthesized. Moreover, nucleic acid precursors, amino acids, and porphyrins which contain ortho-carboranes have been synthesized and subjected to evaluation.

DISCLOSURE OF THE INVENTION

Studies on carborane compounds have been focused solely on creation of compounds suitable for BNCT, and therefore, for a purpose of introducing carboranes into cells, designs have been made in which carborane skeletons are attached to compounds with biological roles. However, the conventional studies are far from drug designs which utilizes properties of the carboranes per se for molecular recognition in vivo. An object of the present invention is to provide novel bioactive substances which utilize a carborane as a hydrophobic pharmacophore for a partial structure of a medicament on the basis of understanding of physical and chemical properties of carboranes.

Generally, hydrogen bonding and shape of molecule as well as hydrophobic interaction contribute to stabilization of a ligand-receptor complex. Accordingly, it is considered that introduction of a carborane as a hydrophobic moiety may increase the stability of a ligand-receptor complex and enhance a desirable biological activity. Carborane-containing nuclear receptor ligands provided by the present invention are promising compounds for application to BNCT from a viewpoint of targeting to cancer cells. As agents acting on nuclear receptors, they are expected to have pharmacodynamics different from that of conventional drugs while exhibiting superior activities.

An object of the present invention is to provide a bioactive compound having a carborane skeleton as a pharmacophore. More specifically, the object is to provide a novel compound which has a superior bioactivity and is useful as a regulating agent on a nuclear receptor with reduced cytotoxicity. Another object of the present invention is to provide a medicament comprising said compound as an active ingredient which is useful as an agent for differentiation-inducing therapy for leukemia and an estrogenic agent.

As a result of zealous endeavor of the inventors of the present invention to solve the foregoing objects, the inventors found that compounds having a dicarba-closo-dodecaborane structure represented by the following general formula (I) has superior activity as a ligand of a nuclear receptor such as the retinoic acid receptor and exhibits a superior therapeutic effect as a differentiation-inducing agent for the treatment of leukemia. The present invention was achieved on the basis of these findings.

The present invention thus provides a medicament which comprises as an active ingredient a compound or a physiologically acceptable salt thereof represented by the following general formula (I):

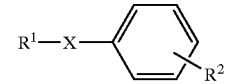

wherein $R_1$ represents a dicarba-closo-dodecaboran-yl group which may have one or more substituents selected from the group consisting of a lower alkyl group, a lower alkenyl group, carboxyl group, a lower alkoxycarbonyl group, amino group, hydroxyl group, a lower hydroxyalkyl group, a mono or di-lower alkylcarbamoyl-substitute alkyl group, a lower alkanoyl group, an aryl group which may be substituted, and a lower aralkyl group which may be substituted; $R^2$ represents carboxyl group, a lower alkoxycarbonyl group, or hydroxyl group; X represents a single bond, or a linking group selected from the group consisting of groups represented by the following formulas:

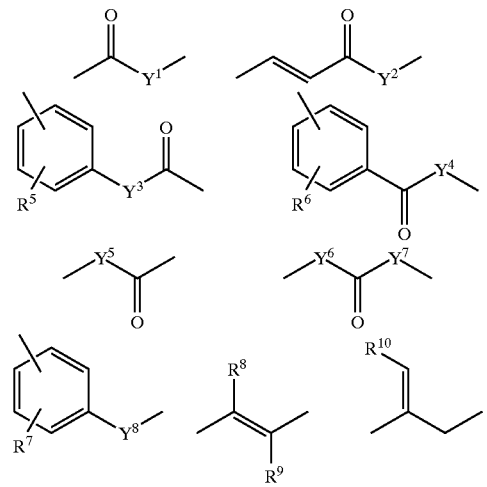

[wherein $Y^1$, $Y^2$, $Y^3$, $Y^4$, $Y^5$, $Y^6$, and $Y^7$ independently represent oxygen atom or —N($R^3$)— (wherein $R^3$ represents hydrogen atom or a lower alkyl group); $Y^8$ represents oxygen atom, —N($R^4$)— (wherein $R^4$ represents hydrogen atom or a lower alkyl group), —CO—, —CH$_2$—, or —C(=CH$^2$)—; R$^5$, R$^6$, and R$^7$ independently represent hydrogen atom or one or more substituents on the phenyl group; R$^8$ represents a lower alkyl group or an aryl group which may be substituted; R$^9$ represents a lower alkyl group; and R$^{10}$ represents an aryl group which may be substituted].

According to preferred embodiments of the aforementioned invention, provided are:

(1) a medicament comprising as an active ingredient the compound or a physiologically acceptable salt thereof represented by the aforementioned formula (I) wherein R$^1$ is a dicarba-closo-dodecaboran-yl group which may have a lower alkyl group, R$^2$ is carboxyl group or a lower alkoxycarbonyl group, and X is the aforementioned linking group; and (2) a medicament comprising as an active ingredient the compound or a physiologically acceptable salt thereof represented by the aforementioned formula (I) wherein R$^1$ represents a dicarba-closo-dodecaboran-yl group which may have a substituent selected from the group consisting of a lower alkyl group, a lower alkenyl group, carboxyl group, a lower alkoxycarbonyl group, amino group, hydroxyl group, a lower hydroxyalkyl group, a lower alkanoyl group, phenyl group which may be substituted, hydroxyphenyl group, and a lower alkoxyphenyl group, R$^2$ represents hydroxyl group, and X is a single bond.

The compound represented by the aforementioned formula (I) or a physiologically acceptable salt thereof can act as a ligand of a nuclear receptor. Therefore, the medicament is useful as an agent as a retinoid or an estrogenic agent, and also useful for therapeutic and/or prophylactic treatment of cancer, rheumatism, arteriosclerosis, diabetes, rejection reaction in case of an organ transplantation, and graft versus host disease. Particularly, the aforementioned medicament comprising the compound defined by (1) or a physiologically acceptable salt thereof can be used, for example, for therapeutic treatment of leukemia as an agent having retinoid action. The aforementioned medicament comprising the compound defined by (2) or a physiologically acceptable salt thereof is useful as an estrogenic agent, for example, for the prophylactic and/or therapeutic treatment of female hormone balance adjustment, menstrual disorders, osteoporosis, or cancer.

From another aspect, the present invention provides a use of the compound represented by the above formula (I) or a salt thereof for the manufacture of the aforementioned medicament; a method for therapeutic treatment of leukemia which comprises the step of administering to a patient a therapeutically effective amount of the compound represented by the aforementioned formula (I) or a physiologically acceptable salt thereof, preferably the compounds defined by the aforementioned (1) or a physiologically acceptable salt thereof; and a method for therapeutic and/or prophylactic treatment of a solid cancer or a serious dermatosis which comprises the step of administering to a patient a therapeutically effective amount of the compound represented by the aforementioned formula (I) or a physiologically acceptable salt thereof, preferably the compounds defined by the aforementioned (1) or a physiologically acceptable salt thereof.

From further aspect, the present invention provides, as a novel substance, the compound or a salt thereof represented by the following formula (I):

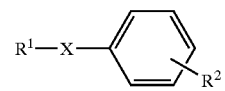

wherein R$^1$ represents dicarba-closo-dodecaboran-yl group which may have one or more substituents selected from the group consisting of a lower alkyl group, a lower alkenyl group, carboxyl group, a lower alkoxycarbonyl group, amino group, hydroxyl group, a lower hydroxyalkyl group, a mono or di-lower alkyl carbamoyl-substituted alkyl group, a lower alkanoyl group, an aryl group which may be substituted, and a lower aralkyl group which may be substituted; R$^2$ represents carboxyl group, a lower alkoxycarbonyl group, or hydroxyl group; X represents a single bond or a linking group selected from the group consisting of the groups represented by the following formulas;

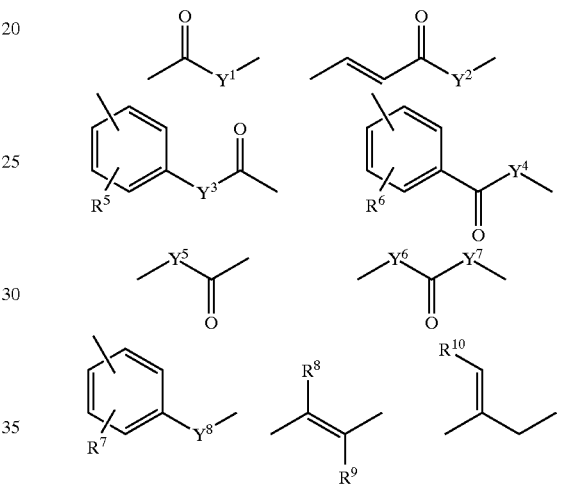

[wherein, Y$^1$, Y$^2$, Y$^3$, Y$^4$, Y$^5$, Y$^6$ and Y$^7$ independently represent oxygen atom or —N(R$^3$)— (wherein R$^3$ represents hydrogen atom or a lower alkyl group); Y$^8$ represents oxygen atom, —N(R$^4$)— (wherein R$^4$ represents hydrogen atom or a lower alkyl group), —CO—, —CH$^2$—, or —C(=CH$_2$)—; R$^5$, R$^6$, and R$^7$ independently represent hydrogen atom or one or more substituents on the phenyl group; R$^9$ represents a lower alkyl group or an aryl group which may be substituted; R$^9$ represents a lower alkyl group; and R$^{10}$ represents an aryl group which may be substituted], provided, when X is a single bond, the compound wherein R$^1$ is a non-substituted dicarba-closo-dodecaboran-yl group and R$^2$ is a hydroxyl group, and the compound wherein R$^1$ is a dicarba-closo-dodecaboran-yl group substituted with p-hydroxyphenyl group and R$^2$ is a hydroxyl group are excluded.

BEST MODE FOR CARRYING OUT THE INVENTION 1,2-Dicarba-closo-dodecaborane (ortho-carborane) is a compound shown on the upper part of the following formula. The compound has ten boron atoms expressed as "B" in the formula each having a hydrogen atom and two carbon atoms expressed as "C" in the formula each having a hydrogen atom. 1,2-Dicarba-closo-dodecaboran-1-yl group corresponds to a residual group formed by eliminating a hydrogen atom on one carbon atom in the carborane ring of the formula. As dicarba-closo-dodecaboranes, 1,7-dicarba-closo-dodecaboranes (meta-carborane) and 1,12-dicarbacloso-dode-caborane (para-carborane) are also known. These can form 1,7-dicarba-closo-dodecaboran-1-yl group and 1,12-dicarba-closo-dodecaboran-1-yl group similarly to the ortho-carborane. The term "dicarba-closo-dodecaboran-yl group" used herein encompasses residues of the three isomers of dicarba-closo-dodecaboranes. One carbon atom among the two carbon atoms constituting dicarba-closo-dodecaboran-1-yl group, which does not participate in the formation of the residue, and ten boron atoms can have a substituent independently. As an example, the lower part of the following formula indicates 1,12-dicarba-closo-dodecaborane (paracarborane) with methyl groups substituting on all of the ten boron atoms.

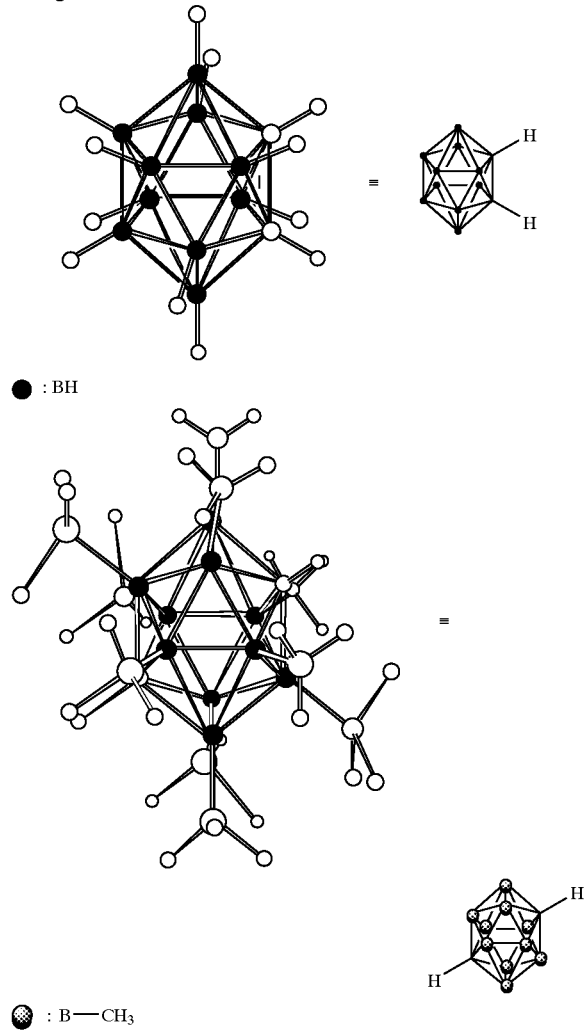

● : BH

◉ : B—CH$_3$

The medicament of the present invention are characterized to have a dicarba-closo-dodecaboran-yl group as a hydrophobic pharmacophore. A biopolymer molecule represented by a receptor, hereafter simply referred to as "receptor", has a characteristic structure as a partial structure which recognizes a drug, thereby forms stable bonds through spatial interaction with the drug and exhibits its bioaction. Plural functional groups or group composed thereof involved in the interaction are called "pharmacophore." A hydrophobic part of a drug stabilizes the bonds through hydrophobic interaction with the binding site of a receptor and has a significant role in recognition of a drug structure by a receptor.

The term "hydrophobic pharmacophore" in the compound of the present invention means a partial structure of a pharmaceutical compound and a structure which, as a hydrophobic moiety, has contribution or is expected to have contribution to bond stabilization with a receptor. The compound of the present invention has a dicarba-closo-dodecaboran-yl group as a hydrophobic pharmacophore and can be used as a medicament. Particularly, said compound can act as an agonist or an antagonist to a nuclear receptor to which a nuclear receptor ligand such as retinoid, estrogen, androgen or thyroid binds. Some compounds having a dicarba-closo-dodecaboran-yl group have been studied for application to BNCT. However, use of a dicarba-closo-dodecaboran-yl group as a hydrophobic pharmacophore, for a purpose of achieving binding stability with a receptor and enhancing bioactivity based on the binding stability, has not been reported.

In the specification, the lower alkyl or a lower alkyl moiety of a functional group that contains the lower alkyl moiety (e.g., the lower alkoxycarbonyl group, the lower alkenyl group, the lower hydroxyalkyl group, the lower alkanoyl group, the lower aralkyl group and the like) may be linear, branched, cyclic, or a combination thereof, and the number of carbon atom is from 1 to 6, preferably from 1 to 4. As the lower alkyl group, for example, methyl group, ethyl group, n-propyl group, isopropyl group; n-butyl group, sec-butyl group, isobutyl group, tert-butyl group can be used. As the lower alkenyl group, those having 1 to 6 carbon atoms can be used. The number of double bonds contained in the lower alkenyl group is not limited, and the number may generally be one to three, preferably one.

Substituents which can be present on a dicarba-closo-dodecaboran-yl group will be specifically explained. Methyl group and the like is preferred as the lower alkyl group. Examples of the lower alkoxy carbonyl group include methoxycarbonyl group, ethoxy carbonyl group and the like. The amino group may have one or two substituents, for example, a lower alkyl group and a lower alkanoyl group. When the amino group has two alkyl groups, they may bind to each other to form a ring. Examples of the lower hydroxyalkyl group include hydroxymethyl group, 2-hydroxyethyl group, 1-hydroxyethyl group, 3-hydroxypropyl group and the like. Examples of the lower alkanoyl group include acetyl group, propanoyl group and the like.

The number of carbon atoms of the alkyl group substituted with mono or di lower alkyl-substituted carbamoyl group is from 1 to 12, preferably about from 8 to 10, and two alkyl groups may bind to each other to form a ring. Phenyl group is preferable as the aryl group, and benzyl group is preferred as the aralkyl group. When the aryl group or the aralkyl group is substituted, the kind and the number of the substituents are not limited. For example, a lower alkyl group, a halogen atom, hydroxyl group, a lower alkoxy group and the like may be used as a substituent on the ring. A mono or di-lower alkyl-substituted amino group, or a cyclic amino group (e.g., pyrrolidinyl group, piperidinyl group and the like) may be a substituent on the lower alkoxy group on the ring of the aryl group or the aralkyl group. An example thereof includes 2-(N,N-dimethylamino) ethoxy group. The positions of substituents on the ring of the aryl group or the aralkyl group are not limited, and substituents may be in any of ortho, meta, or para position.

When the dicarba-closo-dodecaboran-yl group is substituted, the position of each substituent is not particularly limited. Some of or all of the carbon atoms and/or the boron atoms of the carborane ring may be substituted. For example, a substituent selected from the group consisting of a lower alkyl group, a lower alkenyl group, carboxyl group, a lower alkoxycarbonyl group, amino group, hydroxyl group, a lower hydroxy alkyl group, a mono or di-lower-alkylcarbamoyl substituted alkyl group, a lower alkanoyl group, an aryl group which may be substituted and a lower aralkyl group which may be substituted may preferably be present on the carbon atom(s) constituting the carborane ring. Furthermore, some or all of the boron atoms constituting the carborane ring may be substituted with, for example, an alkyl group or the like. Preferred examples include a carborane ring in which all of the boron atoms are alkylated, and a carborane ring in which only carbon atoms are substituted.

As the lower alkoxycarbonyl group represented by $R^2$, for example, ethoxy carbonyl group, methoxy carbonyl group and the like are preferred. $R^2$ may substitute in any position of the benzene ring, and preferably substitute in the para position. $Y^1$, $Y^2$, $Y^3$, $Y^4$, $Y^5$, $Y^6$ and $Y^7$ may preferred be a group represented by —N($R^8$)—, and as the lower alkyl group represented by $R^3$, the alkyl group specifically explained above can be suitably used. $R^3$ is preferably hydrogen atom or methyl group. When $Y^8$ is a group represented by —N($R^4$)—, $R^4$ is preferably hydrogen atom or methyl group. When $R^5$, $R^6$ and $R^7$ are substituents on the phenyl group, the kind, number, and position of the substituents are not particularly limited. Examples of the substituent on the phenyl group include, for example, a lower alkyl group, a lower alkoxy group, a lower alkoxycarbonyl group, a halogen atom, carboxyl group, amino group, an alkanoyl group, an aralkyl group, hydroxyl group, however, the substituents are not limited to these examples.

$R^5$, $R^6$ and $R^7$ are preferably hydrogen atoms. When $Y^8$ is —N($R^4$)— ($R^4$ represents a lower alkyl group, preferably methyl group), $R^7$ is preferably a lower alkyl group, for example, methyl group. As $R^8$, ethyl group or phenyl group having a substituent in the para position is preferred. When the phenyl group is substituted, an example of the substituent includes a lower alkoxy group substituted with mono or di-lower alkyl amino group where the two alkyl groups may bind to each other to form a ring, more specifically 2-(N, N-dimethylamino)ethoxy group. Ethyl group is preferred as $R^9$. As $R^{10}$, phenyl group having a substituent in the para position is preferred. An example of the substituent includes mono or di-lower alkylamino group where the two alkyl groups may bind to each other to form a ring, more specifically pyrrolidinomethyl group. When $R^1$ binds to the phenyl group in X, the binding position is not limited. Preferably, $R^1$ binds to the phenyl group in the meta or para position relative to the nitrogen atom or the carbonyl group present in X. When X is a single bond, $R^1$ binds directly to the phenyl group substituted with $R^2$. In such compounds, $R^2$ is preferably hydroxyl group.

More specifically, a preferred embodiment of the present invention includes (1) a compound of formula (I) wherein $R^1$ is dicarba-closo-dodecaboran-yl group which may have a lower alkyl group, $R^2$ is carboxyl group or a lower alkoxycarbonyl group, and X is the aforementioned linking group. In the aforementioned compound, each of $Y^1$, $Y^2$, $Y^3$, $Y^4$, $Y^5$, $Y^6$, and $Y^7$ is preferably a group represented by —N($R^3$)—, and $R^3$ is preferably hydrogen atom. Each of $R^4$, $R^5$ and $R^6$ is preferably hydrogen atom. When $Y^6$ is —N($R^3$)— (wherein $R^3$ is a lower alkyl group, preferably methyl group), $R^6$ is preferably a lower alkyl group, for example, methyl group.

Another preferred compound includes (2) a compounds of formula (I) wherein $R^1$ is dicarba-closo-dodecaboran-yl group which may have one or more substituents selected from the group consisting of a lower alkyl group, a lower alkenyl group, carboxyl group, a lower alkoxycarbonyl group, amino group, hydroxyl group, a lower hydroxyalkyl group, a lower alkanoyl group, phenyl group which may be substituted, hydroxyphenyl group, and a lower alkoxyphenyl group, $R^2$ is a hydroxyl group, and X is a single bond.

The compound represented by formula (I) may have one or more asymmetric carbon atoms. Any stereoisomers based on the asymmetric carbon atom(s) such as optically active isomers and diastereo isomers, any mixture of the stereo isomers, racemates and the like fall within the scope of the present invention. Furthermore, the compound represented by formula (I) may exist as an acid addition salt or a base addition salt, which also falling within the scope of the present invention. Examples of the acid addition salt include, for example, a mineral acid salt such as hydrochloride, sulfate, and nitrate, and an organic acid salt such as p-toluene sulfonate and maleate. Examples of the base addition salt include, for example, a metal salt such as sodium salt, potassium salt, and calcium salt, ammonium salt, and an organic amine salt such as triethylamine salt. In addition, an amino acid salt such as glycine salt as well as an internal salt (a zwitterion) fall within the scope of the present invention. Moreover, the compound or a salt thereof according to the present invention may form a hydrate or a solvate, and any of these substances fall within the scope of the present invention.

Preparations of typical compounds encompassed within formula (I) are shown in the following schemes. In addition, preparations of these compounds are also described in detail and specifically in the examples of the specification. Those ordinary skilled in the art can prepare any compounds falling within the scope of general formula (I) by referring to the preparations described in the following scheme and specific explanation in the examples, appropriately choosing starting materials, reaction conditions, reagents and the like, and optionally applying modifications or alterations thereto. In the formula (I), compounds wherein X is a single bond, $R^1$ is unsubstituted dicarba-closo-dodecaboran-yl group, and $R^2$ is a hydroxyl group (the compounds indicated as BE100, 200, and 300 in the following schemes; J. Chem. Soc. Dalton Trans., pp.401–411, 1998; Zh. Obshch. Khim., 41, pp.1516–20, 1971); and compound wherein X is a single bond, $R^1$ is 12-(4-hydroxyphenyl)-1,12-dicarba-closo-dodecaboran-yl group, and $R^2$ is a hydroxyl group (the compound indicated as BE160; J. Chem. Soc. Dalton Trans., pp.401–411, 1998) can be prepared by the methods described in the literature.

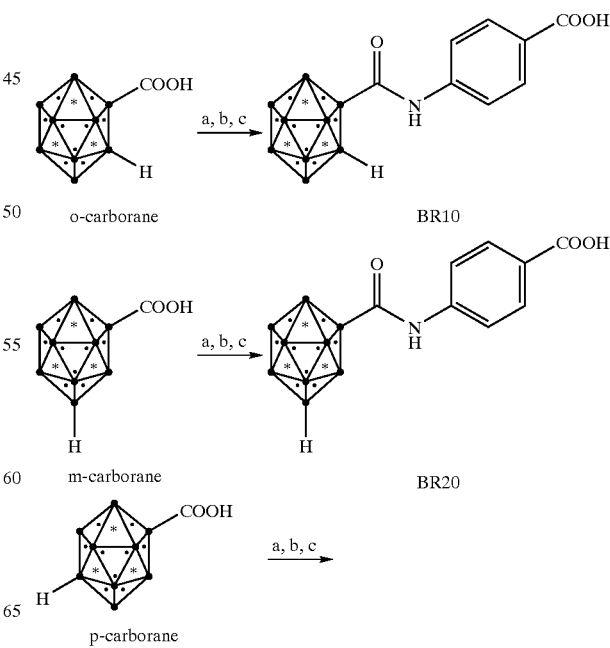

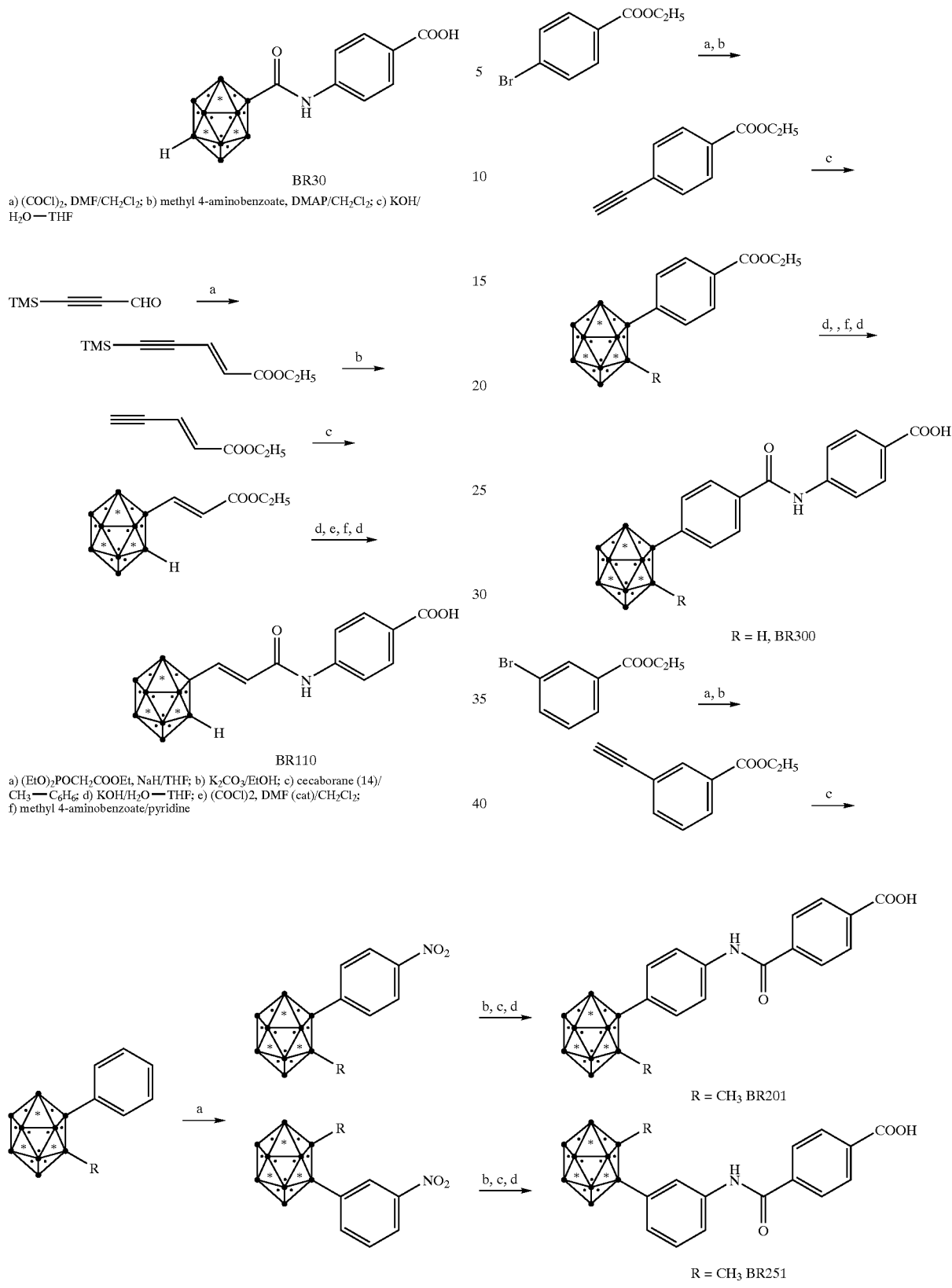

11
-continued
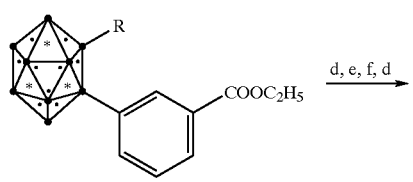
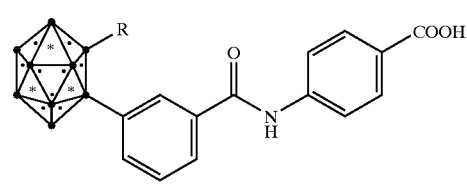
R = H, BR300
a) ethynyltrimethylsilane, (PPh₃)₂PdCl₂, CuI, iPrNH, THF;
b) K₂CO₃/EtOH; c) decaborane (14)/CH₃CN—C₆H₆;
d) KOH/H₂O—THF; e) (COCl)₂, DMF (cat)/CH₂Cl₂;
f) methyl 4-aminobenzoate/pyridine
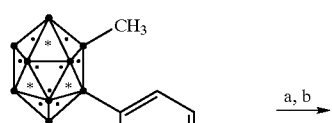
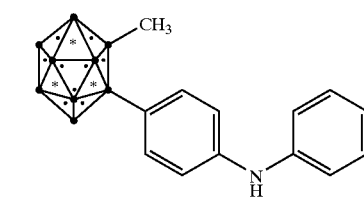
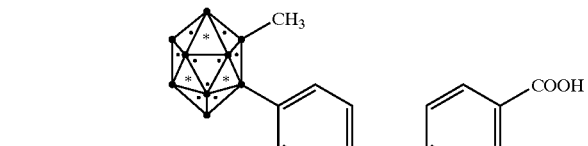
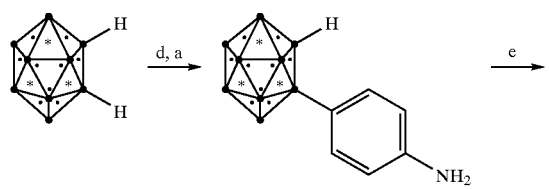
BR401
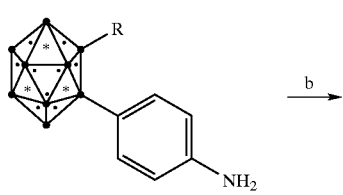
12
-continued
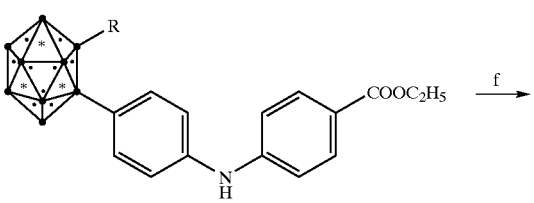
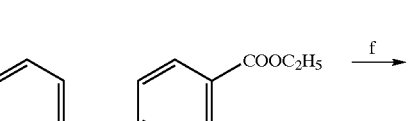
R = CH₂CH₂CH₃, BR403
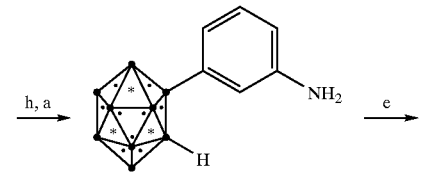
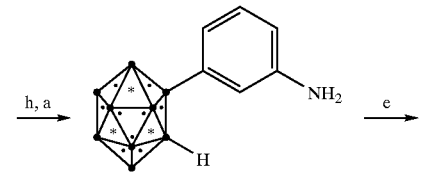
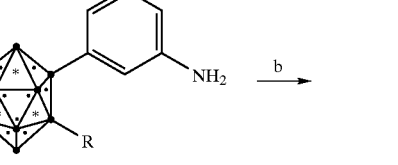
BR431
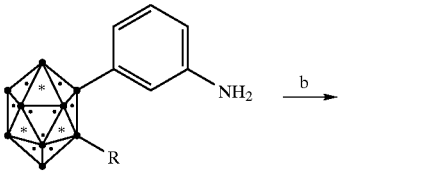
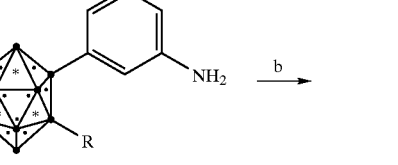
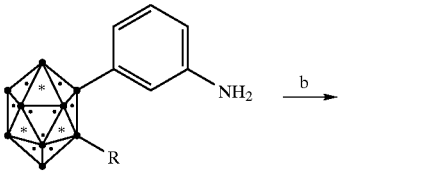
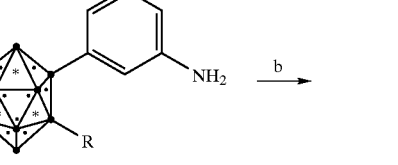

13
-continued
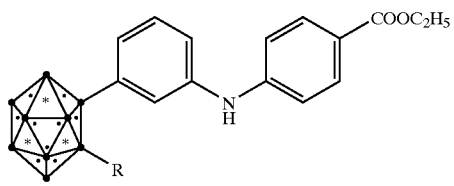
14
-continued
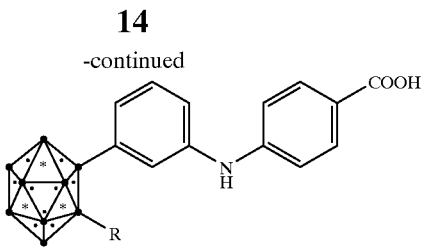
R = CH₂CH₂CH₃, BR453
a) H₂, Pd—C/EtOH; c) ethyl p-iodobenzoate, Cs₂CO₃, Pd₂(dba)₃, BINAP/toluene; c) KOH/H₂O—THF; d) 1) n-BuLi, CuCl/DME, 2) 4-nitroiodobenzen/pyridin; e) NaH, R—I/DMF; f) ; g) NaH, CH₃I/DMF; h) 1) n-BuLi, CuCl/DME, 2) 3-nitroiodobenzene/pyridine
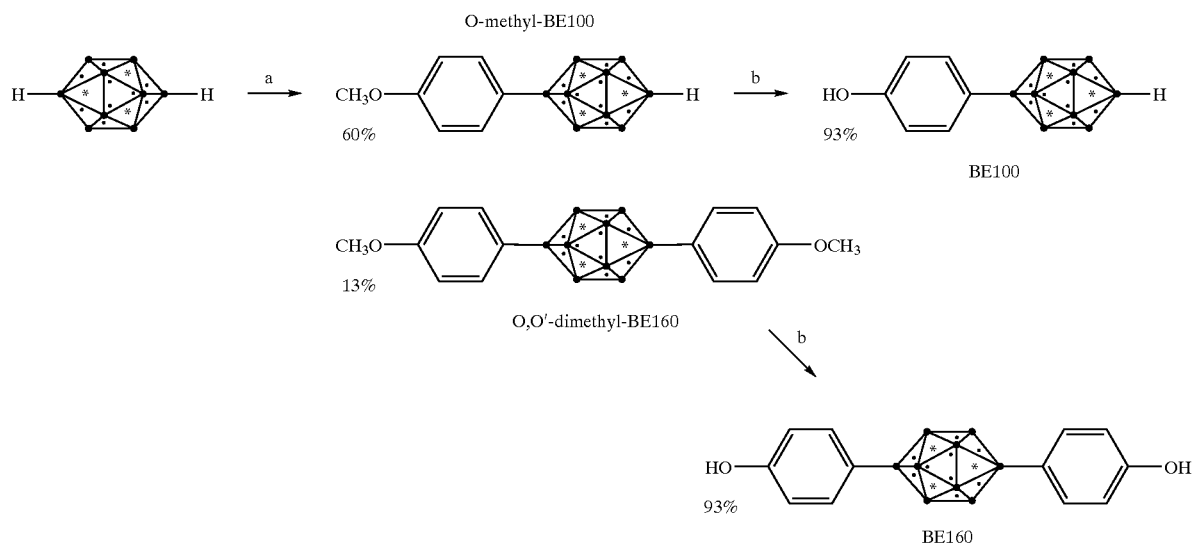
a) 1) n-BuLi, CuCl/DME 2) p-iodoanisole/pyridine, reflux b) BBr₃/CH₂Cl₂
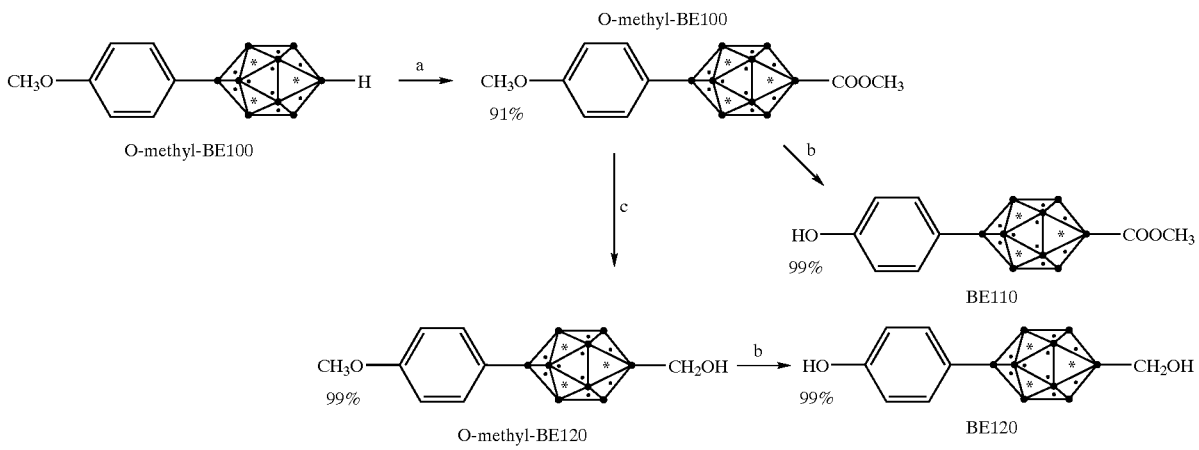
a) 1) n-BuLi/benzene-Et₂O 2) ClCOOCH₃ b) BBr₃/CH₂Cl₂ c) LiAlH₄/THF

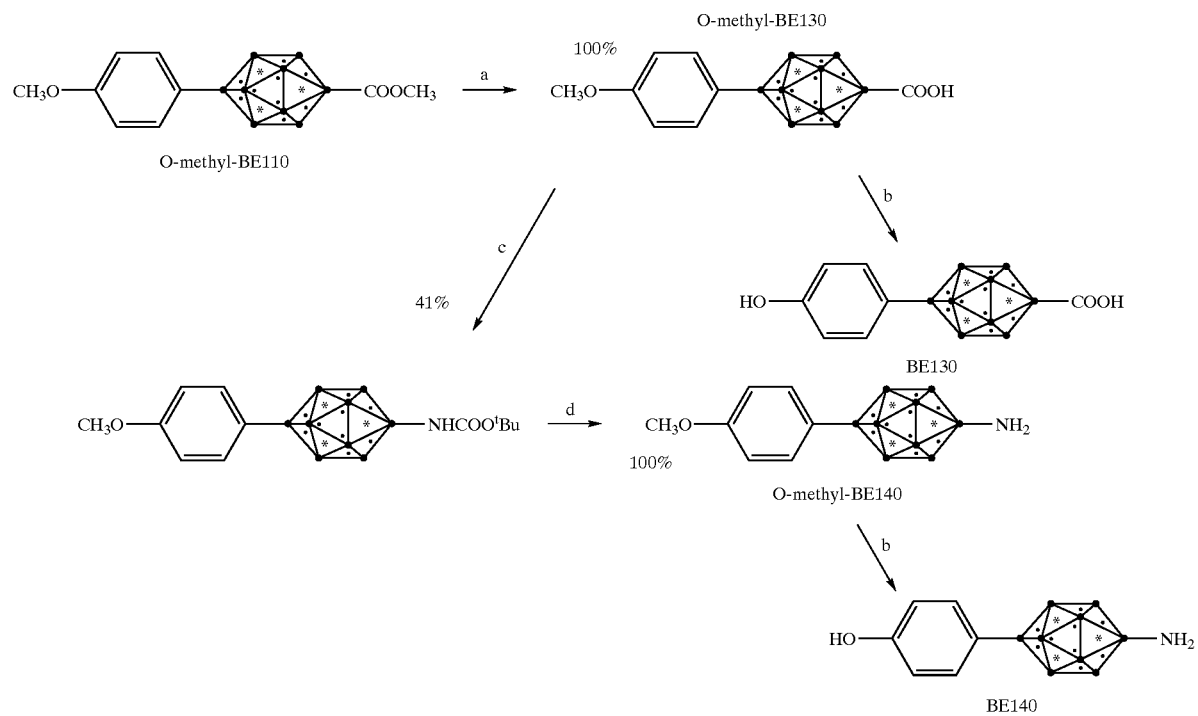
a) KOH/H₂O—THF b) BBr₃/CH₂Cl₂ c) DPPA, Et₃N, DMAP/t-BuOH reflux d) CF₃COOH/CH₂Cl₂
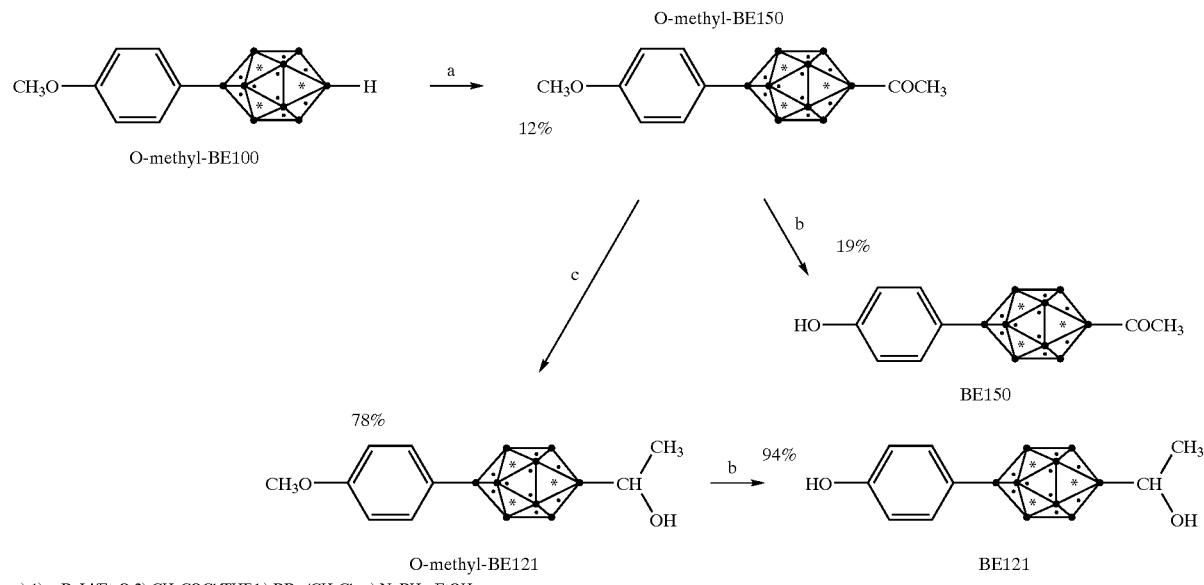
a) 1) n-BuLi/Et₂O 2) CH₃COCl/THF b) BBr₃/CH₂Cl₂ c) NaBH₄, EtOH
-continued
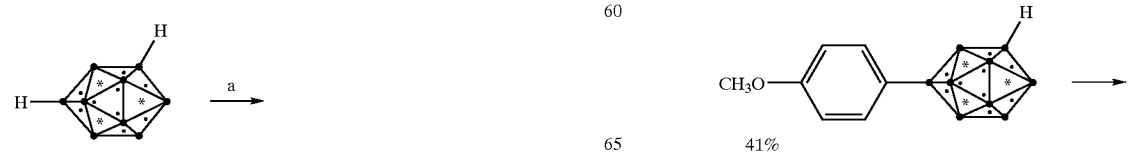

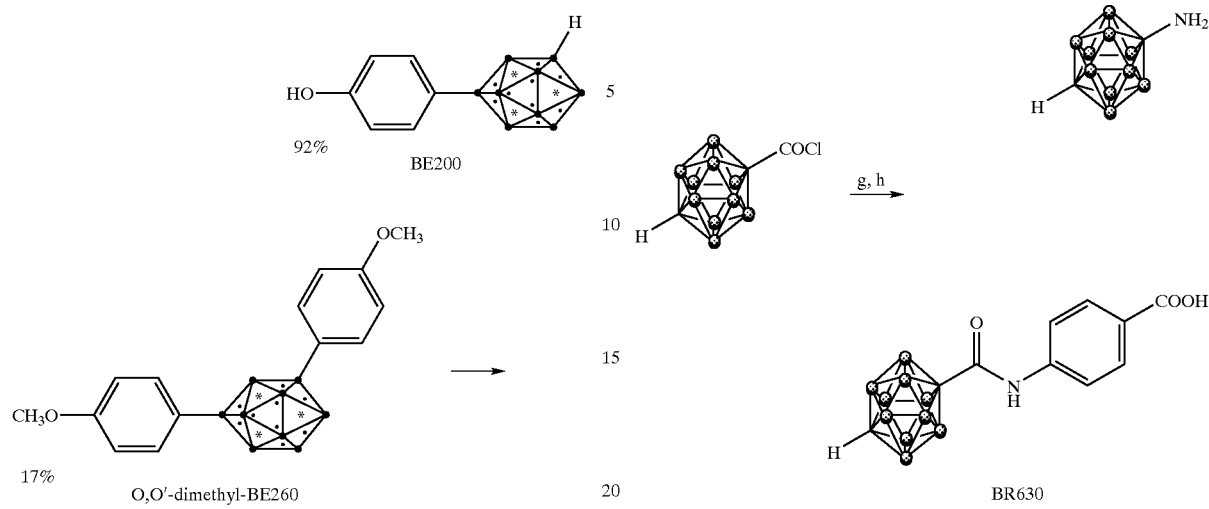
a) 1) n-BuLi, CuCl/DME 2) p-iodoanisol/pyridine, reflux b) BBr₃/CH₂Cl₂
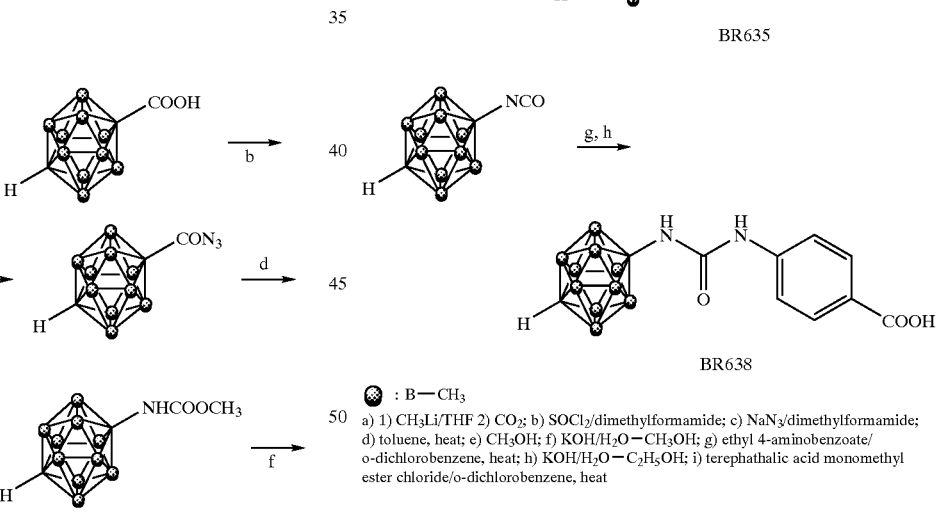
⊗ : B—CH₃
a) 1) CH₃Li/THF 2) CO₂; b) SOCl₂/dimethylformamide; c) NaN₃/dimethylformamide; d) toluene, heat; e) CH₃OH; f) KOH/H₂O—CH₃OH; g) ethyl 4-aminobenzoate/o-dichlorobenzene, heat; h) KOH/H₂O—C₂H₅OH; i) terephathalic acid monomethyl ester chloride/o-dichlorobenzene, heat
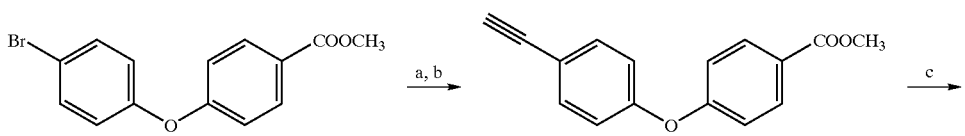

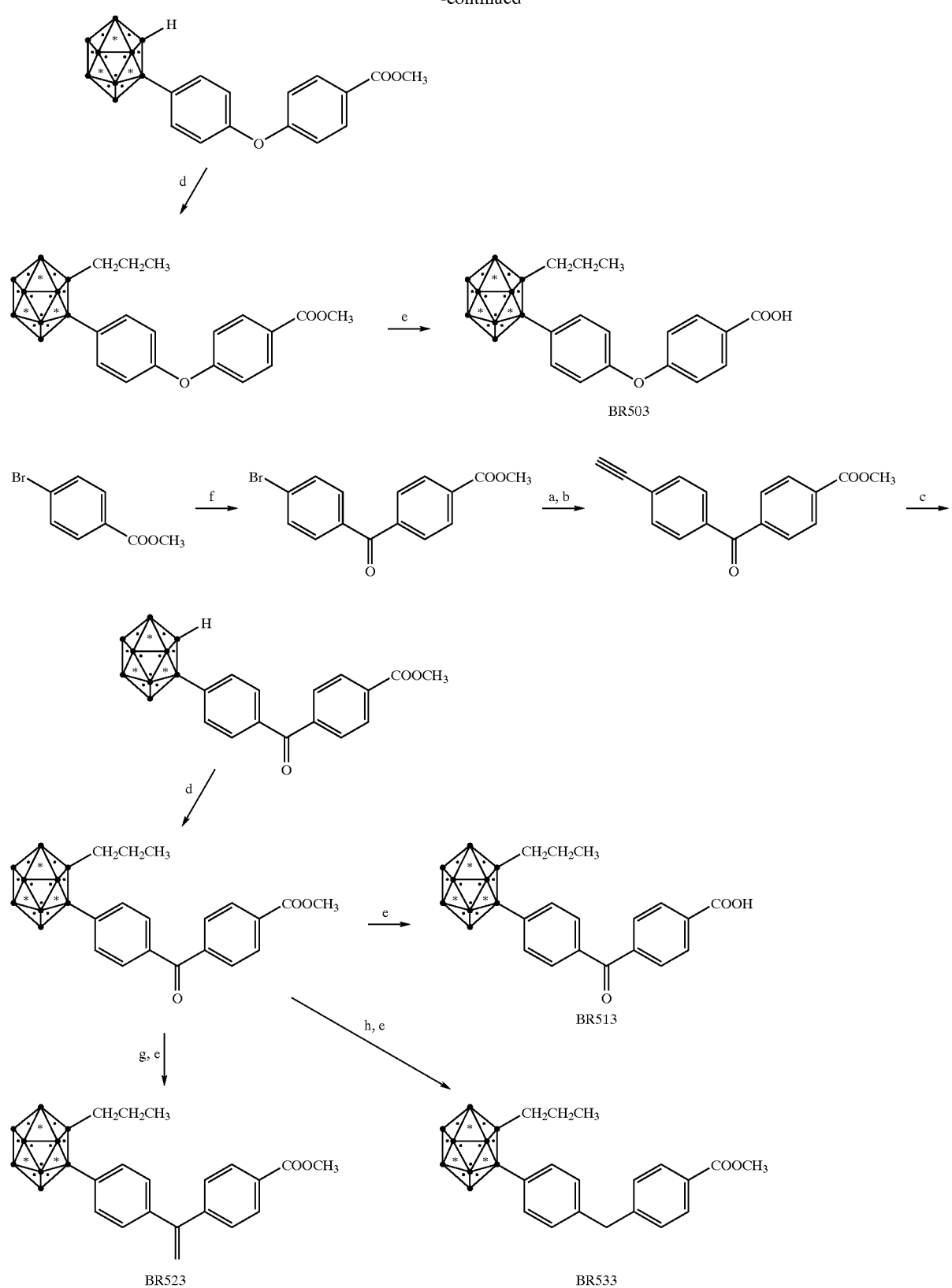
a) thynyltrimehylsilane, (PPh$_3$)$_2$PdCl$_2$, CuI, iPrNH, THF; b) K$_2$CO$_3$/CH$_3$OH; c) decaborane (14)/
CH$_3$CN—C$_8$H$_6$; d) NaH, R—I (CH$_3$I or n-CH$_3$CH$_2$CH$_2$I)/DMF; f) n-BuLi/THF; e) H$_2$SO$_4$/dioxane-H$_2$O;
g) [(C$_6$H$_5$)$_3$PCH$_3$]$^+$Br$^-$, NaNH$_2$/THF; h) (C$_2$H$_5$)$_3$SiH/CF$_3$COOH—CH$_2$Cl$_2$

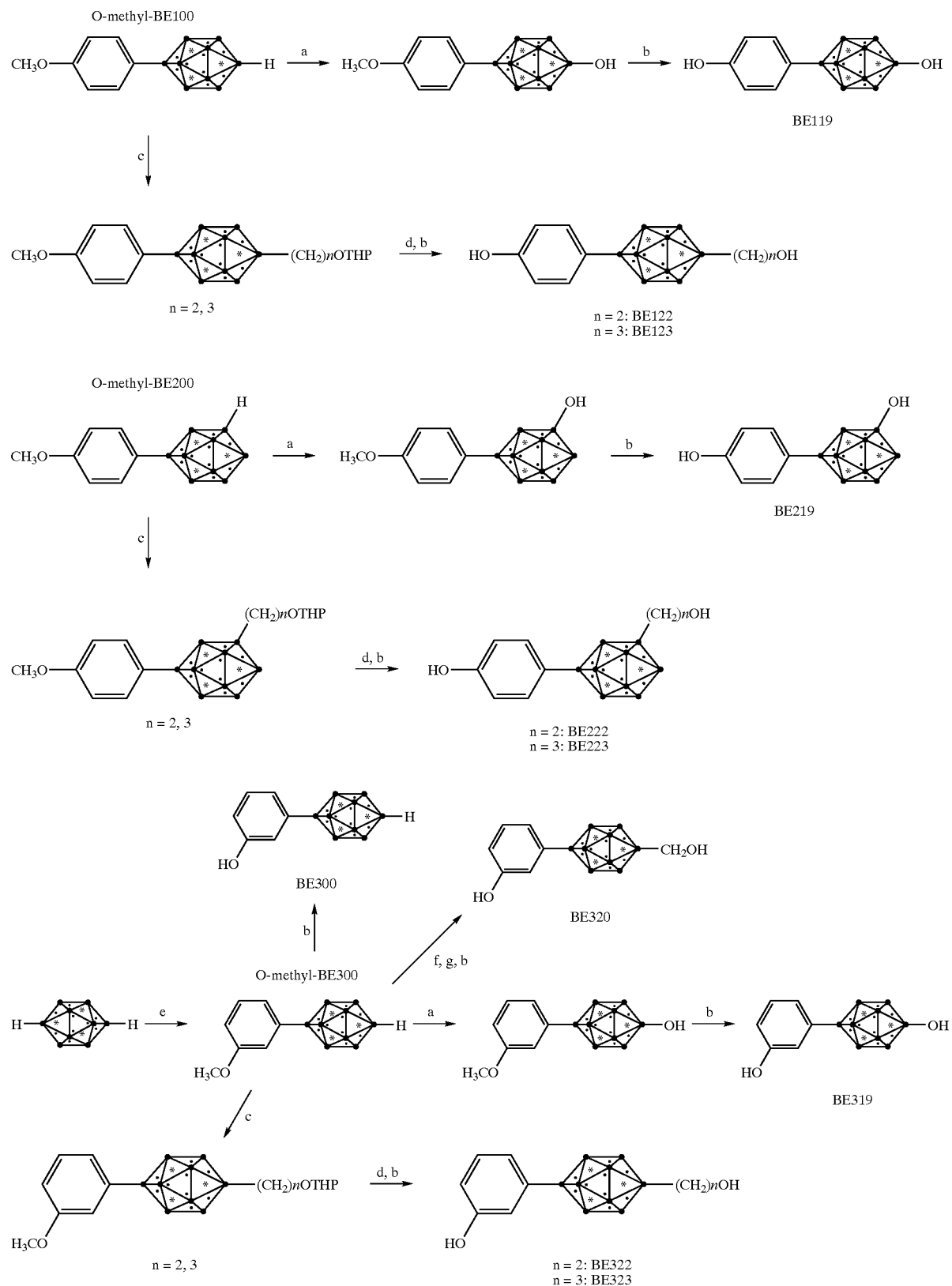
a) n-BuLi, (C$_6$H$_5$COO)$_2$/benzene-Et$_2$O; b) BBr$_3$/CH$_2$Cl$_2$; c) 1) n-BuLi, / benzene-Et$_2$O
2) Br(CH$_2$)$_n$OTHP; d) p-TsOH•H$_2$O/CH$_3$OH; e) 1) n-BuLi, CuCl/DME 2) 3-iodoanisole/pyridine;
f) n-BuLi, / benzene-Et$_2$O 2) ClCOOCH$_3$; g) LiAlH$_4$/THF

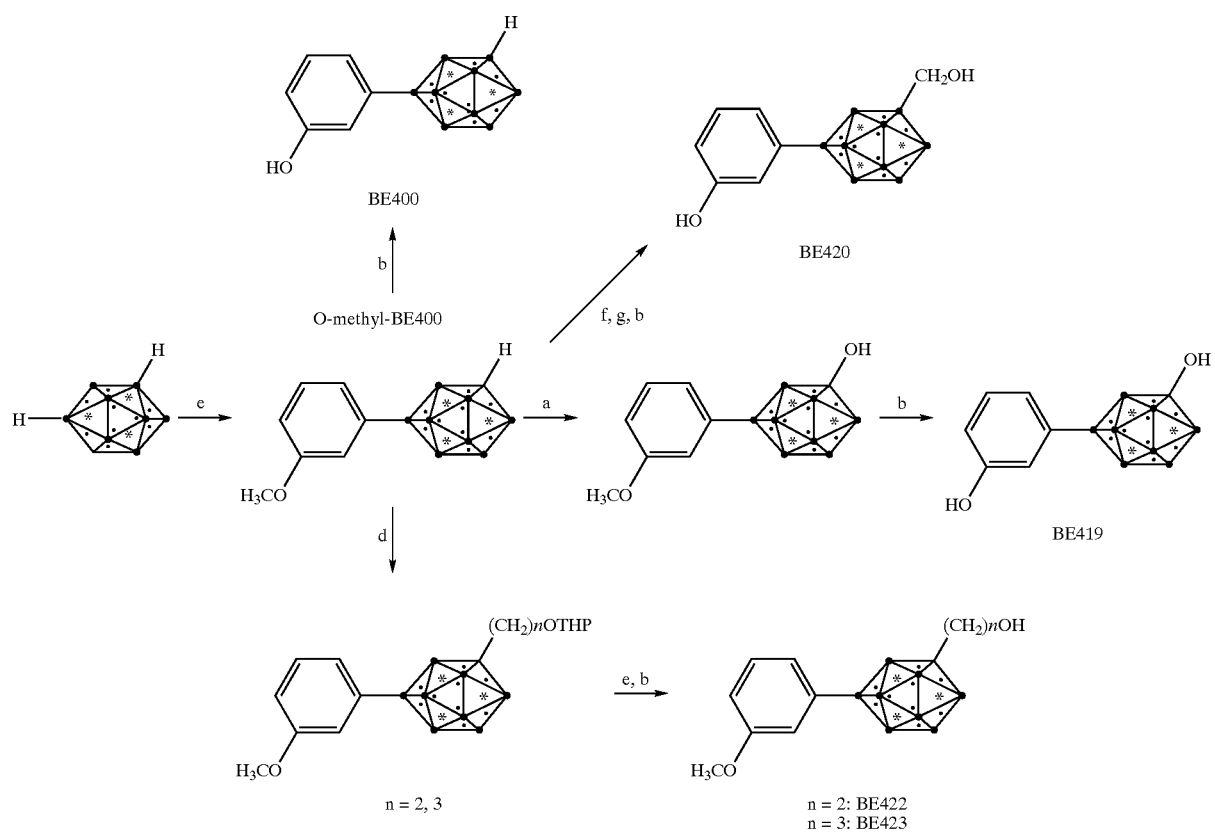
a) n-BuLi, (C₆H₅COO)₂/benzene-Et₂O; b) BBr₃/CH₂Cl₂; c) 1) n-BuLi, / benzene-Et₂O
2) Br(CH₂)ₙOTHP; d) p-TsOH·H₂O/CH₃OH; e) 1) n-BuLi, CuCl/DME 2) 3-iodoanisole/pyridine
f) n-BuLi, / benzene-Et₂O 2) ClCOOCH₃; g) LiAlH₄/THF
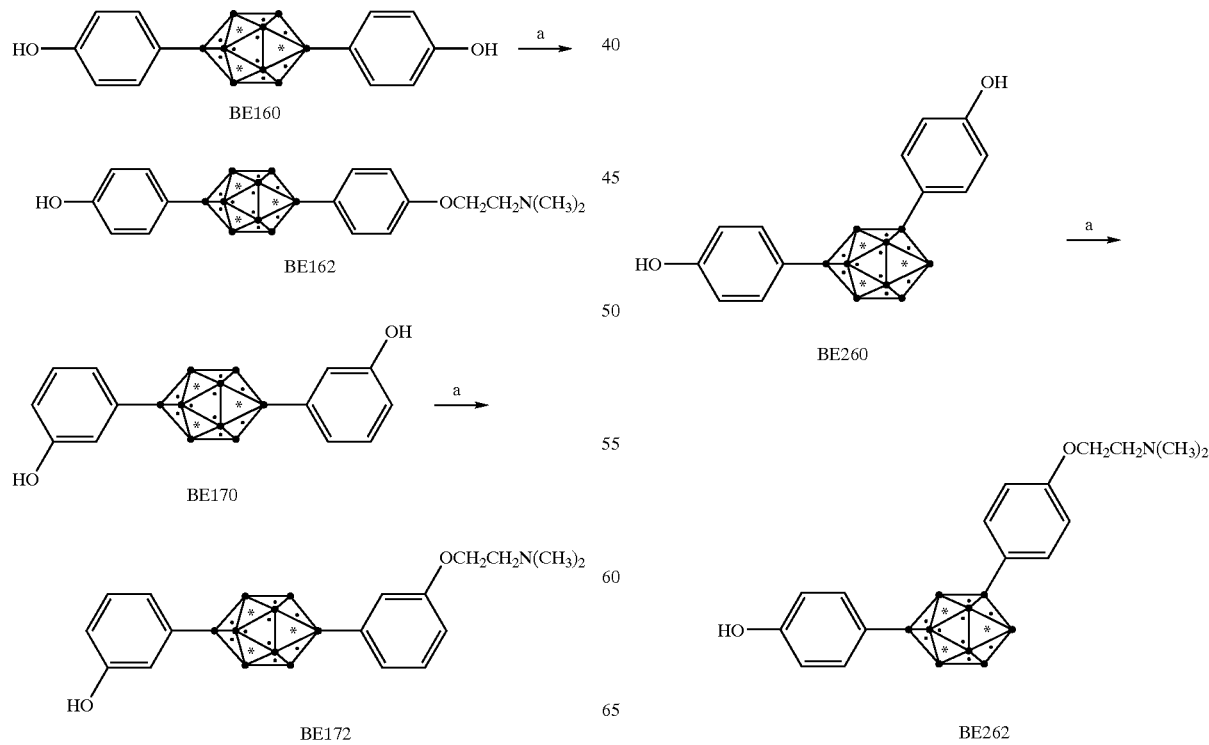

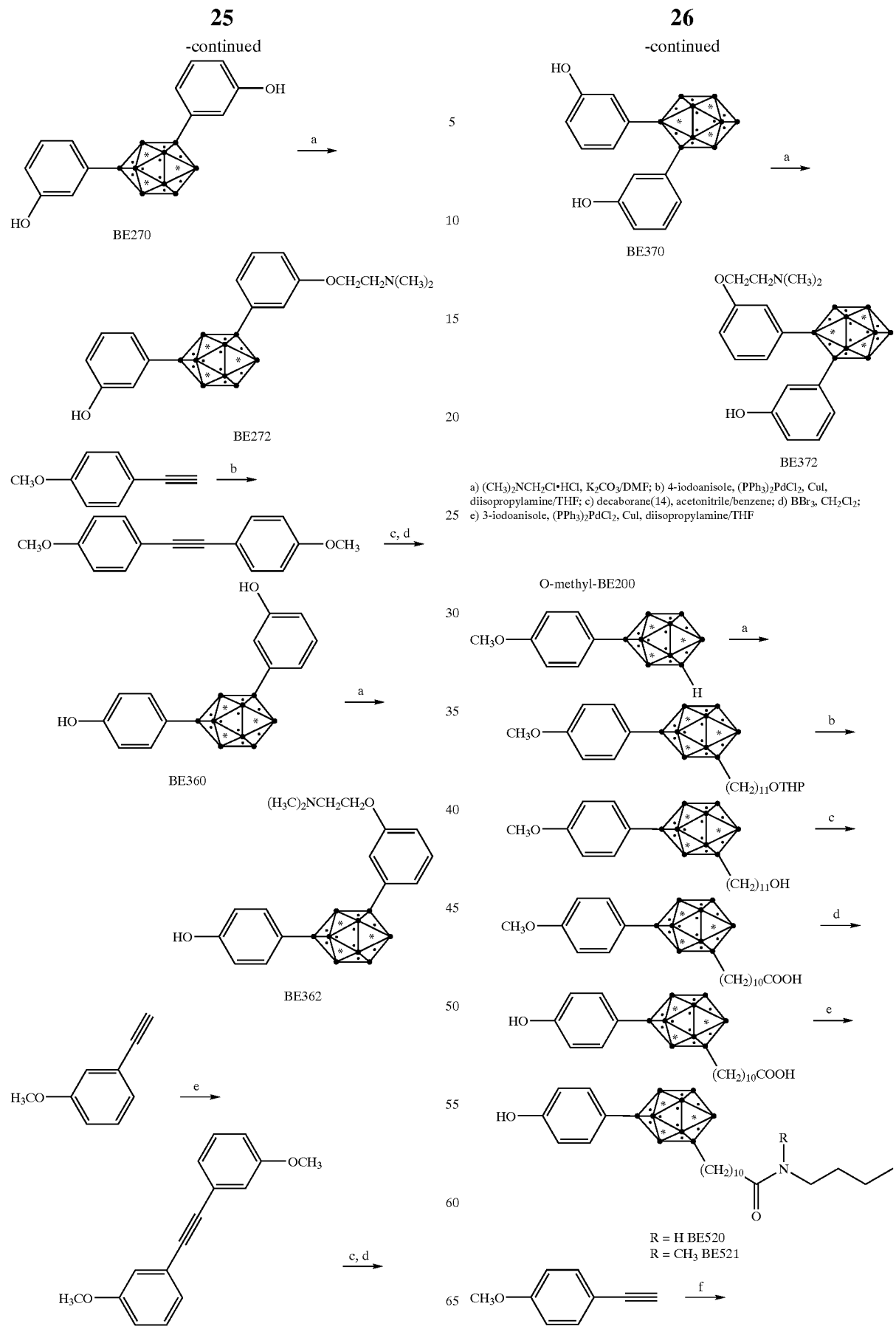
a) $(CH_3)_2NCH_2Cl \cdot HCl$, $K_2CO_3$/DMF; b) 4-iodoanisole, $(PPh_3)_2PdCl_2$, CuI, diisopropylamine/THF; c) decaborane(14), acetonitrile/benzene; d) $BBr_3$, $CH_2Cl_2$; e) 3-iodoanisole, $(PPh_3)_2PdCl_2$, CuI, diisopropylamine/THF -continued

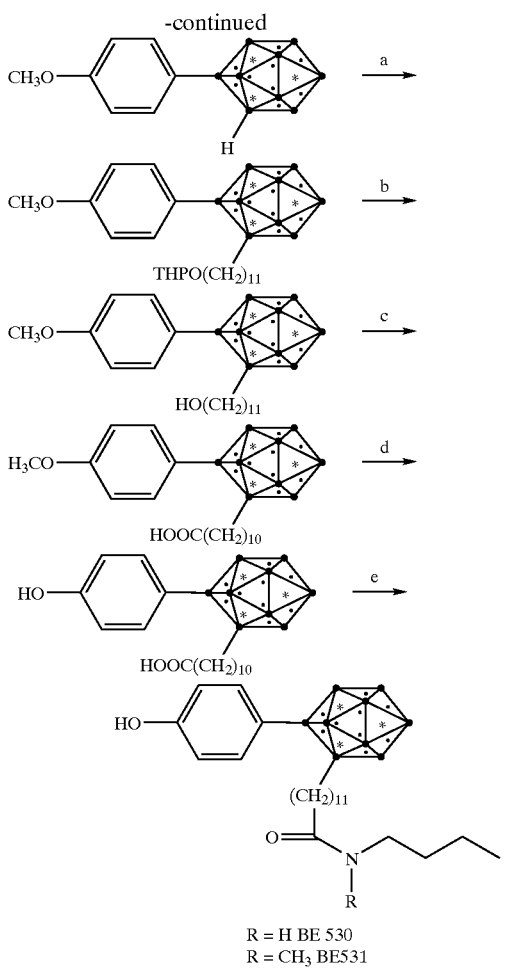

R = H BE 530
R = CH₃ BE531 a) 1) n-BuLi/DME 2) CuCl 3) 2-(11-bromo-n-undecanyloxy)tetrahydro-2H-pyrane, pyridine; b) p-toluenesulfonic acid/CH₃OH; c) CrO₃, 20% sulfuric acid/acetone; d) BBr₃/CH₂Cl₂; e) n-butylamine or N-n-butyl-N-methylamine, dicyclohexylcarbodiimide/acetonitrile; f) decaborane(14), acetonitrile/benzene The compounds represented by formula (I) have an action as a ligand of a nuclear receptor (a retinoic acid receptor) to specifically regulate transcriptional activation by the retinoic acid receptor. More specifically, the compounds have affinity to retinoic acid receptor RAR or retinoic acid receptor RXR, and can function as an agonist or an antagonist for these receptors. Some of the compounds have an action of enhancing activities of retinoic acid. On the basis of these functions, the compounds represented by formula (I) can prevent proliferation of leukemia cells and promote differentiation to normal cells. Therefore, the compounds are useful as a medicaments for therapeutic treatment of leukemia by differentiation inducing therapy, and also useful for therapeutic and/or preventive treatment of cancer, rheumatism, arteriosclerosis, diabetes, rejection reaction due to organ transplantation, and graft versus host disease. Moreover, they can be used as medicament for $^{10}$B-Neutron Capture Therapy based on targeting to cancer cells utilizing the affinity to the nuclear receptor. Furthermore, they can be used as estrogenic agents.

As the active ingredient of the medicament of the present invention, the compound represented by the aforementioned formula (I) or a physiologically acceptable salt thereof, a hydrate thereof or a solvate thereof can be used. As the medicament of the present invention, the aforementioned active ingredient, per se, may be administered. However, generally it is desirable that a pharmaceutical composition is formulated which comprises the aforementioned active ingredient and one or more pharmaceutical additives and then administered. The route of administration of the medicament of the present invention is not limited. The medicament can be administered orally or parenterally.

Examples of the pharmaceutical compositions suitable for oral administrations include tablets, capsules, powders, subtilized granules, granules, liquids, syrups and the like. Examples of the pharmaceutical compositions suitable for parenteral administrations include injections, drip infusions, suppositories, inhalants, eye drops, nasal drops, transdermally-adsorbable formulation, ointments, creams, patches and the like. Examples of pharmaceutical additives include excipients, disintegrators or disintegrating aids, binders, lubricants, coating agents, colorants, diluents, base materials, dissolving agents or solubilizers, isotonic agents, pH modifiers, stabilizers, propellants, adhesives and the like. Appropriate additives can be chosen and used depending on the type of the pharmaceutical composition. The doses of the medicament of the present invention are not particularly limited, and suitable doses can appropriately be chosen depending on the conditions such as the kind of the compound as an active ingredient, a purpose of preventive or therapeutic treatment, the type of a disease, the age and symptoms of a patient, the route of administration and the like.

EXAMPLES

The present invention will be more specifically explained by referring to the following examples. However, the scope of the present invention is not limited to these examples. The compound numbers in the examples correspond to those in the schemes shown above.

Example 1

1,2-dicarba-closo-dodecaborane-1-carboxylic acid (100 mg, 0.531 mmol) was dissolved in dichlorometbane (1 ml), and oxalyl chloride (101 mg, 0.795 mmol) and catalytic amount of dimethyl formamide (DMF, one drop) were added, and the mixture was stirred at room temperature for 3 h. Then the reaction mixture was concentrated. The residue and methyl 4-aminobenzoate (80.3 mg, 0.531 mmol) were suspended in dichloromethane (2 ml), 4-dimethylaminopyridine (130 mg, 1.06 mmol) was added at 0° C., stirred at room temperature for 1 h under argon atmosphere. The reaction was quenched by the addition of 2N hydrochloric acid, and the mixture was extracted with dichloromethane. The organic layer was washed with water, saturated sodium hydrogencarbonate solution, water, and brine in order, and dried over sodium sulfate and concentrated. The residue was purified by silica gel flash column chromatography (eluent: hexane/ethylacetate=5/1) to give methyl 4-[(1,2-dicarba-closo-dodecaboran-1-yl)carbamoyl]benzoate (58%).

$^1$H-NMR (CDCl₃) δ:1.50–3.50 (10H, m), 3.92 (3H, s), 4.35 (1H, br s), 7.55 (2H, d, J=8.8 Hz), 7.71 (1H, br s), 8.06 (2H, d, J=8.8 Hz).

4-[(1,2-dicarba-closo-dodecaboran-1-yl)carbamoyl] methyl benzoate (73 mg, 0.227 mmol) was dissolved in tetrahydrofuran (THF)(1 ml), 1N potassium hydroxide (0.91 ml) was added, and the mixture was stirred at room temperature for 16 h. The reaction was quenched by the addition of 2N hydrochloric acid, and the mixture was extracted with ethyl acetate. The organic layer was washed with water and brine, dried over sodium sulfate and concentrated. The reaction mixture was purified by silica gel flash column chromatography to give BR10 (60%).

BR10 : colorless needles (ethyl acetate/dichloromethane) m.p.: 249–251° C.

$^1$H-NMR (CDCl$_3$) δ:1.00–3.30 (10H, br m), 4.36 (1H, br s), 7.59 (2H, d, J=8.8 Hz), 7.75 (1H, br s), 8.12 (2H, d, J=8.8 Hz)

Anal. Calcd for C$_{10}$H$_{17}$B$_{10}$NO$_3$: C, 39.08; H, 5.57; N 4.56. Found C, 39.13; H, 5.58; N, 4.44.

BR20 was synthesized from 1,7-dicarba-closo-dodecaborane-1-carboxylic acid by the same method as preparation of BR10.

BR20: colorless needles (ethyl acetate/dichloromethane) m.p.: 271–273° C.; $^1$H-NMR (DMSO-d$_6$) δ:1.30–3.20 (10H, br m), 4.30 (1H, br s), 7.69 (2H, d, J=8.8 Hz), 7.89 (2H, d, J=8.8 Hz), 9.74 (1H, s), 12.87 (1H, br s).

HRMS Calcd for C$_{10}$H$_{17}$B$_{10}$NO$_3$ 307.2246, Found 307.2235

BR30 was synthesized from 1,12-dicarba-closo-dodecarorane-1-carboxylic acid by the same method as preparation of BR10.

BR30: Colorless needles (ethyl acetate/hexane); m.p.:>300° C.;

$^1$H-NMR (DMSO-d$_6$) δ:1.40–3.20 (10H, br m), 3.94 (1H, br s), 7.61 (2H, d, J=8.8 Hz), 7.86 (2H, d, J=8.8 Hz), 9.36 (1H, s), 12.80 (1H, br s).

Anal. Calc. for C$_{10}$H$_{17}$B$_{10}$NO$_3$: C, 39.08; H, 5.57; N, 4.56. Found C, 39.30; H, 5.54; N, 4.35.

Example 2

Ethynyltrimethylsilane (5.0 g, 50.9 mmol) was dissolved in dry diethyl ether (50 ml), 1.6 M n-butyllithium in hexane (35.0 ml, 56.0 mmol) was added dropwise at 0° C. under argon atmosphere. The mixture was stirred at the same temperature for 1 h. DMF(3.72 g, 50.9 mmol) was dissolved in diethyl ether (20 ml), and was added dropwise below 5° C. for 30 min, then the mixture was stirred at room temperature for 2 h. The reaction was quenched by the addition of 2N hydrochloric acid, and the mixture was extracted with diethyl ether. The organic layer was washed with water, saturated sodium hydrogencarbonate solution, and brine in order, and dried over sodium sulfate. Purification by distillation (40–45° C./15 mmHg) gave 3-(trimethylsilyl)propiol aldehyde (28%).

Colorless oil $^1$H-NMR (CDCl$_3$) δ:0.27 (9H, s), 9.17 (1H, s).

To a suspension of sodium hydride (556 mg, 13.9 mmol) in THF (7 ml), diethyl phosphonoethyl acetate (3.12 g, 13.9 mmol) in THF (7 ml) was added dropwise under argon atmosphere. The mixture was stirred at room temperature for 30 min, then 3-(trimethylsilyl) propiolaldehyde in THF(7 ml) was added dropwise at 0° C. The mixture was stirred at room temperature for 1.5 h, then poured into ice water, and extracted with ethyl acetate. The organic layer was washed with brine, dried over sodium sulfate, and concentrated. The residue was purified by silica gel flash column chromatography (eluent: hexane→hexane/ethyl acetate=50/1) to give ethyl 5-trimethylsilyl-(E)-2-penten-4-ynoate(65%).

Colorless oil $^1$H-NMR (CDCl$_3$) δ:0.21 (9H, s), 1.29 (3H, t, J=7.2 Hz), 4.21 (2H, q, J=7.2 Hz), 6.24 (1H, d, J=15.9 Hz), 6.74 (1H, d, J=15.9 Hz).

Potassium carbonate (563 mg, 4.07 mmol) was added to a solution of ethyl 5-trimethylsilyl-(E)-2-penten-4-ynoate (800 mg, 4.07 mmol) in ethanol (10 ml), and the mixture was stirred at room temperature for 1 h. The reaction was quenched by the addition of 2N hydrochloric acid, and the mixture was extracted with ethyl acetate. The organic layer was washed with water and brine, dried over sodium sulfate and concentrated. The residue was purified by silica gel flash column chromatography to give ethyl (E)-2-penten-4-ynoate (79%).

Colorless oily substance $^1$H-NMR (CDCl$_3$) δ:1.30 (3H, t, J=7.1 Hz), 3.34 (1H, dd, J=0.7, 2.4 Hz), 4.23 (2H, q, J=7.1 Hz), 6.32 (1H, dd, J=0.7, 15.9 Hz), 6.72 (1H, dd, J=2.4, 15.9 Hz).

A mixture of ethyl (E)-2-penten-4-ynoate(360 mg, 2.90 mmol) and decaborane (14) (532 mg, 4.35 mmol) in acetonitrile (1.5 ml) and benzene (15 ml) was refluxed for 17 h under argon atmosphere. After the mixture was concentrated, it was purified by silica gel flash column chromatography (eluent: hexane/ethyl acetate=10/1) to give 3-(1,2-dicarba-closo-dodecaboran-1-yl)-(E)-ethyl acrylate (64%).

Colorless prisms (hexane)

m.p.: 68–69° C.

$^1$H-NMR (CDCl$_3$) δ:1.30 (3H, t, J=7.1 Hz), 1.50–3.40 (10H, br m), 3.69 (1H, br s), 4.22 (2H, q, J=7.1 Hz), 6.20 (1H, d, J=15.4 Hz), 6.84 (1H, d, J=15.4 Hz)

Anal. Calcd for C$_7$H$_{18}$B$_{10}$O$_2$: C, 34.70; H, 7.49. Found C, 34.41; H, 7.66.

To a solution of 3-(1,2-dicarba-closo-dodecaboran-1-yl)-(E)-ethyl acrylate (220 mg, 0.908 mmol) in THF(5 ml), 1N potassium hydroxide (1.82 ml) was added, and the mixture was stirred at room temperature for 7 h. The reaction was quenched by the addition of 2N hydrochloric acid, and extracted with ethyl acetate. The organic layer was washed with brine, dried over sodium sulfate and concentrated. The residue was purified by silica gel flash column chromatography (eluent: chloroform/methanol=10/1) to give 3-(1,2-dicarba-closo-dodecaboran-1-yl)-(E)-propenoic acid (74%).

$^1$H-NMR (DMSO-d$_6$) δ:1.40–3.20 (10H, br m), 5.47 (1H, br s), 6.22 (1H, d, J=15.4 Hz), 6.92 (1H, d, 15.4 Hz), 13.00 (1H, br).

The propenoic acid (60 mg, 0.28 mmol) obtained above was dissolved in dichloromethane (1 ml), oxalyl chloride (53.3 mg, 0.42 mmol) and catalytic amount of DMF(one drop) were added. The mixture was stirred at room temperature for 1 h, and was concentrated. The residue was dissolved in pyridine (1 ml), and 4-amino methylbenzoate (46.6 mg, 0.308 mmol) was added. After stirring at room temperature for 18 h, the reaction was quenched by the addition of 2N hydrochloric acid, the mixture was extracted with ethyl acetate. The organic layer was washed with water, saturated sodium hydrogencarbonate solution, water, and brine in order, dried over sodium sulfate and concentrated. The residue was purified by silica gel flash column chromatography (eluent: hexane/ethyl acetate=5/1) to give methyl 4-[2-(1,2-dicarba-closo-decaborane-1-yl)-(E)-ethenylcarboxamine]benzoate (44%).

$^1$H-NMR (CDCl$_3$) δ:1.50–3.50 (10H, m), 3.72 (1H, br s), 3.91 (3H, s), 6.37 (1H, d, J=15.0 Hz), 6.96 (1H, d, J=15.0 Hz), 7.40 (1H, br s), 7.64 (2H, d, J=8.8 Hz), 8.04 (2H, d, J=8.8 Hz)

HRMS Calcd for C$_{13}$H$_{21}$B$_{10}$NO$_3$ 347.2524, Found 347.2534

The methyl benzoate (36 mg, 0.104 mmol) obtained above was dissolved in THF(1 ml), 1N potassium hydroxide (0.468 ml) was added, and stirred at room temperature for 36 h. The reaction was quenched by the addition of 2N hydrochloric acid, and the mixture was extracted with ethyl acetate. The organic layer was washed with water, and then with brine, dried over sodium sulfate and concentrated. The residue was purified by silica gel flash column chromatography (eluent: chloroform/methanol=50/1→5/1) to give 4-[2-(1,2-dicarba-closo-dododecaboran-1-yl)-(E)-ethenylcarboxamide]benzoic acid (BR110) (39%).

Colorless needles (ethyl acetate/hexane)

m.p.:>300° C.; $^1$H-NMR (CDCl$_3$) δ:1.40–3.20 (10H, br m), 5.50 (1H, br s), 6.67 (1H, d, J=15.1 Hz), 6.98 (1H, d, J=15.1 Hz), 7.73 (2H, d, J=8.8 Hz), 7.92 (2H, d, J=8.8 Hz), 10.62 (1H, s), 12.75 (1H, br)

HRMS Calcd for C$_{12}$H$_{19}$B$_{10}$NO$_3$ 338.2368, Found 333.2367

Example 3

A mixture of ethenylbenzene (5.51 g, 53.9 mmol) and decaborane (14)(2.64 g, 21.6 mmol) in acetonitrile (5.5 ml) and benzene (55 ml) was refluxed for 4 days under argon atmosphere. Then the mixture was concentrated, it was purified by silica gel column chromatography (eluent: hexane) to give 1-phenyl-1,2-dicarba-closo-dodecaborane (74%).

Colorless prisms (hexane)

m.p.: 66–67° C.

$^1$H-NMR (CDCl$_3$) δ:1.50–3.50 (10H, br m), 3.97 (1H, br s), 7.33 (2H, m), 7.39 (1H, m), 7.49 (2H, m).

1-Phenyl-1,2-dicarba-closo-dodecaborane(950 mg, 4.31 mmol) was dissolved in dry diethylether (15 ml), 1.54M n-butyl lithium in hexane solution(2.8 ml, 4.31 mmol) was added dropwise at 0° C. under argon atmosphere. After the mixture was stirred at room temperature for 3 h, it was cooled to −78° C. Methyl iodide (673 mg, 4.74 mmol) in THF(3 ml) was added dropwise, and further stirred at room temperature for 16 h. The reaction was quenched by the addition of 2N hydrochloric acid, and the mixture was extracted with diethylether. The organic layer was washed with water, and then with brine, dried over sodium sulfate and concentrated. The residue was purified by silica gel flash column chromatography(eluent: hexane) to give 1-methyl-2-phenyl-1,2-dicarba-closo-dodecaborane(94%).

Colorless prisms (hexane)

m.p.: 102–103° C.

$^1$H-NMR (CDCl$_3$) δ:1.50–3.50 (10H, br m), 1.69 (3H, s), 7.39 (2H, m), 7.45 (1H, m), 7.66 (2H, m)

HRMS Calcd for C$_9$H$_{18}$B$_{10}$ 234.2412, Found 234.2422

A solution of 1-methyl-2-phenyl-1,2-dicarba-closo-dodecaborane(900 mg, 3.84 mmol) in dichloromethane (17.5 ml) was added dropwise to a mixture of concentrated nitric acid and concentrated sulfuric acid (15:85, v/v, 17.5 ml) at 0° C., and stirred at room temperature for 4 h. The mixture was poured into ice water, and extracted with dichloromethane. The organic layer was washed with brine, dried over sodium sulfate and concentrated. The residue was purified by silica gel flash column chromatography (eluent: hexane/ethyl acetate=30/1) to give 4-(2-methyl-1,2-dicarba-closo-dodecaboran-1-yl)nitrobenzene(a)(34%) and 3-(2-methyl-1,2-dicarba-closo-dodecaboran-1-yl)nitrobenzene (b)(57%). colorless prisms (ethyl acetate/hexane)

m.p.: 105–106° C.

$^1$H-NMR (CDCl$_3$) δ:1.50–3.50 (10H, br m), 1.73 (3H, s), 7.87 (2H, d, J=9.0 Hz), 8.26 (2H, d, J=9.0 Hz)

HRMS Calcd for C$_9$H$_{17}$B$_{10}$NO$_2$ 279.2262, Found 279.2264

(b) colorless prisms (ethyl acetate/hexane)

m.p.: 126–127° C.

$^1$H-NMR (CDCl$_3$) δ:1.50–3.50 (10H, br m), 1.74 (3H, s), 7.64 (1H, t, J=8.1 Hz), 8.01 (1H, ddd, J=1.1, 2.0, 8.1 Hz), 8.34 (1H, ddd, J=1.1, 2.0, 8.1 Hz), 8.53 (1H, t, J=2.0 Hz)

HRMS Calcd for C$_9$H$_{17}$B$_{10}$NO$_2$ 279.2262, Found 279.2243

4-(2-Methyl-1,2-dicarba-closo-dodecaboran-1-yl) nitrobenzene (349 mg, 1.25 mmol) was dissolved in ethanol (25 ml), and was hydrogenated at room temperature for 1 h using 10% Pd/C(87 mg) under the atmospheric pressure of hydrogen. After removal of catalyst by filtration, the filtrate was concentrated to give 4-(2-methyl-1,2-dicarba-closo-dodecaboran-1-yl)aniline (95%).

$^1$H-NMR (CDCl$_3$) δ:1.40–3.50 (10H, br m), 1.68 (3H, s), 4.01 (2H, br), 6.62 (2H, d, J=8.6 Hz), 7.39 (2H, d, J=8.6 Hz).

The amine obtained above (100 mg, 0.401 mmol) was dissolved in pyridine (2.5 ml), terephthalic acid monomethyl ester chloride (119 mg, 0.599 mmol) was added at 0° C., and stirred at room temperature for 3 h. The reaction was quenched by the addition of 2N hydrochloric acid, and the mixture was extracted with ethyl acetate. The organic layer was washed with water, saturated sodium hydrogen carbonate solution, water, and brine in order, dried over sodium sulfate and concentrated. The residue was purified by silica gel flash column chromatography (eluent: dichloromethane/hexane=3/2→2/1) to give methyl 4-[4-(2-methyl-1,2-dicarba-closo-dodecaboran-1-yl)phenylcarbamoyl]benzoate (96%).

$^1$H-NMR (CDCl$_3$) δ:1.50–3.50 (10H, br m), 1.71 (3H, s), 3.97 (3H, s), 7.66 (2H, d, J=9.2 Hz), 7.70 (2H, d, J=9.2 Hz), 7.91 (1H, br s), 7.93 (2H, d, J=8.6 Hz), 8.18 (2H, d, J=8.6 Hz).

The methyl benzoate obtained above (140 mg, 0.34 mmol) was dissolved in THF (2 ml), 1N potassium hydroxide (0.68 ml) was added, and stirred at room temperature for 14 h. The reaction was quenched by the addition of 2N hydrochloric acid, and the mixture was extracted with ethyl acetate. The organic layer was washed with water and then brine, dried over sodium sulfate and concentrated. The residue was purified by silica gel flash column chromatography (eluent: chloroform/methanol=5/1) to give 4-[4-(2-methyl-1,2-dicarba-closo-dodecaboran-1-yl)-phenylcarbamoyl]benzoic acid (BR201)(98%).

Colorless needles (ethyl acetate/hexane)

m.p.:>300° C.

$^1$H-NMR (DMSO-d$_6$) δ:1.40–3.20 (10H, br m), 1.74 (3H, s), 7.71 (2H, d, J=8.8 Hz), 7.91 (2H, d, J=8.8 Hz), 8.04 (2H, d, J=8.6 Hz), 8.08 (2H, d, J=8.6 Hz), 10.66 (1H, s), 13.32 (1H, br)

Anal. Calcd for C$_{17}$H$_{23}$B$_{10}$NO$_3$: C, 51.37; H, 5.83; N, 3.52. Found C, 51.13; H, 5.68; N, 3.37.

3-(2-Methyl-1,2-dicarba-closo-dodecaboran-1-yl) nitrobenzene was converted to 4-[3-(2-methyl-1,2-dicarba-closo-dodecaboran-1-yl)phenylcarbamoyl]benzoic acid (BR251) employing the method described above.

Colorless needles (ethyl acetate/hexane)

m.p.: 284–286° C.

$^1$H-NMR (DMSO-d$_6$) δ:1.40–3.20 (10H, br m), 1.77 (3H, s), 7.45 (1H, br d, J=8.2 Hz), 7.49 (1H, t, J=8.2 Hz), 8.05 (1H, br d, J=8.2 Hz), 8.06 (2H, d, J=8.6 Hz), 8.09 (2H, d, J=8.6 Hz), 8.25 (1H, br s), 10.61 (1H, s), 13.30 (1H, br)

HRMS Calcd for C$_{17}$H$_{23}$B$_{10}$NO$_3$ 397.2681, Found 397.2683

Anal. Calcd for $C_{17}H_{23}B_{10}NO_3/0.2\ H_2O$: C, 50.91; H, 5.88; N, 3.49. Found C, 50.71; H, 5.97; N, 3.36.

Example 4

A mixture of ethyl 4-bromobenzoate (1.5 g, 6.55 mmol), ethynyl trimethylsilane (965 mg, 9.82 mmol), diisopropylamine (1.39 g, 13.7 mmol), cuprous iodide(25 mg, 0.131 mmol), and bis(triphenylphosphine) palladium(II) chloride (184 mg, 0.262 mmol) was heated at 45° C. for 4 h in dry THF (10 ml) under argon atmosphere. The reaction was quenched by the addition of water, and the mixture was extracted with ethyl acetate. The organic layer was washed with brine, dried over sodium sulfate and concentrated. The residue was purified by silica gel flash column chromatography (eluent: hexane/ethyl acetate=100/1) to give ethyl 4-[(trimethylsilyl)ethynyl]benzoate (73%).

$^1$H-NMR (CDCl$_3$) δ:0.26 (9H, s), 1.39 (3H, t, J=7.2 Hz), 4.37 (2H, q, J=7.2 Hz), 7.51 (2H, d, J=8.6 Hz), 7.97 (2H, d, J=8.6 Hz).

4-[(Trimethylsilyl)ethynyl]ethyl benzoate (1.15 g, 4.67 mmol) was dissolved in THF (10 ml), 1M tetrabutylammonium fluoride/THF solution (5.14 ml) was added dropwise at 0° C. After stirring at room temperature for 30 min, the reaction was quenched by the addition of water, and the mixture was extracted with ethyl acetate. The organic layer was washed with brine, dried over sodium sulfate and concentrated. The residue was purified by silica gel flash column chromatography (eluent: hexane/ethyl acetate=20/1) to give 4-ethynylethylbenzoate(40%).

Colorless oily substance $^1$H-NMR (CDCl$_3$) δ:1.40 (3H, t, J=7.1 Hz), 3.23 (1H, s), 4.38 (2H, q, J=7.1 Hz), 7.55 (2H, d, J=8.2 Hz), 8.00 (2H, d, J=8.2 Hz).

A mixture of 4-ethynyl ethyl benzoate(320 mg, 1.84 mmol) and decaborane(14) (337 mg, 2.76 mmol) was refluxed for 3 days in acetonitrile (1 ml) and benzene (15 ml) under argon atmosphere,. The mixture was concentrated and purified by silica gel flash column chromatography (eluent: hexane/ethyl acetate=15/1) to give ethyl 4-(1,2-dicarba-closo-dodecaboran-1-yl)benzoate (71%).

Colorless flakes (ethanol)

m.p.: 111–112° C.

$^1$H-NMR (CDCl$_3$) δ:1.39 (3H, t, J=7.1 Hz), 1.50–3.50 (10H, br m), 4.01 (1H, br s), 4.39 (2H, q, J=7.1 Hz), 7.54 (2H, d, J=8.8 Hz), 8.00 (2H, d, J=8.8 Hz)

HRMS Calcd for $C_{11}H_{20}B_{10}O_2$ 292.2466, Found 292.2487

Ethyl 4-(1,2-dicarba-closo-dodecaboran-1-yl) benzoate (374 mg, 1.28 mmol) was dissolved in THF (5 ml), 1N potassium hydroxide (3.84 ml) was added, and stirred at room temperature for 15 h. The reaction was quenched by the addition of 2N hydrochloric acid, and the mixture was extracted with ethyl acetate. The organic layer was washed with water and then brine, dried over sodium sulfate and concentrated. The remaining crystals were washed with hexane to give 4-(1,2-dicarba-closo-dodecaboran-1-yl) benzoic acid.

$^1$H-NMR (DMSO-d$_6$) δ:1.40–3.20 (10H, br m), 5.88 (1H, br s), 7.72 (2H, d, J=8.5 Hz), 7.94 (2H, d, 8.5 Hz), 13.29 (1H, br).

The benzoic acid obtained above (140 mg, 0.53 mmol) was suspended in dichloromethane (1.51 ml), oxalyl chloride (202 mg, 1.59 mmol) and catalytic amount of DMF(1 drop) were added. After stirring at room temperature for 1 h, the mixture was concentrated. The residue was dissolved in pyridine (1.5 ml), and methyl 4-aminobenzoate (84.0 mg, 0.556 mmol) was added. After stirring at room temperature for 15 h, the reaction was quenched by the addition of 2N hydrochloric acid, and the mixture was extracted with ethyl acetate. The organic layer was washed with water, saturated sodium hydrogencarbonate solution, water, and brine in order, dried over sodium sulfate and concentrated. The residue was purified by silica gel flash column chromatography (eluent: hexane/ethyl acetate=3/1) to give methyl 4-{[4-(1,2-dicarba-closo-dodecaboran-1-yl)phenyl] carboxamide}benzoate (48%).

$^1$H-NMR (CDCl$_3$) δ:1.50–3.50 (10H, m), 3.92 (3H, 8), 4.02 (1H, br s), 7.62 (2H, d, J=8.4 Hz), 7.72 (2H, d, J=8.8 Hz), 7.84 (2H, d, J=8.4 Hz), 7.89 (1H, br s), 8.07 (2H, d, J=8.8 Hz).

The methyl benzoate obtained above (94 mg, 0.236 mmol) was dissolved in THF(3 ml), 1N potassium hydroxide (1.18 ml) was added, and stirred at 40° C. for 16 h. The reaction was quenched by the addition of 2N hydrochloric acid, and the mixture was extracted with ethyl acetate. The organic layer was washed with water and then brine, dried over sodium sulfate and concentrated. The residue was purified by silica gel flash column chromatography (eluent: chloroform/methanol=5/1) to give 4-{[4-(1,2-dicarba-closo-dodecaboran-1-yl)phenyl]carboxamide}benzoic acid (BR300)(41%).

Colorless needles (ethyl acetate)

m.p.:>300° C.

$^1$H-NMR (DMSO-d$_6$) δ:1.40–3.20 (10H, br m), 5.92 (1H, br s), 7.76 (2H, d, J=8.8 Hz), 7.88 (2H, d, J=8.8 Hz), 7.94 (2H, d, J=8.8 Hz), 7.95 (2H, d, J=8.8 Hz), 10.61 (1H, s), 12.80 (1H, br)

Anal. Calcd for $C_{16}H_{21}B_{10}NO_3$: C, 50.12; H, 5.52; N, 3.65. Found C, 50.18; H, 5.80; N, 3.41.

A mixture of ethyl 3-bromobenzoate (1.0 g, 4.37 mmol), ethynyl trimethylsilane (644 mg, 6.56 mmol), diisopropylamine (929 mg, 9.20 mmol), cuprous iodide(I) (16.6 mg, 0.0872 mmol), and bis(triphenylphosphine) palladium(II) chloride (123 mg, 0.175 mmol) was heated at 45° C. for 5 h in dried THF (8 ml) under argon atmosphere. After cooling, the reaction was quenched by the addition of water, and the mixture was extracted with ethyl acetate. The organic layer was washed with brine, dried over sodium sulfate and concentrated. The residue was purified by silica gel flash column chromatography (eluent: hexane/ethyl acetate=50/1) to give ethyl 3-[(trimethylsilyl)-ethynyl] benzoate (90%)

$^1$H-NMR (CDCl$_3$) δ:0.26 (9H, s), 1.40 (3H, t, J=7.1 Hz), 4.38 (2H, q, J=7.1 Hz), 7.38 (1H, dd, J=7.3, 8.3 Hz), 7.63 (1H, d, J=7.3 Hz), 7.98 (1H, d, J=8.3 Hz), 8.13 (1H, s).

Potassium carbonate (583 mg, 4.22 mmol) was added to an ethanol solution (10 ml) of ethyl 3-[(trimethylsilyl) ethynyl]benzoate (1.04 g, 4.22 mmol), and stirred at room temperature for 2 h. The mixture was concentrated, and the residue was dissolved in ethyl acetate. The organic layer was washed with water and then brine, dried over sodium sulfate and concentrated. The residue was purified by silica gel flash column chromatography (eluent: hexane/ethyl acetate=30/1) to give ethyl 3-ethynylbenzoate (96%).

Colorless needles m.p.: 36–37° C.

$^1$H-NMR (CDCl$_3$) δ:1.40 (3H, t, J=7.1 Hz), 3.12 (1H, s), 4.34 (2H, q, J=7.1 Hz), 7.41 (1H, t, J=7.8 Hz), 7.66 (1H, dt, J=7.8, 1.5 Hz), 8.03 (1H, dt, J=7.8, 1.5 Hz), 8.17 (1H, t, J=1.5 Hz).

Ethyl 3-ethynyl benzoate was reacted with decaborane (14) and converted to ethyl 3-(1,2-dicarba-closo-dodecaboran-1-yl)benzoate similar to the case of ethyl 4-(1,2-dicarba-closo-dodecaboran-1-yl)benzoate. The yield of the product was 68%.

Colorless flakes (ethanol)

m.p.: 168–169° C.

$^1$H-NMR (CDCl$_3$) δ:1.41 (3H, t, J=7.7 Hz), 1.50–3.50 (10H, m), 4.04 (1H, br s), 440 (2H, q, J=7.1 Hz), 7.43 (1H, t, J=7.7 Hz), 7.70 (1H, ddd, J=1.1, 2.2, 7.7 Hz), 8.07 (1H, dt, J=7.7, 1.1 Hz), 8.10 (1H, t. J=1.7 Hz)

HRMS Calcd for C$_{11}$H$_{20}$B$_{10}$O$_2$ 292.2466, Found 292.2474

4-[[3-(1,2-Dicarba-closo-dodecaboran-1-yl)phenyl] carboxamide]benzoic acid (BR360) was prepared from 3-(1,2-dicarba-closo-dodecaboran-1-yl)ethylbenzoate by the same procedure that used for BR300.

Colorless needles (ethyl acetate/hexane)

m.p.: 236–239° C.

$^1$H-NMR (DMSO-d$_6$) δ:1.40–3.20 (10H, br m), 5.89 (1H, br s), 7.60 (1H, t, J=8.0 Hz), 7.82 (1H, br d, J=8.0 Hz), 7.86 (2H, d, J=8.8 Hz), 7.95 (2H, d, J=8.8 Hz), 8.04 (1H, br d, J=8.0 Hz), 8.05 (1H, br s), 10.61 (1H, s), 12.89 (1H, br)

HRMS Calcd for C$_{16}$H$_{21}$B$_{10}$NO$_3$ 383.2524, Found 383.2542

Anal. Calcd for C$_{16}$H$_{21}$B$_{10}$NO$_3$/0.5 H$_2$O: C, 48.97; H, 5.65; N, 3.57. Found C, 48.99; H, 5.83; N, 3.49.

Example 5

1.54M n-Butyl lithium/hexane solution (37.8 ml, 58.2 mmol) was added dropwise to DME solution (100 ml) of 1,2-dicarba-closo-dodecaborane (4.0 g, 27.7 mmol) at 0° C. under argon atmosphere. The mixture was stirred at room temperature for 30 min, cuprous chloride (7.13 g, 72.0 mmol) was added in one portion, and further stirred at room temperature for 2 h. After the treatment, pyridine (16.7 ml, 208 mmol) was added, then 4-iodonitrobenzene (8.28 g, 33.3 mmol) was added at one time, and heated at 100° C. for 22 h. After cooling, the mixture was diluted with diethyl ether, stirred at room temperature for 12 h, and the insoluble substance was separated and filtered with Celite. The filtrate was washed with 2N hydrochloric acid, water, and brine in order, dried over sodium sulfate and concentrated. The residue was purified by silica gel flash column chromatography (eluent: n-hexane/ethyl acetate=7/1) to give 4-(1,2-dicarba-closo-dodecaboran-1-yl)nitrobenzene (75%).

Colorless prism (ethyl acetate/hexane)

m.p.: 170–172° C.

$^1$H-NMR (CDCl$_3$) δ1.50–3.50 (10H, br m), 4.02 (1H, br s), 7.67 (2H, d, J=9.2 Hz), 8.21 (2H, d, J=9.2 Hz)

4-(1,2-Dicarba-closo-dodecaboran-1-yl) nitrobenzene (5.45 g, 20.5 mmol) in ethanol (220 ml) was hydrogenated at room temperature for 3 h under the atmospheric pressure of hydrogen using 10% Pd/C (1.36 g). After removal of catalyst by filtration, the filtrate was concentrated, and 4-(1,2-dicarba-closo-dodecaboran-1-yl)aniline was obtained (85%).

$^1$H-NMR (CDCl$_3$) δ 1.50–3.50 (10H, br m), 3.83 (3H, br), 6.56 (2H, d, J=9.2 Hz), 7.27 (2H, d, J=9.2 Hz)

Sodium hydride (40.8 mg, 1.02 mmol) was suspended in DMF (1 ml), and a solution of 4-(1,2-dicarba-closo-dodecaboran-1-yl) aniline (200 mg, 0.850 mmol) in DMF (3 ml) was added to the suspension. The mixture was stirred at room temperature for 5 min, 1-indopropane (217 mg, 1.28 mmol) was added, and further stirred at room temperature for 1.5 h. The reaction was quenched by the addition of 2N hydrochloric acid, and the mixture was neutralized with saturated sodium hydrogen carbonate solution, and extracted with diethyl ether. The organic layer was washed with water and then brine, dried over sodium sulfate and concentrated. The residue was purified by silica gel flash column chromatography (eluent: hexane/ethyl acetate=5/1) to give 4-(2-propyl-1,2-dicarba-closo-dodecaboran-1-yl) aniline(82%).

$^1$H-NMR (CDCl$_3$) δ 0.74 (3H, t, J=7.3 Hz), 1.41 (2H, m), 1.50–3.50 (10H, br m), 1.73 (2H, m), 3.90 (2H, br), 6.60 (2H, d, J=8.8 Hz), 7.36 (2H, d, J=8.8 Hz)

A mixture of 4-(2-propyl-1,2-dicarba-closo-dodecaboran-1-yl)aniline (175 mg, 0.631 mmol), ethyl 4-iodobenzoate (192 mg, 0.695 mmol), cesium carbonate (288 mg, 0.884 mmol), tris(dibenzylideneacetone)dipalladium(0) (11.6 mg, 0.0127 mmol), and 2-2'-bis(diphenylphosphino)-1,1'-binaphtyl (19.6 mg, 0.0315 mmol) in dry toluene was heated at 100–110° C. for 27 h. The reaction was quenched by the addition of water, the mixture was extracted with diethyl ether. The organic layer was washed with brine, dried over sodium sulfate and concentrated. The residue was purified by silica gel flash column chromatography (eluent: dichloromethane/hexane=1/1) to give light yellow needless of ethyl 4-[4-(2-propyl-1,2-dicarba-closo-dodecaboran-1-yl)-phenylaminobenzoate (53%).

$^1$H-NMR (CDCl$_3$) δ 0.77 (3H, t, J=7.3 Hz), 1.39 (3H, t, J=7.1 Hz), 1.44 (2H, m), 1.50–3.50 (10H, br m), 1.76 (2H, m), 4.36 (2H, q, J=7.1 Hz), 6.15 (1H, s), 7.09 (2H, d, J=8.8 Hz), 7.10 (2H, d, J=8.8 Hz), 7.52 (2H, d, J=8.8 Hz), 7.98 (2H, d, J=8.8 Hz)

Ethyl 4-[4-(2-Propyl-1,2-dicarba-closo-dodecaboran-1-yl)phenylamino]-benzoate (130 mg, 0.305 mmol) was dissolved in water (1.5 ml)-dioxane (5 ml), then concentrated sulfuric acid (1 ml) was added, and the mixture was heated at 100° C. for 15 h. The mixture was poured into ice water, and extracted with ethyl acetate. The organic layer was washed with brine, dried over sodium sulfate and concentrated. The residue was purified by silica gel flash column chromatography (eluent: hexane/ethyl acetate=2/1→1/1) to give 4-[4-(2-propyl-1,2-dicarba-closo-dodecaboran-1-yl) phenylamino]benzoic acid (BR403)(68%).

Colorless needles (eluent: ethyl acetate/hexane)

m.p.: 216–217° C.

$^1$H-NMR (DMSO-d$_6$) δ 0.71 (3H, t, J=7.3 Hz), 1.36 (2H, m), 1.50–3.20 (10H, br m), 1.80 (2H, m), 7.17 (2H, d, J=8.8 Hz), 7.19 (2H, d, J=8.8 Hz), 7.55 (2H, d, J=8.8 Hz), 7.84 (2H, d, J=8.8 Hz), 9.06 (1H, s), 12.43 (1H, s)

Anal. Calcd for C$_{18}$H$_{27}$B$_{10}$NO$_2$: C,54.39; H, 6.85; N, 3.52. Found C, 54.09; H, 6.64; N, 3.45.

3-(1,2-Dicarba-closo-dodecaboran-1-yl)nitrobenzene was prepared from 1,2-dicarba-closo-dodecaborane (2.0 g, 13.9 mmol), 1.54 M n-butyl lithium/hexane solution (19.0 ml, 29.3 mmol), cuprous chloride (3.58 g, 36.2 mmol), pyridine (8.39 ml, 104 mmol), and 3-iodonitrobenzene (4.15 g, 16.7 mmol) by a similar procedure to the method applied for preparation of 4-(1,2-dicarba-closo-dodecaboran-1-yl) nitrobenzene. The residue was purified by silica gel flash column chromatography to give 3-(1,2-dicarba-closo-dodecaboran-1-yl)nitrobenzene (34%) and 3-(1,2-dicarba-closo-dodecaboran-1-yl)aniline (9%).

Colorless prisms m.p.: 142–143° C.

$^1$H-NMR (CDCl$_3$) δ 1.50–3.50 (10H, br m), 4.03 (1H, br s), 7.58 (1H, t, J=8.2 Hz), 7.86 (1H, ddd, J=1.2, 1.8, 8.2 Hz), 8.28 (1H, ddd, J=1.2, 1.8, 8.2 Hz), 8.34 (1H, t, J=1.8 Hz)

3-(1,2-Dicarba-closo-dodecaboran-1-yl)nitrobenzene was reduced by a similar procedure that used for 4-(1,2-dicarba-closo-dodecaboran-1-yl)aniline. Purification by silica gel column chromatography gave 3-(1,2-dicarba-closo-dodecaboran-1-yl)aniline (76%).

$^1$H-NMR (CDCl$_3$) δ 1.40–3.50 (10H, br m), 3.85 (2H, br), 3.93 (1H, br s), 6.67 (1H, m), 6.78–6.81 (2H, m), 7.07 (1H, t, J=8.2 Hz)

3-(1,2-Dicarba-closo-dodecaboran-1-yl)aniline was converted to 3-(2-propyl-1,2-dicarba-closo-dodecaboran-1-yl) aniline by a similar procedure that used for 4-(2-propyl-1,2-dicarba-closo-dodecaboran-1-yl)aniline. Purification by silica gel flash column chromatography (eluent: hexane/ethyl acetate=5/1) gave 3-(2-propyl-1,2-dicarba-closo-dodecaboran-1-yl)aniline (92%).

$^1$H-NMR (CDCl$_3$) δ 0.74 (3H, t, J=7.3 Hz), 1.43 (2H, m), 1.50–3.50 (10H, br m), 1.76 (2H, m), 3.80 (2H, br), 6.74 (1H, br d, J=8.0 Hz), 6.91 (1H, br s), 6.98 (1H, br, d, J=8.0 Hz), 7.13 (1H, t, J=8.0 Hz)

Ethyl 4-[3-(2-propyl-1,2-dicarba-closo-dodecaboran-1-yl)phenylamino]-benzoate was prepared from 3-(2-propyl-1,2-dicarba-closo-dodecaboran-1-yl)aniline by a similar procedure that used for ethyl 4-[4-(2-propyl-1,2-dicarba-closo-dodecaboran-1-yl) phenylamino]benzoate. Purification by silica gel flash column chromatography (eluent: dichloromethane/hexane=1/1) gave light yellow crystals of ethyl 4-[3-(2-propyl-1,2-dicarba-closo-dodecaboran-1-yl) phenylamino]benzoate (89%).

$^1$H-NMR (CDCl$_3$) δ 0.78 (3H, t, J=7.3 Hz), 1.39 (3H, t, J=7.1 Hz), 1.45 (2H, m), 1.50–3.50 (10H, br m), 1.79 (2H, m), 4.36 (2H, q, J=7.1 Hz), 6.09 (1H, s), 7.00 (2H, d, J=8.9 Hz), 7.23 (1H, m), 7.26 (1H, m), 7.32 (1H, t, J=7.9 Hz), 7.39 (1H, br s), 7.97 (2H, d, J=8.9 Hz)

This ester was hydrolyzed by a similar procedure that used for 4-[4-(2-propyl-1,2-dicarba-closo-dodecaboran-1-yl)phenylamino]benzoic acid. The product was purified by silica gel flash column chromatography (eluent: hexane/ethyl acetate=2/1→1/1) to give 4-[3-(2-propyl-1,2-dicarba-closo-dodecaboran-1-yl)phenylamino]benzoic acid (BR453) (80%).

Colorless needles (ethyl acetate/hexane)

m.p.: 229–230° C.

$^1$H-NMR (DMSO-d$_6$) δ 0.72 (3H, t, J=7.3 Hz), 1.38 (2H, m), 1.50–3.20 (10H, br m), 1.84 (2H, m), 7.08 (2H, d, J=8.8 Hz), 7.22 (1H, br d, J=7.1 Hz), 7.34–7.41 (3H, m), 7.83 (2H, d, J=8.8 Hz), 8.94 (1H, s), 12.38 (1H, s)

Anal. Calcd for C$_{18}$H$_{27}$B$_{10}$NO$_2$: C, 54.39; H, 6.85; N, 3.52. Found C, 54.17; H, 6.78; N, 3.25.

Example 6

4-(2-Methyl-1,2-dicarba-closo-dodecaboran-1-yl) nitrobenzene (349 mg, 1.25 mmol) was dissolved in ethanol (25 ml) and hydrogenated at room temperature for 1 h under the atmospheric pressure of hydrogen using 10% Pd/C (87 mg),. After the catalyst was removed by filtration, the filtrate was concentrated to give 4-(2-methyl-1,2-dicarba-closo-dodecaboran-1-yl) aniline (96%).

$^1$H-NMR (CDCl$_3$) δ:1.40–3.50 (10H, br m), 1.68 (3H, s), 4.01 (2H, br), 6.62 (2H, d, J=8.6 Hz), 7.39 (2H, d, J=8.6 Hz).

A mixture of 4-(2-methyl-1,2-dicarba-closo-dodecaboran-1-yl)aniline (174 mg, 0.698 mmol), 4-iodo ethyl benzoate (193 mg, 0.699 mmol), cesium carbonate (318 mg, 0.976 mmol), tris (dibenzylidene acetone) dipalladium (0)(12.8 mg, 0.0140 mmol), and 2-2'-bis (diphenylphosphino)-1,1'-binaphtyl (21.7 mg, 0.0348 mmol) in dry toluene was heated at 110° C. for 24 h. The reaction was quenched by the addition of water, and the mixture was extracted with diethyl ether. The organic layer was washed with brine, dried over sodium sulfate and concentrated. The residue was purified by silica gel flash column chromatography (eluent: dichloromethane/hexane=1/1) to give light yellow needles of ethyl 4-[4-(2-methyl-1,2-dicarba-closo-dodecaboran-1-yl)phenylamino]benzoate (71%).

$^1$H-NMR (CDCl$_3$) δ:1.50–3.50 (10H, br m), 1.39 (3H, t, J=7.1 Hz), 1.72 (3H, s), 4.36 (2H, q, J=7.1 Hz), 6.15 (1H, br s), 7.09 (4H, d, J=8.8 Hz), 7.54 (2H, d, J=8.8 Hz), 7.98 (2H, d, J=8.8 Hz).

Ethyl 4-[4-(2-Methyl-1,2-dicarba-closo-dodecaboran-1-yl)phenylamino]-benzoate (95 mg, 0.239 mmol) was dissolved in THF(3 ml), 1N potassium hydroxide (1.20 ml) was added, and refluxed for 27 h. The reaction was quenched by the addition of 2N hydrochloric acid, and the mixture was extracted with ethyl acetate. The organic layer was washed with water then brine, dried over sodium sulfate and concentrated. The residue was purified by silica gel flash column chromatography (eluent: hexane/ethyl acetate=2/1) to give 4-[4-(2-methyl-1,2-dicarba-closo-dodecaboran-1-yl) phenylamino]benzoic acid (BR401)(31%), and ethyl 4-[4-(2-methyl-1,2-dicarba-closo-dodecaboran-1-yl) phenylamino]benzoate was recovered (27%).

BR401 : Colorless needles (ethyl acetate/hexane)

m.p.: 258–260° C.

$^1$H-NMR (DMSO-d$_6$) δ:1.40–3.20 (10H, br m), 1.73 (3H, s), 7.16 (2H, d, J=8.8 Hz), 7.20 (2H, d, J=8.8 Hz), 7.56 (2H, d, J=8.8 Hz), 7.83 (2H, d, J=8.8 Hz), 9.06 (1H, s), 12.42 (1H, br)

Anal. Calcd for C$_{16}$H$_{23}$B$_{10}$NO$_3$: C, 52.01; H, 6.27; N, 3.79. Found C, 52.11; H, 6.54; N, 3.64.

BR431 was synthesized from [4-(1,2-dicarba-closo-dodecaboran-1-yl)-2-methyl nitrobenzene by a similar procedure that used for ethyl 4-[4-(2-methyl-1,2-dicarba-closo-dodecaboran-1-yl)phenylamino]benzoate. The product was purified by silica gel flash column chromatography (eluent: hexane/ethyl acetate=5/1→3/1) to give light orange needless of ethyl 4-{4-(1,2-dicarba-closo-dodecaboran-1-yl)-2-methyl}-phenylamino]benzoate (61%).

$^1$H-NMR (CDCl$_3$) δ:1.38 (3H, t, J=7.2 Hz), 1.50–3.50 (10H, br m), 2.26 (3H, s), 3.92 (1H, br s), 4.35 (2H, q, J=7.2 Hz), 5.70 (1H, s), 6.95 (2H, d, J=9.0 Hz), 7.23 (1H, d, J=8.8 Hz), 7.27 (2H, dd, J=2.4, 8.8 Hz), 7.33 (1H, d, J=2.4 Hz), 7.95 (2H, d, J=9.0 Hz).

Sodium hydride (33.2 mg, 0.830 mmol) was suspended in DMF (1 ml), and ethyl 4-[4-(1,2-dicarba-closo-dodecaboran-1-yl)-2-methy) phenylamino]benzoate (150 mg, 0.377 mmol) in DMF (3 ml) was added to the suspension. The mixture was stirred at room temperature for 5 min, methyl iodide (161 mg, 1.13 mmol) was added, and further stirred at room temperature for 20 min. The reaction was quenched by the addition of 2N hydrochloric acid, and the mixture was extracted with diethyl ether. The organic layer was washed with water and then brine, dried over sodium sulfate and concentrated. The residue was purified by silica gel flash column chromatography (eluent: hexane/ethyl acetate=10/1) to give ethyl 4-{N-methyl-[2-methyl-4-(2-methyl-1,2-dicarba-closo-dodecaboran-1-yl)]phenylamino] benzoate (74%).

$^1$H-NMR (CDCl$_3$) δ:1.35 (3H, t, J=7.1 Hz), 1.50–3.50 (10H, br m), 1.76 (3H, s), 2.14 (3H, s), 3.28 (3H, s), 4.35 (2H, q, J=7.1 Hz), 6.48 (2H, d, J=9.2 Hz), 7.16 (1H, d, J=8.4

Hz), 7.53 (1H, dd, J=2.4, 8.4 Hz), 7.57 (1H, d, J=2.4 Hz), 7.88 (2H, d, J=9.2 Hz).

Ethyl 4-[N-Methyl-[2-methyl-4-(2-methyl-1,2-dicarba-closo-dodecaboran-1-yl)]phenylamino]ethyl benzoate (111 mg, 0.261 mmol) was dissolved in THF (3 ml), 1N potassium hydroxide (1.95 ml) was added, and refluxed for 26 h. The reaction was quenched by the addition of 2N hydrochloric acid, and the mixture was extracted with ethyl acetate. The organic layer was washed with water then brine, dried over sodium sulfate and concentrated. The residue was purified by silica gel flash column chromatography (eluent: hexane/ethyl acetate=2/1) to give 4-{N-methyl-[2-methyl-4-(2-methyl-1,2-dicarba-closo-dodecaboran-1-yl)]phenylamino}benzoic acid (BR431) (12%), and ethyl 4-[N-methyl-[2-methyl-4-(2-methyl-1,2-dicarba-closo-dodecaboran-1-yl)] phenylamino]benzoate was recovered (16%).

BR431: Colorless needles (ethyl acetate/hexane)

m.p.: 296–298° C.

$^1$H-NMR (DMSO-$d_6$) δ:1.40–3.20 (10H, br m), 1.80 (3H, s), 1.99 (3H, s), 3.24 (3H, s), 6.51 (2H, d, J=9.1 Hz), 7.31 (1H, d, J=8.3 Hz), 7.63 (1H, dd, J=2.5, 8.3 Hz), 7.69 (1H, d, J=2.5 Hz), 7.74 (2H, d, J=9.1 Hz), 12.18 (1H, br s)

Anal. Calcd for $C_{16}H_{23}B_{10}NO_3$: C, 54.39; H, 6.85; N, 3.52. Found C, 54.25; H, 6.95; N, 3.53.

Example 7

1,12-Dicarba-closo-dodecaborane (3.5 g, 24.3 mmol) was dissolved in DME, 1.54 M n-butyl lithium/hexane solution (16.6 ml, 25.6 mmol) was added dropwise at 0° C. under argon atmosphere. The mixture was stirred at room temperature for 30 min, cuprous chloride (3.13 g, 31.6 mmol) was added in one portion, and further stirred at room temperature for 1 h. Then, pyridine (14.7 ml, 183 mmol) was added, and 4-iodo anisole (5.97 g, 25.5 mmol) was added in one portion, and heated at 100° C. for 48 h. After cooling, the mixture was diluted with diethyl ether, then stirred at room temperature for 3 h, and insoluble substance was separated by filtration with Celite. The filtrate was washed with 2N hydrochloric acid, $Na_2S_2O_s$ solution, water, and brine in order, dried over sodium sulfate and concentrated. The residue was purified by silica gel flash column chromatography (eluent: hexane→hexane/ethyl acetate=10/1) to give 1-(4-methoxyphenyl)-1,12-dicarba-closo-dodecaborane(O-methy-BE 100)(60%) and 1,12-bis (4-methoxyphenyl)-1,12-dicarba-closo-dodecaborane (O,O'-dimethyl-BE 160)(13%).

O-methy-BE100: Colorless needles; $^1$H-NMR (CDCl$_3$) δ:1.50–3.30 (10H, br m), 2.75 (1H, br s), 3.74 (3H, s), 6.68 (2H, d, J=9.1 Hz), 7.11 (2H, d, J=9.1 Hz).

O,O'-dimethyl-BE 160: Colorless needles; $^1$H-NMR (CDCl$_3$) δ:1.50–3.60 (10H, br m), 3.75 (6H, s), 6.69 (4H, d, J=9.0 Hz), 7.15 (4H, d, J=9.0 Hz).

O-Methyl-BE100 (100 mg, 0.399 mmol) was dissolved in dichloromethane (1 ml), 1M boron tribromide/dichloro methane solution (0.48 ml) was added dropwise under cooling with dry ice/acetone, and stirred at room temperature for 2 h. The mixture was poured into ice water, and extracted with dichloromethane. The organic layer was washed with brine, dried over sodium sulfate and concentrated. The residue was purified by silica gel flash column chromatography (eluent: hexane/ethyl acetate=10/1) to give 1-(4-hydroxyphenyl)-1,12-dicarba-closo-dodecaborane (BE100) (93%).

Colorless needles (dichloromethane/hexane)

m.p.: 193–194° C.

$^1$H-NMR (CDCl$_3$) δ:1.40–3.20 (10 H, br m), 2.75 (1H, br s), 4.73 (1H, br s), 6.61 (2H, d, J=9.0 Hz), 7.07 (2H, d, J=9.0 Hz)

HRMS Calcd for $C_8H_{16}B_{10}O$ 236.2204, Found 236.2227

Anal. Calcd for $C_8H_{16}B_{10}O$: C, 40.66; H, 6.82. Found C, 40.67; H, 6.79.

O,O'-Dimethyl-BE160 (150 mg, 0.421 mmol) was dissolved in dichloromethane(5 ml), 1M boron tribromide/dichloromethane solution (1.05 ml) was added dropwise under cooling with dry ice/acetone, and stirred at room temperature for 2 h. The mixture was poured into ice water, and extracted with ethyl acetate. The organic layer was washed with brine, dried over sodium sulfate and concentrated. The residue was purified by silica gel flash column chromatography (eluent: hexane/ethyl acetate=5/1) to give 1,12-bis(4-hydroxyphenyl)-1,12-dicarba-closo-dodecaborane (BE160) (93%).

Colorless prisms (ethyl acetate/hexane)

m.p.: 292–294° C.; $^1$H-NMR (DMSO-$d_6$) δ: 1.70–3.30 (10H, br m), 6.60 (4H, d, J=8.9 Hz), 7.00 (4H, d, J=8.9 Hz) 9.63 (2H, s)

HRMS Calcd for $C_{14}H_{20}B_{10}O_2$ 328.2466, Found 328.2480

Anal. Calcd for $C_{14}H_{20}B_{10}O_2$: C, 51.20; H, 6.14. Found C, 50.89; H, 6.17.

Example 8

O-Methyl-BE100 (500 mg, 2.00 mmol) was dissolved in benzene/diethyl ether (2:1, 15 ml), 1.54M n-butyl lithium/hexane solution (1.56 ml, 2.40 mmol) was added dropwise at 0° C. under argon atmosphere, then stirred at room temperature for 30 min. The mixture was cooled to 0° C., methyl chloroformate (227 mg, 2.40 mmol) was added dropwise, and stirred at room temperature for 3 h. The reaction was quenched by the addition of water, and the mixture was extracted with ethyl acetate. The organic layer was washed with brine, dried over sodium sulfate and concentrated. The residue was purified by silica gel flash column chromatography (eluent: hexane/ethyl acetate=50/1) to give 1-methoxycarbonyl-12-(4-methoxyphenyl-1,12-dicarba-closo-dodecaborane (O-methyl-BE110) (91%).

Colorless needles $^1$H-NMR (CDCl$_3$) δ:1.60–3.40 (10 H, br m), 3.65 (3H, s), 3.74 (3H, s), 6.68 (2H, d, J=9.1 Hz), 7.08 (2H, d, J=9.1 Hz).

O-Methyl-BE110 was demethylated by a similar procedure that used for BE160. The product was purified by silica gel flash column chromatography (eluent: hexane/ethyl acetate=6/1) to give 1-methoxycarbonyl-12-(4-hydroxyphenyl)-1,12-dicarba-closo-dodecaborane (BE110) (99%).

Colorless prisms (dichloromethane/hexane)

m.p.: 178–179° C.

$^1$H-NMR (CDCl$_3$) δ:1.60–3.40 (10H, br m), 3.65 (3H, s), 4.84 (1H, br), 6.61 (2H, d, J=9.0 Hz), 7.04 (2H, d, J=9.0 Hz)

HRMS Calcd for $C_{10}H_{18}B_{10}O_3$ 294.2259, Found 294.2265

Anal. Calcd for $C_{10}H_{18}B_{10}O_3$: C, 40.81; H, 6.16. Found C, 40.66; H, 6.18.

To a suspension of lithium aluminum hydride (25.8 mg, 0.680 mmol) in THF (3 ml), O-methyl-BE110 (150 mg, 0.486 mmol) in THF (2 ml) was added dropwise at 0° C., then stirred at room temperature for 2.5 h. The reaction was quenched by the addition of 2N hydrochloric acid, and the mixture was extracted with ethyl acetate. The organic layer was washed with water and then brine, dried over sodium sulfate and concentrated to give 1-hydroxymethyl-12-(4-methoxyphenyl)-1,12-dicarba-closo-dodecaborane (O-methyl-BE120) (99%).

Colorless needles; $^1$H-NMR (CDCl$_3$) δ: 1.50–3.30 (10H, br m), 3.54 (2H, s), 3.74 (3H, s), 6.68 (2H, d, J=9.2 Hz), 7.11 (2H, d, J=9.2 Hz).

O-Methyl-BE120 was demethylated by a similar procedure that used for BE160. The product was purified by silica gel flash column chromatography (eluent: hexane/ethyl acetate=4/1) to give 1-hydroxymethyl-12-(4-hydroxyphenyl)-1,12-dicarba-closo-dodecaborane (BE120) (100%).

Colorless needles (dichloromethane/hexane); m.p.: 184–185° C.; $^1$H-NMR (CDCl$_3$) δ: 1.50–3.30 (10H, br m), 3.54 (2H, s), 4.87 (1H, br), 6.61 (2H, d, J=8.9 Hz), 7.06 (2H, d, J=8.9 Hz); HRMS Calcd for C$_9$H$_{18}$B$_{10}$O$_2$ 266.2310, Found 266.2310

Anal. Calcd for C$_9$H$_{18}$B$_{10}$O$_2$: C, 40.59; H, 6.81. Found C, 40.30; H, 6.59.

Example 9

O-Methyl-BE110 (260 mg, 0.843 mmol) was dissolved in THF (3 ml), 1N potassium hydroxide (4.22 ml) was added, and stirred at room temperature for 17 h. The reaction was quenched by the addition of 2N hydrochloric acid, and the mixture was extracted with ethyl acetate. The organic layer was washed with water and then brine, dried over sodium sulfate and concentrated to give 1-hydroxycarbonyl-12-(4-brine, dried over sodium sulfate and concentrated to give 1-hydroxycarbonyl-12-(4-methoxyphenyl)-1,12-dicarba-closo-dodecaborane (O-methyl-BE 130) (quantitatively).

Colorless needles; $^1$H-NMR (DMSO-d$_6$) δ:1.60–3.40 (10H, br m), 3.69 (3H, s), 6.78 (2H, d, J=9.1 Hz), 7.08 (2H, d, J=9.1 Hz), 14.06 (1H, br).

O-Methyl-BE130 was demethylated by a similar procedure that used for BE160 to give 1-hydrocarbonyl-12-(4-hydroxyphenyl)-12-dicarba-closo-dodecaborane (BE130).

Colorless needles (ethyl acetate/dichloromethane/hexane); m.p.: 249–252° C.; $^1$H-NMR (DMSO-d$_6$) δ:1.60–3.40 (10H, br m), 6.57 (2H, d, J=8.8 Hz), 6.94 (2H, d, J=8.8 Hz), 9.58 (1H, s).

Anal. Calcd for C$_9$H$_{16}$B$_{10}$O$_3$: C, 38.56; H, 5.75. Found C, 38.39; H, 5.82.

A mixture of BE130 (50 mg, 0.170 mmol), triethylamine (51.6 mg, 0.510 mmol), DMAP (2.1 mg, 0.0172 mmol), and DPPA (70.1 mg, 0.254 mmol) in t-butanol (3 ml) was refluxed for 24 h. The mixture was concentrated, and the residue was dissolved in ethyl acetate. The product was washed with water then brine, dried over sodium sulfate and concentrated. The residue was purified by silica gel flash column chromatography (eluent: hexane/ethyl acetate=20/1) to give 1-tert-butoxycarbonylamino-12-(4-methoxyphenyl)-1,12-dicarba-closo-dodecaborane (41%).

Colorless needles; $^1$H-NMR (CDCl$_3$) δ:1.39 (9H, s), 1.60–3.40 (10H, br m), 3.73 (3H, s), 4.89 (1H,s), 6.67 (2H, d, J=9.0 Hz), 7.11 (2H, d, J=9.0 Hz).

The Boc protected product obtained above (62 mg, 0.170 mmol) was dissolved in dichloromethane (2 ml), TFA (0.4 ml) was added, and stirred at room temperature for 2.5 h. The reaction was quenched by the addition of saturated sodium hydrogen carbonate solution, and the mixture was extracted with dichloromethane. The organic layer was washed with brine, dried over sodium sulfate and concentrated to give 1-amino-12-(4-methoxyphenyl)-1,12-dicarba-closo-dodecaborane (O-methyl-BE140) (100%).

Colorless needles $^1$H-NMR (CDCl$_3$) δ:1.50–3.30 (10H, br m), 3.73 (3H, s), 6.67 (2H, d, J=9.0 Hz), 7.11 (2H, d, J=9.0 Hz).

O-Methyl-BE140 was demethylated by a similar procedure that used for BE 160. The mixture was poured into cool saturated sodium hydrogencarbonate solution, and extracted with ethyl acetate. The organic layer was washed with brine, dried over sodium sulfate and concentrated. The residue was purified by silica gel flash column chromatography (eluent: hexane/ethyl acetate=5/1) to give 1-amino-12-(4-hydroxyphenyl)-1,12-dicarba-closo-dodecaborane (BE140) (100%).

Colorless needles (dichloromethane/hexane)

m.p.: 169–171° C.

$^1$H-NMR (CDCl$_3$) δ: 1.50–3.30 (10H, br m), 2.05 (2H, br s), 4.81 (1H, s), 6.59 (2H, d, J=9.0 Hz), 7.06 (2H, d, J=9.0 Hz)

HRMS Calcd for C$_9$H$_{17}$B$_{10}$NO 251.2313, Found 251.2299

Example 10

O-Methyl-BE100 (500 mg, 2.00 mmol) was dissolved in diethyl ether (5 ml), 1.54M n-butyl lithium/hexane solution (1.56 ml, 2.40 mmol) was added dropwise at 0° C. under argon atmosphere, and then stirred at room temperature for 2 h. Acetyl chloride (236 mg, 3.01 mmol) was dissolved in THF (1 ml) and added dropwise under cooling with dry ice/acetone bath, then stirred at room temperature for 18 h. The reaction was quenched by the addition of water, and the mixture was extracted with ethyl acetate. The organic layer was washed with brine, dried over sodium sulfate and concentrated. The residue was purified by silica gel flash column chromatography (eluent: hexane→hexane/ethyl acetate=30/1) to give 1-acetyl-12-(4-methoxy)-1,12-dicarba-closo-dodecaborane (O-methyl-BE150) (12%) and the starting material (67%).

Colorless needles $^1$H-NMR (CDCl$_3$) δ:1.60–3.40 (10H, br m), 2.11 (3H, s), 3.74 (3H, s), 6.68 (2H, d, J=9.1 Hz), 7.09 (2H, d, J=9.1 Hz).

O-Methyl-BE150 was demethylated by a similar procedure that used for BE160. The product was purified by silica gel flash column chromatography (eluent: hexane/ethyl acetate=5/1) to give 1-acetyl-12-(4-hydroxyphenyl)-12-dicarba-closo-dodecaborane (BE150) (19%).

Colorless needles (dichloromethane/hexane)

$^1$H-NMR (CDCl$_3$) δ:1.50–3.30 (10H, br m), 2.11 (3H, s), 4.85 (1H, s), 6.62 (2H, d, J=8.9 Hz), 7.05 (2H, d, J=8.9 Hz).

O-Methyl-BE150 (70 mg, 0.239 mmol) was suspended in ethanol (3 ml), sodium boron hydride (4.52 mg, 0.119 mmol) was added, and stirred at room temperature for 30 min. The reaction was quenched by the addition of 2N hydrochloric acid, and the mixture was extracted with ethyl acetate. The organic layer was washed with water then brine, dried over sodium sulfate and concentrated. The residue was purified by silica gel flash column chromatography (eluent: hexane/ethyl acetate=10/1) to give 1-hydroxyethyl-12-(4-methoxyphenyl)-1,12-dicarba-closo-dodecaborane (O-methyl-BE121) (78%).

Colorless needles

¹H-NMR (CDCl₃) δ: 1.11 (3H, d, J=6.4 Hz), 1.50–3.30 (10H, br m), 3.74 (1H, q, J=6.4 Hz), 3.74 (3H, s), 6.68 (2H, d, J=9.1 Hz), 7.11 (2H, d, J=9.1 Hz).

Anal. Calcd for $C_{10}H_{20}B_{10}O_2$: C, 42.84; H, 7.14. Found C, 42.93; H, 7.50.

O-Methyl-BE121 was demethylated by a similar procedure that used for BE160. The product was purified by silica gel flash column chromatography (eluent: hexane/ethyl acetate=5/1) to give 1-hydroxyethyl-12-(4-hydroxyphenyl)-1,12-dicarba-closo-dodecaborane (BE121) (94%).

Colorless flakes (dichloromethane/hexane)

m.p.: 173–174° C.

¹H-NMR (CDCl₃) δ:1.11 (3H, d, J=6.4 Hz), 1.50–3.30 (10H, br m), 3.74 (1H, q, J=6.4 Hz), 4.84 (1H, br), 6.61 (2H, d, J=9.0 Hz), 7.07 (2H, d, J=9.1 Hz)

HRMS Calcd for $C_{10}H_{20}B_{10}O_2$ 280.2466, Found 280.2466

Example 11

1,7-Dicarba-closo-dodecaborane (3.5 g, 24.3 mmol) was dissolved in DME, 1.54 M n-butyl lithium/hexane solution (16.6 ml, 25.6 mmol) was added dropwise at 0° C. under argon atmosphere. The mixture was stirred at room temperature for 30 min, cuprous chloride (3.13 g, 31.6 mmol) was added in one portion, and further stirred at room temperature for 1 h. Then, pyridine (14.7 ml, 183 mmol) was added, 4-iodoanisole (5.97 g, 25.5 mmol) was added in one portion, and heated at 100° C. for 48 h. After cooling, the mixture was diluted with diethyl ether, stirred at room temperature for 3 h, and insoluble substance was separated by filtration with Celite. The filtrate was washed with 2N hydrochloric acid, $Na_2S_2O_3$ solution, water, and brine in order, dried over sodium sulfate and concentrated. The residue was purified by silica gel column chromatography (eluent: hexane→hexane/ethyl acetate=30/1) to give 1-(4-methoxyphenyl)-1,7-dicarba-closo-dodecaborane (O-methyl-BE200) (41%) and 1,7-bis(4-methoxyphenyl)-1,7-dicarba-closo-dodecaborane (O,O'-dimethyl-BE260) (17%).

O-methyl-BE200

Colorless needles

¹H-NMR (CDCl₃) δ:1.50–3.70 (10H, br m), 3.04 (1H, br s), 3.77 (3H, s), 6.76 (2H, d, J=9.2 Hz), 7.33 (2H, d, J=9.2 Hz).

O,O'-dimethyl-BE260

Colorless needles

¹H-NMR (CDCl₃) δ:1.50–3.70 (10H, br m), 3.78 (6H, s), 6.77 (4H, d, J=9.0 Hz), 7.37 (4H, d, J=9.0 Hz).

O-Methyl-BE200 was demethylated by a similar procedure that used for BE100. The product was purified by silica gel flash column chromatography (eluent: hexane/ethyl acetate=10/1) to give 1-(4-hydroxyphenyl)-1,7-dicarba-closo-dodecaborane (BE200) (92%).

Colorless needles (dichloromethane/hexane)

m.p.: 180–181° C.

¹H-NMR (CDCl₃) δ:1.50–3.70 (10H, br m,), 3.04 (1H, br s), 4.81 (1H, s), 6.69 (2H, d, J=8.9 Hz), 7.28 (2H, d, J=8.9 Hz).

Anal. Calcd for $C_8H_{16}B_{10}O$: , 40.66; H, 6.82. Found C, 40.52; H, 6.68.

O,O'-Dimethyl-BE260 was demethylated by a similar procedure that used for BE160. The product was purified by silica gel flash column chromatography (eluent: hexane/ethyl acetate=3/1) to give 1,7-bis(4-hydroxyphenyl)-1,7-dicarba-closo-dodecaborane (BE260) (85%).

Colorless needles (ethyl acetate/hexane)

m.p.: 198–199° C.

¹H-NMR (DMSO-d₆) δ:1.50–3.80 (10H, br m), 6.68 (4H, d, J=8.9 Hz), 7.26 (4H, d, J=8.9 Hz), 9.73 (2H, s)

Anal. Calcd for $C_{14}H_{20}B_{10}O_2$: C, 51.20; H, 6.14. Found C, 51.14; H, 6.07.

Example 12

2,3,4,5,6,7,8,9,10,11-Decamethyl-1,12-dicarba-closo-dodecaborane (1.36 g, 4.78 mmol) was dissolved in dry THF(100 ml), methyl lithium (1.02 M, ether solution, 42.1 ml, 48.0 mmol) was added dropwise at 0° C. in 10 min under argon atmosphere, then stirred at room temperature for 5 h. The mixture was poured into dry ice, 2N hydrochloric acid was added to acidify, and the mixture was extracted with ethyl acetate. The organic layer was washed with saturated brine, dried over magnesium sulfate, and the solvent was evaporated. The residue was purified by silica gel column chromatography (eluent: n-hexane, 50% chloroform/n-hexane, chloroform). The starting material (312.3 mg, 22.9%) was recovered from n-hexane eluent, and white solid of 2,3,4,5,6,7,8,9,10,11-decamethyl-1,12-dicarba-closo-dodecaborane-1-carboxylic acid (1.20 g, 76.4%) was obtained from chloroform eluent.

Colorless prisms (benzene)

m.p.: 224–225° C.

Anal. Calcd for $C_{13}B_{10}H_{32}O_2$: C, 47.53; H, 9.82. Found C, 47.33; H, 9.59. ¹H-NMR (CDCl₃, 400 MHz) δ 2.21 (1H, s, CH), 0.13, 0.07 (each 15H, s, BCH₃). ¹¹B-NMR (CDCl₃, 160.35 MHz) δ −7.98, −9.49 (each 5B, s, BCH₃).

Thionyl chloride (6 ml) and dry DMF (0.06 ml) were added to 2,3,4,5,6,7,8,9, 10,11-decamethyl-1,12-dicarba-closo-dodecaborane-1-carboxylic acid (60.1 mg, 0.18 mmol) under argon atmosphere, and heated at 90° C. for 5 h. Excess amount of thionyl chloride was evaporated under reduced pressure, water was added to the residue, and the residue was extracted with ethyl acetate. The organic layer was washed with saturated brine, dried over magnesium sulfate, and the solvent was evaporated. The residue was purified by silica gel column chromatography (eluent: n-hexane) to give white solid of 2,3,4,5,6,7,8,9,10,11-decamethyl-1,12-dicarba-closo-dodecaborane-1-carbonyl chloride (59.5 mg, 93.7%).

Colorless prisms (methanol)

m.p.: 183–184° C.

Anal. Calcd for $C_{13}B_{10}H_{31}OCl$: C, 45.00; H, 9.01. Found C, 45.00; H, 8.78. ¹H-NMR (CDCl₃, 400 MHz) δ 2.29 (1H, s, CH), 0.22, 0.10 (each 15H, s, BCH₃). ¹¹B-NMR (CDCl₃, 160.35 MHz) δ −7.64, −9.32 (each 5B, s, BCH₃).

2,3,4,5,6,7,8,9,10,11-Decamethyl-1,12-dicarba-closo-dodecaborane-1-carbonyl chloride (500 mg, 1.44 mmol) was dissolved in dry DMF (15 ml) under argon atmosphere, sodium azide (140.4 mg, 2.16 mmol) was added at 0° C., and stirred at 30° C. for 30 min. The mixture was poured into water, and extracted with ethyl acetate. The organic layer was washed with saturated brine, dried over magnesium sulfate, and the solvent was evaporated. The residue was purified by silica gel column chromatography (eluent: n-hexane) to give white solid of 2,3,4,5,6,7,8,9,10,11-decamethyl-1,12-dicarba-closo-dodecaborane-1-carbonyl azide (487.1 mg, 95.6%) Colorless flakes (ethanol-dichloromethane)

m.p.: 157–158° C.

$^1$H-NMR (CDCl$_3$, 400 MHz) δ 2.23 (1H, s, CH), 0.16, 0.07 (each 15H, s, BCH$_3$).

2,3,4,5,6,7,8,9,10,11-Decamethyl-1,12-dicarba-closo-dodecaborane-1-carbonyl azide (487.1 mg, 1.38 mmol) was dissolved in dry toluene (50 ml) under argon atmosphere, and heated at 100° C. for 2 h. The mixture was poured into water, and extracted with ethyl acetate. The organic layer was washed with saturated brine, dried over magnesium sulfate and the solvent was evaporated. The residue was purified by silica gel column chromatography (eluent: n-hexane) to give white solid of 2,3,4,5,6,7,8,9,10,11-decamethyl-1,12-dicarba-closo-dodecaboran-1-yl isocyanate (439.4 mg, 98.0%).

Colorless prisms (acetonitrile-dichloromethane)

m.p.: 162–163° C.

Anal. Calcd for C$_{13}$B$_{10}$H$_{31}$ON: C, 47.97; H, 9.60; N, 4.30. Found C, 47.96; H, 9.30; N, 4.24.

$^1$H-NMR (CDCl$_3$, 400 MHz) δ 1.92 (1H, s, CH), 0.08, 0.03 (each 15H, s, BCHs). $^{11}$B-NMR (CDCl$_3$, 160.35 MHz) δ −8.30, −11.20 (each 5B, s, BCH$_3$).

2,3,4,5,6,7,8,9,10,11-Decamethyl-1,12-dicarba-closo-dodecaboran-1-yl-isocyanate (337.4 mg, 1.04 mmol) was dissolved in methanol (30 ml), and heated at 80° C. for 24 h. The solvent was evaporated under reduced pressure to give white solid of 1-methoxycarbonylamino-2,3,4,5,6,7,8,9,10,11-decamethyl-1,12-dicarba-closo-dodecaborane (367.4 mg, 99.1%).

Colorless prisms (methanol)

m.p.: 184° C.

Anal. Calcd for C$_{14}$B$_{10}$H$_{35}$O$_2$N: C, 47.03; H, 9.87; N, 3.92. Found C, 46.76; H, 9.68; N, 3.80.

$^1$H NMR (CDCl$_3$, 400 MHz) δ 4.36 (1H, s), 3.54(3H, s), 1.96 (1H, s, CH), 0.09, 0.07 (each 15H, s, BCH$_3$).

1-Methoxy carbonylamino-2,3,4,5,6,7,8,9,10,11-decamethy-1,12-dicarba-closo-dodecaborane (266.2 mg, 0.745 mmol) was dissolved in methanol (30 ml), 2N potassium hydroxide solution (3.5 ml) was added, and heated at 80° C. for 3 days. The mixture was poured into water, and extracted with ethyl acetate. The organic layer was washed with saturated brine, dried over magnesium sulfate, and the solvent was removed to give white powders of 1-amino-2,3,4,5,6,7,8,9,10,11-decamethyl-1,12-dicarba-closo-dodecaborane (218.2 mg, 97.8%)

Colorless flakes (methanol)

m.p.: 170° C.

$^1$H NMR (CDCl$_3$, 400 MHz) δ 1.83 (1H, s, CH), 1.16 (2H, br s, NH$_2$), 0.06, −0.08 (each 15H, s, BCH$_3$).

2,3,4,5,6,7,8,9,10,11-Decamethyl-1,12-dicarba-closo-dodecaborane-1-carbonyl chloride (58.9 mg, 0.17 mmol) was dissolved in 1,2-dichlorobenzene (1 ml) under argon atmosphere, ethyl 4-aminobenzoate (140.4 mg, 0.85 mmol) was added, and heated at 180° C. for 24 h. The solvent was removed under reduced pressure, 2N hydrochloric acid was added, and the residue was extracted with ethyl acetate. The organic layer was washed with saturated brine, dried over magnesium sulfate and the solvent was evaporated. The residue was purified by silica gel column chromatography (eluent: 20% ethyl acetate/n-hexane) to give white solid of ethyl 4-(2,3,4,5,6,7,8,9,10,11-decamethyl-1,12-dicarba-closo-dodecaborane-1-carbonylamino)benzoate (89.1 mg, quant.).

Colorless flakes (dichloromethane-hexane)

m.p.: 135–137° C.

Anal. Calcd for C$_{22}$B$_{10}$H$_{41}$O$_3$N: C, 55.55; H, 8.69; N, 2.95. Found C, 55.34; H, 8.41; N, 3.02.

$^1$H NMR (CDCl$_3$, 400 MHz) δ 7.96 (2H, d, J=8.8 Hz), 7.41 (2H, d, J=8.8 Hz), 7.09 (1H, br s, NH), 4.35 (2H, q, J=7.1 Hz), 2.27 (1H, s, CH), 1.38 (3H, t, J=7.1 Hz), 0.27, 0.12 (each 15H, s, BCH$_3$)

Ethyl 4-(2,3,4,5,6,7,8,9,10,11-decamethyl-1,12-dicarba-closo-dodecaborane-1-carbonylamino) ethyl benzoate (56.2 mg, 0.118 mmol) was dissolved in ethanol (5 ml), 1N potassium hydroxide solution (1 ml) was added, and heated at 80° C. for 1 h. 2N hydrochloric acid was added, and the mixture was extracted with ethyl acetate. The organic layer was washed with water then saturated brine, dried over magnesium sulfate and the solvent was evaporated to give white solid of 4-(2,3,4,5,6,7,8,9,10,11-decamethyl-1,12-dicarba-closo-dodecaborane-1-carbonylamino) benzoic acid (60.2 mg, quant.)(BR630).

Colorless needles (dichloromethane hexane)

m.p.: 285–286° C.

Anal. Calcd for C$_{20}$B$_{10}$H$_{37}$O$_3$N: C, 53.67; H, 8.33; N, 3.13. Found C, 53.68; H, 8.22; N, 3.01.

$^1$H NMR (CDCl$_3$, 400 MHz) δ 8.01 (2H, d, J=9.0 Hz), 7.45 (2H, d, J=8.8 Hz), 7.13 (1H, br s, NH), 2.27 (1H, s, CH), 0.27, 0.12 (each 15H, s, BCH$_3$).

1-Amino-2,3,4,5,6,7,8,9,10,11-decamethyl-1,12-dicarba-closo-dodecaborane (50.0 mg, 0.167 mmol) was dissolved in 1,2-dichlorobenzene (1 ml) under argon atmosphere, terephthalic acid monomethyl ester chloride (49.8 mg, 0.251 mmol) and anhydrous pyridine (0.2 ml) were added, and heated at 180° C. for 18 h. After the solvent was removed under reduced pressure, 2N hydrochloric acid was added to the residue, and extracted with ethyl acetate. The organic layer was washed with saturated sodium hydrogencarbonate solution then saturated brine, dried over magnesium sulfate and the solvent was evaporated. The residue was purified by silica gel column chromatography (eluent: 5% ethyl acetate/n-hexane) to give white solid of methyl 4-(2,3,4,5,6,7,8,9,10,11-decamethyl-1,12-dicarba-closo-dodecaboran-1-amino carbonyl)benzoate (40.6 mg, 52.5%). The compound (40.5 mg, 0.088 mmol) was dissolved in methanol (5 ml), 1N potassium hydroxide solution (1 ml) was added, and heated at 80° C. for 1 h. 2N hydrochloric acid was added, and the mixture was extracted with ethyl acetate. The organic layer was washed with water then saturated brine, dried over magnesium sulfate and the solvent was evaporated to give white solid of 4-(2,3,4,5,6,7,8,9,10,11-decamethyl-1,12-dicarba-closo-dodecaborane-1-carbonylamino) benzoic acid (BR635)(39.7 mg, quant.).

Colorless flakes (ethyl acetate-hexane)

m.p.: 259° C.

Anal. Calcd for C$_{20}$B$_{10}$H$_{37}$O$_3$N: C, 53.67; H, 8.33; N, 3.13. Found C, 53.38; H, 8.10; N, 2.99.

$^1$NMR (CDCl$_3$, 400 MHz) δ 8.12 (2H, d, J=8.3 Hz), 7.66 (2H, d, J=8.3 Hz), 5.60 (1H, s, NH), 2.04 (1H, s, CH), 0.18, 0.11 (each 15H, s, BCH$_3$)

A mixture of 2,3,4,6,6,7,8,9,10,11-decamethyl-1,12-dicarba-closo-dodecaboran-1-yl-isocyanate (40.0 mg, 0.123 mmol) and ethyl 4-aminobenzoate (20.3 mg, 0.123 mmol) was heated at 180° C. for 24 h under argon atmosphere. A crude product was purified by silica gel column chromatography (eluent: 20% ethyl acetate/n-hexane) to give white solid of (2,3,4,5,6,7,8,9,10,11-decamethyl-1,12-dicarba-closo-dodecaboran-1-yl)(4-methoxycarbonylphenyl)urea (30.7 mg, 50.9%). The compound (30.7 mg, 0.063 mmol) was dissolved in ethanol (5 ml), 1N potassium hydroxide solution (1 ml) was added, and heated at 80° C. for 1 h. 2N hydrochloric acid was added, and the mixture was extracted with ethyl acetate. The organic layer was washed with water then saturated brine, dried over magnesium sulfate and the solvent was evaporated to give white solid of (2,3,4,5,6,7, 8,9,10,11-decamethyl-1,12-dicarba-closo-dodecaboran-1-yl)(4-carboxyphenyl)urea (BR638)(28.5 mg, 98.6%).

Colorless flakes (methanol)

m.p.:>300° C.; Anal. Calcd for $C_{20}B_{10}H_{38}O_3N_2$: C, 51.92; H, 8.28; N, 6.06. Found C, 51.63; H, 8.09; N, 5.77.

$^1$H NMR (DMSO-$d_6$, 400 MHz) δ 9.49 (1H, s, NH) 7.92 (2H, d, J=8.8 Hz), 7.48 (2H, d, J=8.8 Hz), 5.57 (1H, s, NH), 2.77 (1H, s, CH), 0.20, 0.14 (each 15H, s, BCH$_3$).

Example 13

To a mixture of methyl 4-(4-bromophenoxy)benzoate (2.0 g, 6.51 mmol), ethynyltrimethylsilane (1.60 g, 16.2 mmol), (PPh$_3$)$_2$PdCl$_2$ (182 mg, 0.259 mmol), and CuI (24.8 mg, 0.130 mmol) in THF (30 ml), diisopropylamine (1.38 g, 13.7 mmol) was added dropwise under argon atmosphere. After the mixture was stirred at 50° C. for 24 h, the mixture was then heated to reflux for 6 h. Water was added to the mixture after cooling, insoluble substance was filtered with Celite, and the filtrate was extracted with ethyl acetate. The organic layer was washed with saturated brine, dried over magnesium sulfate and concentrated. The residue was purified by silica gel column chromatography (eluent: n-hexane/ethyl acetate=30/1) to give methyl 4-(4-trimethylsitylethynylphenoxy)benzoate (63%).

$^1$H-NMR (CDCl$_3$) δ 0.25 (9 H, s), 3.90 (3 H, s), 6.97 (2 H, d, J=8.8 Hz), 6.99 (2H, d, J=9.0 Hz), 7.48 (2 H, d, J=8.8 Hz), 8.01 (2 H, d, J=9.0 Hz).

To a solution of the methyl benzoate described above (1.28 g, 3.95 mmol) in methanol (20 ml), potassium carbonate (546 mg, 3.95 mmol) was added and stirred at room temperature for 1.5 h. After the mixture was concentrated, water was added and extracted with ethyl acetate. The organic layer was washed with saturated brine, dried over magnesium sulfate and concentrated. The residue was purified by silica gel column chromatography (eluent: n-hexane/ethyl acetate=10/1) to give methyl 4-(4-ethynylphenoxy)benzoate (89%).

$^1$H-NMR (CDCl$_3$) δ 3.06 (1 H, s), 3.91 (3 H, s), 6.99 (2 H, d, J=8.8 Hz), 7.01 (2 H, d, J=8.8 Hz), 7.50 (2 H, d, J=8.8 Hz), 8.02 (2 H, d, J=8.8 Hz).

A solution of methyl 4-(4-ethynylphenoxy)benzoate (850 mg, 3.37 mmol) and decaborane (14)(412 mg, 3.37 mmol) in acetonitrile (2.5 ml)-benzene (25 ml) was heated to reflux for 36 h under argon atmosphere. The mixture was concentrated, and the residue was purified by silica gel column chromatography (eluent: n-hexane/ethyl acetate=10/1) to give methyl 4-[4-(1,2-dicarba-closo-dodecaboran-1-yl)phenoxy]-benzoate (66%).

$^1$H-NMR (CDCl$_3$) δ (10 H, br m), 3.91 (4 H, s), 6.97 (2 H, d, J=8.9 Hz), 7.02 (2 H, d, J=8.9 Hz), 7.49 (2 H, d, J=8.9 Hz), 8.04 (2 H, d, J=8.9 Hz).

A solution of methyl 4-(4-ethynylphenoxy)benzoate (150 mg, 0.405 mmol) in DMF (3 ml) was added dropwise to DMF suspension (1 ml) of 60% sodium hydride (19.4 mg, 0.485 mmol), and stirred at room temperature for 5 min. DMF solution (1 ml) of 1-iodopropane (103 mg, 0.606 mmol) was added dropwise, and stirred at room temperature for 1 h. The reaction was quenched by the addition of 2N hydrochloric acid, and the mixture was extracted with diethyl ether. The organic layer was washed with water then saturated brine, dried over sodium sulfate and concentrated. The residue was purified by silica gel column chromatography (eluent: n-hexane/ethyl acetate=10/1) to give methyl 4-[4-(2-n-propyl-1,2-dicarba-closo-dodecaboran-1-yl)-phenoxy]benzoate (44%).

$^1$H-NMR (CDCl$_3$) δ 0.77 (3 H, t, J=7.3 Hz), 1.40–3.40 (10 H, br m), 1.43 (2 H, m), 1.75 (2 H, m), 3.92 (3 H, s), 7.01 (2 H, d, J=9.0 Hz), 7.06 (2 H, d, J=9.0 Hz), 7.61 (2 H, d, J=9.0 Hz), 8.06 (2 H, d, J=9.0 Hz).

To a solution of the benzoate described above (55 mg, 0.133 mmol) in water (1.5 ml)-dioxane (5 ml), concentrated sulfuric acid (1 ml) was added and stirred at 100° C. for 24 h. The mixture was poured into ice water, and extracted with ethyl acetate. The organic layer was washed with saturated brine, dried over sodium sulfate and concentrated to give 4-[4-(2-n-propyl-1,2-dicarba-closo-dodecaboran-1-yl) phenoxy]-benzoic acid (BR503)(95%)

Colorless plates (ethyl acetate/n-hexane)

m.p.

$^1$H-NMR (DMSO-$d_6$) δ 1.40–3.80 (10 H, br m), 2.18 (6 H, s), 2.59 (2 H, t, J=5.8 Hz), 4.02 (2 H, t, J=5.8 Hz), 6.69 (2 H, d, J=8.8 Hz), 6.88 (2 H, d, J=8.8 Hz), 7.27 (2H, d, J=8.8 Hz) 7.37 (2 H, d, J=8.8 Hz), 9.74 (1 H, s)

Anal. Calcd for $C_{18}H_{29}B_{10}NO_2$: C, 54.11; H, 7.32; N, 3.51. Found C, 53.84; H, 7.14; N, 3.21.

To a mixture of methyl 4-(4-bromobenzoyl)benzoate (1.20 g, 3.76 mmol), ethynyltrimethylsilane (554 mg, 5.66 mmol), (PPh$_3$)$_2$PdCl$_2$(106 mg, 0.151 mmol), CuI (14.3 mg, 0.075 mmol) in THF (30 ml), diisopropyl amine (799 mg, 7.92 mmol) was added dropwise under argon atmosphere. The mixture was stirred at 50° C. for 4 h. Water was added to the mixture after cooling, and the mixture was extracted with ethyl acetate. The organic layer was washed with saturated brine, dried over sodium sulfate and concentrated. The residue was purified by silica gel column chromatography (eluent: n-hexane/ethyl acetate=10/1) to give methyl 4-(4-trimethylsilylethynylbenzoyl)benzoate (83%).

$^1$H-NMR (CDCl$_3$) δ 0.28 (9 H, s), 3.97 (3 H, s), 7.57 (2 H, d, J=8.6 Hz), 7.74 (2 H, d, J=8.6 Hz), 7.81 (2 H, d, J=8.6 Hz), 8,15 (2 H, d, J=8.6 Hz).

To a solution of this compound (1.00 g, 2.97 mmol) in methanol (25 ml)/dichloromethane (2.5 ml), potassium carbonate (411 mg, 2.97 mmol) was added and stirred at room temperature for 1 h. Water was added after the mixture was concentrated, and the mixture was extracted with ethyl acetate. The organic layer was washed with saturated brine, dried over sodium sulfate and concentrated to give methyl 4-(4-ethynylbenzoyl)benzoate (100%).

$^1$H-NMR (CDCl$_3$) δ 3.27 (1 H, s), 3.97 (3 H, s), 7.61 (2 H, d, J=8.6 Hz), 7.76 (2 H, d, J=8.6 Hz), 7.82 (2 H, d, J=8.6 Hz), 8.15 (2 H, d, J=8.6 Hz).

A solution of methyl 4-(4-ethynyl benzoyl)benzoate (780 mg, 2.95 mmol) and decaborane (14)(361 mg, 2.95 mmol) in acetonitrile (2.5 ml)/benzene (25 ml) was heated to reflux for 24 h under argon atmosphere. The mixture was concentrated, and the residue was purified by silica gel column chromatography (eluent: n-hexane/ethyl acetate=10/1) to give methyl 4-[4-(1,2-dicarba-closo-dodecaboran-1-yl) benzoyl]-benzoate (58%).

$^1$H-NMR (CDCl$_3$) δ 1.60–3.40 (10 H, br m), 3.97 (3 H, s), 4.03 (1 H, br s), 7.61 (2 H, d, J=8.5 Hz), 7.76 (2 H, d, J=8.5 Hz), 7.82 (2 H, d, J=8.2 Hz), 8.16 (2 H, d, J=8.2 Hz).

60% NaH (43.9 mg, 1.10 mmol) was added at 0° C. to a solution of methyl 4-[4-(1,2-dicarba-closo-dodecaboran-1-yl) benzoyl]benzoate (350 mg, 0.915 mmol) and propyl iodide (233 mg, 1.37 mmol) in DMF (15 ml), and stirred at room temperature for 1 h. The reaction was quenched by the addition of 2N hydrochloric acid, and the mixture was extracted with diethyl ether. The organic layer was washed with saturated brine, dried over sodium sulfate and concentrated. The residue was purified by silica gel column chromatography (eluent: n-hexane/ethyl acetate=20/1) to give methyl 4-[4-(2-n-propyl-1,2-dicarba-closo-dodecaboran-1-yl)benzoyl benzoate (58%).

$^1$H-NMR (CDCls) δ0.75 (3 H, t, J=7.3 Hz), 1.60–3.80 (10 H, br m), 1.44 (2 H, m), 1.75 (2 H, m), 3.98 (3 H, s), 7.77 (2 H, d, J=8.9 Hz), 7.81 (2 H, d, J=8.9 Hz), 7.88 (2 H, d, J=8.6 Hz), 8.17 (2 H, d, J=8.6 Hz);

HRMS Calcd for $C_{20}H_{28}B_{10}O_3$ 424.3042, Found 424.3039

To a solution of 4-[4-(2-n-propyl-1,2-dicarba-closo-dodecaboran-1-yl)benzoyl]-methyl benzoate (50 mg, 0.118 mmol) in water (1.5 ml)/dioxane (5 ml), concentrated sulfuric acid (1 ml) was added and stirred at 100° C. for 24 h. The mixture was poured into ice water, and extracted with ethyl acetate. The organic layer was washed with water then saturated brine, dried over sodium sulfate and concentrated to give 4-[4-(2-n-propyl-1,2-dicarba-closo-dodecaboran-1-yl)benzoyl]benzoic acid (BR513).

Colorless needles (n-hexane/ethyl acetate)

m.p.: 236–237° C.

$^1$H-NMR (DMSO-$d_6$) δ 0.70 (3 H, t, J=7.3 Hz), 1.36 (2 H, m), 1.40–3.40 (10 H, br m), 1.83 (2 H, m), 7.83 (2 H, d, J=8.5 Hz), 7.84 (2 H, d, J=8.2 Hz), 7.91 (2H, d, J=8.5 Hz), 8.10 (2 H, d, J=8.2 Hz), 13.33 (1 H, br).

HRMS Calc for $C_{20}H_{28}B_{10}NO_2$ 408.3092, Found 408.3084

To a solution of methyl 4-[4-(2-n-propyl-1,2-dicarba-closo-dodecaboran-1-yl)-benzoyl]benzoate (75 mg, 0.177 mmol) in THF (2 ml), 2.4 mmol/1 g trimethyltriphenylphosphoniumbromide-sodium amide (370 mg, 0.888 mmol) was added and stirred for 2 h under argon atmosphere. 2N hydrochloric acid was added at 0° C., and the mixture was extracted with ethyl acetate. The organic layer was washed with water then saturated brine, dried over sodium sulfate and concentrated. The residue was purified by silica gel column chromatography (eluent: n-hexane/ethyl acetate=30/1) to give methyl 4-[1-[4-(2-n-propyl-1,2-dicarba -closo-dodecaboran-1-yl)-phenyl]ethenyl]benzoate (25%).

$^1$H-NMR (CDCl$_3$) δ 0.76 (3 H, t, J=7.2 Hz), 1.44 (2 H, m), 1.50–3.60 (10 H, br m), 1.76 (2 H, m), 3.93 (3 H, s), 5.60 (1 H, s), 5.62 (1 H, s), 7.32 (2 H, d, J=8.6 Hz), 7.37 (2 H, d, J=8.4 Hz), 7.59 (2 H, d, J=8.6 Hz), 8.02 (2 H, d, J=8.4 Hz)

HRMS Calcd for $C_{21}H_{30}B_{10}O_2$ 422.3249, Found 422.3278

To a solution of methyl 4-[1-[4-(2-n-propyl-1,2-dicarba-closo-dodecaboran-1-yl)phenyl]ethenyl]benzoate (17 mg, 0.0402 mmol) in water (1.5 ml)/dioxane (5 ml), concentrated sulfuric acid (1 ml) was added and stirred at 100° C. for 24 h. The mixture was poured into ice water, and extracted with ethyl acetate. The organic layer was washed with water then saturated brine, dried over sodium sulfate and concentrated. The residue was purified by silica gel column chromatography (eluent: n-hexane/ethyl acetate=2/1) to give 4-[1-[4-(2-n-propyl-1,2-dicarba-closo-dodecaboran-1-yl) phenyl]ethenyl]benzoic acid (64%).

Colorless needles (n-hexane/ethyl acetate)

m.p.: 152–154° C.

$^1$H-NMR (DMSO-$d_6$) δ 0.71 (3 H, t, J=7.3 Hz), 1.35 (2 H, m), 1.40–3.40 (10 H, br m), 1.81 (2 H, m), 5.68 (1 H, s), 5.71 (1 H, s)7.38 (2 H, d, J=8.5 Hz), 7.40 (2 H, d, J=8.5 Hz), 7.70 (2 H, d, J=8.5 Hz), 7.94 (2 H, d, J=8.5 Hz), 12.98 (1 H, br).

To a solution of methyl 4-[4-(2-n-propyl-1,2-dicarba-closo-dodecaboran-1-yl)benzoyl]benzoate (50 mg, 0.118 mmol) in THF (1 ml)/dichloromethane (1 ml), trimethylsilane (274 mg, 2.36 mmol) was added and stirred at 50 ° C. for 5 h. The mixture was poured into ice water, and extracted with ethyl acetate. The organic layer was washed with water then saturated brine, dried over sodium sulfate and concentrated. The residue was purified by silica gel column chromatography (eluent: n-hexane/ethyl acetate=20/1) to give methyl 4-[4-(2-n-propyl-1,2-dicarba-closo-dodecaboran-1-yl)benzyl]benzoate (90%).

$^1$H-NMR (CDCl$_3$) δ 0.72 (3 H, t, J=7.3 Hz), 1.40 (2 H, m), 1.50–3.60 (10H, br m), 1.71 (2 H, m), 3.90 (3 H, s), 4.04 (2 H, s), 7.17 (2 H, d, J=8.5 Hz), 7.24 (2 H, d, J=8.5 Hz), 7.53 (2 H, d, J=8.5 Hz), 7.98 (2 H, d, J=8.5 Hz)

HRMS Calcd for $C_{20}H_{30}B_{10}O_2$ 410.3249, Found 410.3220

To a solution of methyl 4-[4-(2-n-propyl-1,2-dicarba-closo-dodecaboran-1-yl) benzyl]benzoate (40 mg, 0.0974 mmol) in water (1.5 ml)/dioxane (5 ml), concentrated sulfuric acid (1 ml) was added and stirred at 100° C. for 24 h. The mixture was poured in ice water, and extracted with ethyl acetate. The organic layer was washed with water and saturated brine, dried over sodium sulfate and concentrated to give 4-[4-(2-n-propyl-1,2-dicarba-closo-dodecaboran-1-yl)benzyl]benzoic acid (BR533) (100%).

Colorless prisms (n-hexane/ethyl acetate)

m.p.: 205–206° C.

$^1$H-NMR (DMSO-$d_6$) δ 0.66 (3 H, t, J=7.4 Hz), 1.31 (2 H, m), 1.40–3.40 (10 H, brm), 1.75 (2 H, m), 4.07 (2 H, s),7.33 (2 H, d, J=8.2 Hz), 7.34 (2 H, d, J=8.2 Hz), 7.61 (2 H, d, J=8.2 Hz), 7.86 (2 H, d, J=8.2 Hz), 12.80 (1 H, br).

Anal. Calcd for $C_{19}H_{28}B_{10}O_2$: C, 57.55; H, 7.12. Found C, 57.31; H, 7.09.

Example 14

To a solution of O-methyl-BE100 (300 mg, 1.20 mmol) in benzene (2 ml)/diethyl ethyl (1 ml), 1.53 M n-buLi hexane solution (0.82 ml, 1.25 mmol) was added dropwise at 0° C. under argon atmosphere. After stirring at room temperature for 30 min, a solution of benzoyl peroxide (145 mg, 0.601 mmol) in benzene(2 ml)/diethyl ether (1 ml) was added dropwise at 0° C. Then the mixture was stirred at room temperature for 2 h. The reaction was quenched by the addition of 10% hydrochloric acid solution and the mixture was extracted with ethyl acetate. The organic layer was washed with water then saturated brine, dried over sodium sulfate and concentrated. The residue was purified by silica gel column chromatography (eluent: n-hexane/ethyl acetate=10/1) to give 1-hydroxy-12-(4-methoxyphenyl)-1, 12-dicarba-closo-dodecaborane (O-methyl-BE119) (75%)

$^1$H-NMR (CDCl$_3$) d 1.60–3.40 (10 H, br m), 2.87 (1 H, s), 3.73 (3 H, s), 6.67 (2 H, d, J=8.6 Hz), 7.12 (2 H, d, J=8.6 Hz)

HRMS Calcd for $C_9H_{18}B_{10}O_2$ 266.2310, Found 266.2304

To a solution of O-methyl-BE119 (91 mg, 0.342 mmol) in dichloromethane (3 ml), 1M BBr$_3$ dichloromethane solution (0.855 ml) was added dropwise at −78° C. Then the mixture was stirred at room temperature for 2 h. The mixture was poured into ice water, and extracted with ethyl acetate. The organic layer was washed with saturated brine, dried over sodium sulfate and concentrated to give 1-hydroxy-12-(4-hydroxyphenyl)-1,12-dicarba-closo-dodecaborane (BE 119) (100%).

Colorless needles (dichloromethane/n-hexane)

m.p.: 181–183° C.

$^1$H-NMR (CDCl$_3$) d 1.60–3.40 (10 H, br m), 4.70 (1 H, br), 6.60 (2 H, d, J=8.8 Hz), 7.07 (2H, d, J=8.8 Hz)

HRMS Calcd for C$_8$H$_{16}$B$_{10}$O$_2$ 252.2153, Found 252.2173

Anal. Calcd for C$_8$H$_{16}$B$_{10}$O$_2$.0.5H$_2$O: C, 36.77; H, 6.56. Found C, 36.42; H, 6.57.

To a solution of O-methyl-BE100 (200 mg, 0.799 mmol) in benzene (5 ml)/diethylester (2.5 ml), 1.53M n-BuLi hexane solution (0.623 ml, 0.953 mmol) was added dropwise at 0° C. under argon atmosphere. After stirring at room temperature for 30 min, 2-(2-bromoethoxy) tetrahydro-2H-pyran (231 mg, 1.20 mmol) was added dropwise at 0° C. Then, the mixture was stirred at room temperature for 15 h. The reaction was quenched by the addition of water, and the mixture was extracted with diethyl ether. The organic layer was washed with saturated brine, dried over sodium sulfate and concentrated. The residue was purified by silica gel column chromatography (eluent: n-hexane/dichloromethane=2/1) to give 1-(4-methoxyphenyl)-12-(2-tetrahydropyranyloxyethyl)-1,12-dicarba-closo-dodecaborane (45%).

$^1$H-NMR (CDCl$_3$) d 1.45–1.82 (6 H, m), 1.50–3.20 (10 H, br m), 1.98 (2 H, t, J=7.0 Hz), 3.17 (1 H, dt, J=9.9, 7.6 Hz), 3.45–3.51 (1 H, m), 3.55 (1 H, dt, J=10.1, 7.3 Hz), 3.73 (3 H, s), 3.80 (1 H, m), 4.49.(1 H, m), 6.67 (2 H, d, J=9.2 Hz), 7.10 (2 H, d, J=9.2 Hz).

p-Toluenesulfonic acid hydrate (5.6 mg, 0.0294 mmol) was added to a solution of 1-(4-methoxyphenyl)-12-(2-tetrahydropyranyloxyethyl)-1,12-dicarba-closo-dodecaborane (112 mg, 0.296 mmol) in methanol (3 ml)/dichloromethane (1 ml), and stirred at room temperature for 15 h. The reaction was quenched by the addition of saturated sodium hydrogencarbonate solution, and the mixture was extracted with dichloromethane. The organic layer was washed with water then saturated brine, dried over sodium sulfate and concentrated to give 1-(2-hydroxyethyl)-12-(4-methoxyphenyl)-1,12-dicarba-closo-dodecaborane.

$^1$H-NMR (CDCl$_3$) d 1.50–3.30 (10 H, br m), 1.95 (2 H, t, J=7.0 Hz) 3.48 (2 H, t, J=7.0 Hz), 3.73 (3 H, s), 6.67 (2 H, d, J=9.0 Hz), 7.10 (2 H, d, J=9.0 Hz).

To a solution of 1-(2-hydroxyethyl)-12-(4-(methoxyphenyl)-1,12-dicarba-closo-dodecaborane (80 mg, 0.272 mmol) in dichloromethane (3 ml), 1M BBr$_3$ dichloromethane solution (0.680 ml) was added dropwise at −78° C., then stirred at room temperature for 3 h. The mixture was poured into ice water, and extracted with ethyl acetate. The organic layer was washed with water then saturated brine, dried over sodium sulfate and concentrated. The residue was purified by silica gel column chromatography (eluent: n-hexane/ethyl acetate=10/1) to give 1-(2-hydroxyethyl)-12-(4-(hydroxyphenyl)-1,12-dicarba-closo-dodecaborane (BE122)(88%).

Colorless needles (dichloromethane/n-hexane)

m.p.: 180–181° C.

$^1$H-NMR (CDCl$_3$) d 1.30 (1 H, t, J=5.1 Hz), 1.50–3.30 (10 H, br m), 1.95 (2 H, t, J=7.0 Hz) 3.48 (2 H, dt, J=5.1, 7.0 Hz), 4.75 (1 H, s), 6.60 (2 H, d, J=9.0 Hz), 7.06 (2 H, d, J=9.0 Hz)

HRMS Calcd for C$_{10}$H$_{20}$B$_{10}$O$_2$ 280.2466, Found 280.2462

Anal. Calcd for C$_{10}$H20B$_{10}$O$_2$: C, 42.84; H, 7.19. Found C, 42.79; H, 7.46.

To a solution of O-methyl-BE100 (750 mg, 3.00 mmol) in benzene (10 ml)/diethyl ether (5 ml), 1.53 M n-BuLi hexane solution (2.35 ml, 3.60 mmol) was added dropwise at 0° C. under argon atmosphere. After stirring at 30° C. for 30 min, 2-(3-bromopropyloxy) tetrahydro-2H-pyran (746 mg, 3.60 mmol) was added dropwise at 0° C. Then the mixture was stirred at room temperature for 18 h. The reaction was quenched by the addition of water, and the mixture was extracted with diethyl ether. The organic layer was washed with saturated brine, dried over sodium sulfate and concentrated. The residue was purified by silica gel column chromatography (eluent: n-hexane/dichloromethane) to give 1-(4-methoxyphenyl)-12-(3-tetrahydropyranyloxy-n-propyl)-1,12-dicarba-closo-dodecaborane (69%). To a methanol solution of this compound (705 mg, 1.80 mmol), p-toluene sulfonic acid hydrate (34.2 mg, 0.180 mmol) was added, and stirred at room temperature for 15 h. The reaction was quenched by the addition of saturated sodium hydrogencarbonate solution, and the mixture was extracted with dichloromethane. The organic layer was washed with water then saturated brine, dried over sodium sulfate and concentrated to give 1-(3-hydroxypropyl)-12-(4-methoxyphenyl)-1,12-dicarba-closo-dodecaborane (93%).

$^1$H-NMR (CDCl$_3$) d 1.17 (1 H, br s) 1.40–3.30 (10 H, br m), 1.46 (2 H, m), 1.78 (2 H, m) 3.50 (2 H, m), 3.73 (3 H, s), 6.67 (2 H, d, J=9.0 Hz), 7.10 (2 H, d, J=9.0 Hz).

To a solution of 1-(3-hydroxypropyl)-12-(4-methoxyphenyl)-1,12-dicarba-closo-dodecaborane (80 mg, 0.259 mmol) in dichloromethane (3 ml), 1M BBr$_3$ dichloromethane solution (0.648 ml) was added dropwise at −78° C. Then the mixture was stirred at room temperature for 3 h. The mixture was poured into ice water and extracted with ethyl acetate. The organic layer was washed with saturated brine, dried over sodium sulfate and concentrated. The residue was purified by silica gel column chromatography (eluent: n-hexane/ethyl acetate=4/1) to give 1-(3-hydroxypropyl)-12-(4-hydroxyphenyl)-1,12-dicarba-closo-dodecaborane (BE123) (92%).

Colorless needles (dichloromethane/n-hexane)

m.p.: 185–187° C.

$^1$H-NMR (CDCl$_3$) d 1.10–3.30 (10 H, br m), 1.45 (2 H, m), 1.77 (2 H, m), 3.50 (2 H, t, J=6.1 Hz), 4.70 (1 H, br s), 6.60 (2 H, d, J=8.8 Hz), 7.06 (2 H, d, J=8.5 Hz)

Anal. Calcd for C$_{11}$H$_{22}$B$_{10}$O$_2$: C, 44.88; H, 7.53. Found C, 44.58; H, 7.32.

O-Methyl-BE200 was converted to 1-hydroxy-7-(4-hydroxyphenyl)-1,7-dicarba-closo-dodecaborane (BE219) by a similar procedure that used for BE119.

Colorless needles (dichloromethane/n-hexane)

m.p.: 168–169° C.

$^1$H-NMR (CDCl$_3$) d 1.40–4.00 (10 H, br m), 4.80 (1 H, br), 6.70 (2 H, d, J=9.0 Hz), 7. 28 (2 H, d, J=9.0 Hz)

Anal. Calcd for C$_8$H$_{16}$B$_{10}$O$_2$: C, 38.08; H, 6.39. Found C, 37.84; H, 6.30.

O-Methyl-BE200 was converted to 1-(2-hydroxyethyl)-7-(4-hydroxyphenyl)-1,7-dicarba-closo-dodecaborane (BE222) by a similar procedure that used for BE122..

Colorless needles (dichloromethane/n-hexane)

m.p.: 156–157° C.

$^1$H-NMR (CDCl$_3$) d 1.50–3.50 (10 H, br m), 2.28 (2 H, t, J=6.9 Hz) 3.67 (2 H, t, J=6.9, Hz), 4.79 (1 H, s), 6.69 (2 H, d, J=8.9 Hz), 7.28 (2 H, d, J=8.9 Hz)

HRMS Calcd for C$_{10}$H$_{20}$B$_{10}$O$_2$ 280.2466, Found 280.2470

Anal. Calcd for C$_{10}$H$_{20}$B$_{10}$O$_2$: C, 42.84; H, 7.19. Found C, 42.53; H, 6.75.

O-Methyl-BE200 was converted to 1-(3-hydroxypropyl)-7-(4-hydroxyphenyl)-1,7-dicarba-closo-dodecaborane (BE323) by a similar procedure that used for BE123.

Colorless needles (dichloromethane/n-hexane)

m.p.:157–158° C.

$^1$H-NMR (CDCl$_3$) d 1.23 (1 H, t, J=5.1 Hz), 1.40–3.80 (10 H, br m), 1.67 (2 H, m), 2.11 (2 H, m) 3.60 (2 H, dt, J=5.1, 5.3 Hz), 4.81 (1 H, s), 6.68 (2 H, d, J=8.9 Hz), 7.28 (2 H, d, J=8.9 Hz)

Anal. Calcd for $C_{11}H_{22}B_{10}O_2$: C, 44.88; H, 7.53. Found C, 44.61; H, 7.24.

1,12-Dicarba-closo-dodecaborane was converted to 1-(3-hydroxyphenyl)-1,12-dicarba-closo-dodecaborane (BE300) via O-methyl-BE300 by a similar procedure that used for BE 100.

Colorless needles (dichloromethane/n-hexane)

m.p.: 163–164° C.

$^1$H-NMR (CDCl$_3$) d 1.50–3.30 (10 H, br m), 2.78 (1 H, br s), 4.67 (1 H, s), 6.66–6.69 (2 H, m), 6.78 (1 H, m), 7.03 (1 H, m)

Anal Calcd for $C_8H_{16}B_{10}O$: C, 40.66; H, 6.82. Found C, 40.36; H, 6.64.

O-Methyl-BE300 was converted to 1-hydroxy-12-(3-hydroxy phenyl)-1,12-dicarba-closo-dodecaborane(BE319) by a similar procedure that used for BE119.

Colorless needles (dichloromethane/n-hexane)

m.p.: 185–186° C.

$^1$H-NMR (CDCl$_3$) d 1.50–3.40 (10 H, br m), 4.70 (1 H, br), 6.66–6.71 (2 H, m), 6.78 (1 H, br d) 7.02 (1 H, t, J=8.0 Hz)

Anal. Calcd for $C_8H_{16}B_{10}O_2$: C, 38.08; H, 6.39. Found C, 38.31; H, 6.43.

O-Methyl-BE300 was converted to 1-(2-hydroxymethyl)-12-(3-hydroxyphenyl)-1,12-dicarba-closo-dodecaborane (BE320) by a similar procedure that used for BE120.

Colorless needles (dichloromethane/n-hexane)

m.p.: 134–135° C.

$^1$H-NMR (CDCl$_3$) d 1.50–3.30 (10 H, br m), 1.58 (1 H, t, J=7.3 Hz), 3.55 (2 H, d, J=7.3 Hz), 4.70 (1 H, s), 6.67–6.69 (2 H, m), 6.77 (1 H, m), 7.03 (1 H, m)

Anal. Calcd for $C_9H_{18}B_{10}O_2$.0.2 H$_2$O: C, 40.04; H, 6.87. Found C, 39.98; H, 6.57.

O-Methyl-BE300 was converted to 1-(2-hydroxyethyl)-12-(3-hydroxyphenyl)-1,12-dicarba-closo-dodecaborane (BE322) by a similar procedure that used for BE122.

Colorless needles (dichloromethane)

m.p.: 186–187° C.

$^1$H-NMR (CDCl$_3$) d 1.30 (1 H, t, J=4.9 Hz), 1.50–3.30 (10 H, br m), 1.95 (2 H, t, J=7.0 Hz) 3.48 (2 H, dt, J=4.9, 7.0 Hz), 4.74 (1 H, s), 6.65–6.69 (2 H, m), 6.76 (1H, m), 7.02 (1 H, m)

Anal. Calcd for $C_{10}H_{20}B_{10}O_2$.0.2H$_2$O: C, 42.29; H, 7.24. Found C, 42.12; H, 6.95.

O-Methyl-BE300 was converted to 1-(3-hydroxypropyl)-12-(3-hydroxyphenyl)-1,12-dicarba-closo-dodecaborane (BE323) by a similar procedure that used for BE 123.

Colorless needles (dichloromethane)

m.p.: 211–212° C.

$^1$H-NMR (DMSO-d$_6$) d 1.25 (2 H, m), 1.40–3.20 (10 H, br m), 1.73 (2 H, m) 3.23 (2 H, dt, J=5.1,5.7 Hz), 4.39 (1 H, t, J=5.1 Hz), 6.57–6.59 (2 H, m), 6.64 (1H,m), 7.01 (1 H, m), 9.54 (1 H, s)

Anal. Calcd for $C_{11}H_{22}B_{10}O_2$.0.1H$_2$O: C, 44.60; H, 7.55. Found C, 44.30; H, 7.28.

1,7-Dicarba-closo-dodecaborane was converted to 1-(3-hydroxyphenyl)-1,7-dicarba-closo-dodecaborane (BE400) via O-methyl-BE400 by a similar procedure that used for BE100.

Colorless needles (dichloromethane/n-hexane)

m.p.: 140–141° C.

$^1$H-NMR (CDCl$_3$) d 1.40–3.80 (10 H, br m), 3.05 (1 H, br s), 4.70 (1 H, s), 6.75 (1 H, dd, J=2.6, 8.1 Hz), 6.90 (1 H, t, J=2.2 Hz), 6.99 (1 H, br d, J=8.1 Hz), 7.11 (1 H, t, J=8.1 Hz)

Anal. Calcd for $C_8H_{16}B_{10}O$: C, 40.66; H, 6.82. Found C, 40.48; H, 6.56.

O-Methyl-BE400 was converted to 1-hydroxy-7-(3-hydroxyphenyl)-1,7-dicarba-closo-dodecaborane (BE419) by a similar procedure that used for BE119.

Colorless needles (dichloromethane/n-hexane)

m.p.: 135–136° C.

$^1$H-NMR (CDCl$_3$) d 1.40–4.00 (10 H, br m), 4.70 (1 H, br), 6.76 (1 H, ddd, J=1.0, 2.5, 8.1 Hz), 6.89 (1 H, t, J=2.5 Hz), 6.99 (1 H, ddd, J=1.0, 2.5, 8.1 Hz), 7.12 (1 H, t, J=8.1 Hz)

Anal. Calcd for $C_8H_{16}B_{10}O_2$: C, 38.08; H, 6.39. Found C, 37.79; H, 6.37.

O-Methyl-BE400 was converted to 1-(2-hydroxymethyl)-7-(3-hydroxyphenyl)-1,7-dicarba-closo-dodecaborane (BE420) by a similar procedure that used for BE120.

Colorless needles (dichloromethane/n-hexane)

m.p.: 140–141° C.

$^1$H-NMR (CDCl$_3$) d 1.50–3.80 (10 H, br m), 1.91 (1 H, t, J=7.2 Hz), 3.87 (2 H, d, J=7.2 Hz), 4.90 (1 H, s), 6.76 (1 H, ddd, J=0.9, 2.2,8.0 Hz), 6.91 (1 H, t, J=2.2 Hz), 6.99 (1 H, ddd, J=0.9, 2.2, 8.0 Hz), 7.11 (1 H, t, J=8.0 Hz)

Anal Calcd for $C_9H_{18}B_{10}O_2$: C, 40.59; H, 6.81. Found C, 40.33; H, 6.81.

O-Methyl-BE400 was converted to 1-(2-hydroxyethyl)-7-(3-hydroxyphenyl)-1,7-dicarba-closo-dodecaborane (BE422) by a similar procedure that used for BE122.

Colorless needles (dichloromethane/n-hexane)

m.p.: 126–127° C.

$^1$H-NMR (CDCl$_3$) d 1.42 (1 H, t, J=5.5 Hz), 1.30–3.60 (10 H, br m), 2.28 (2 H, t, J=6.5 Hz) 3.68 (2 H, dt, J=5.5, 6.5 Hz), 4.84 (1 H, s), 6.75 (1 H, ddd, J=0.9, 2.1, 7.9 Hz), 6.89 (1 H, t, J=2.1 Hz), 6.98 (1 H, ddd, J=0.9, 2.1, 7.9 Hz), 7.11 (1 H, t, J=7.9 Hz)

Anal. Calcd for $C_{10}H_{20}B_{10}O_2$: C, 42.84; H, 7.19. Found C, 42.65; H, 6.90.

O-Methyl-BE400 was converted to 1-(3-hydroxypropyl)-7-(3-hydroxyphenyl)-1,7-dicarba-closo-dodecaborane (BE423) by a similar procedure that used for BE123.

Colorless needles (dichloromethane/n-hexane)

m.p.: 106–107° C.

$^1$H-NMR (CDCl$_3$) d 1.26 (1 H, t, J=5.1 Hz), 1.50–3.70 (10 H, br m), 1.67 (2 H, m), 2.11 (2 H, m), 3.60 (2 H, dt, J=5.1, 5.6 Hz), 4.87 (1 H, s), 6.75 (1 H, ddd, J=0.7, 2.1, 8.1 Hz), 6.90 (1 H, t, J=2.1 Hz), 6.98 (1 H, ddd, J=0.7, 2.1, 8.1 Hz), 7.11 (1 H, t, J=8.1 Hz)

Anal. Calcd for $C_{11}H_{22}B_{10}O_2$: C, 44.88; H, 7.53. Found C, 44.58; H, 7.35.

Potassium carbonate (97.8 mg, 0.708 mmol) was added to a DMF solution of 1,12-bis (4-hydroxyphenyl)-1,12-dicarba-closo-dodecaborane (BE 160)(155 mg, 0.472 mmol)

and (CH$_3$)$_2$NCH$_2$CH$_2$Cl.HCl (68.0 mg, 0.472 mmol), and stirred at 65° C. for 22 h. The reaction was quenched by the addition of water, and the mixture was extracted with ethyl acetate. The organic layer was washed with water then saturated brine, dried over sodium sulfate and concentrated. The residue was purified by silica gel column chromatography (eluent: chloroform/methanol=10/1) to give 1-(4-hydroxyphenyl)-12-(4-dimethylaminoethoxyphenyl)-1,12-dicarba-closo-dodecaborane (BE162)(34%).

Colorless prisms (ethyl acetate/n-hexane)

m.p.: 233–235° C.

$^1$H-NMR (DMSO-d$_6$) δ 1.60–3.40 (10 H, br m), 2.17 (6 H, s), 2.56 (2 H, t, J=5.8 Hz), 3.98 (2 H, t, J=5.8 Hz), 6.61 (2 H, d, J=8.8 Hz), 6.79 (2 H, d, J=9.0 Hz), 7.00 (2 H, d, J=8.8 Hz) 7.11 (2 H, d, J=9.0 Hz), 9.65 (1 H, s)

Anal. Calcd for C$_{18}$H$_{29}$B$_{10}$NO$_2$: C, 54.11; H, 7.32; N, 3.51. Found C, 54.01; H, 7.22; N, 3.36.

1-12-Bis(3-hydroxyphenyl)-1,12-dicarba-closo-decaborane was converted to 1-(2-hydroxyphenyl)-12-(3-dimethylaminoethoxyphenyl)-1,12-dicarba-closo-dodecaborane (BE 172) by a similar procedure that used for BE 162.

Colorless needles (dichloromethane/n-hexane)

m.p.: 183–185° C.

$^1$H-NMR (DMSO-d$_6$) δ 1.70–3.50 (10 H, br m), 2.19 (6 H, s), 2.57 (2 H, t, J=5.8 Hz), 3.99 (2 H, t, J=5.8 Hz), 6.63–6.64 (2 H, m), 6.67–6.68 (2 H, m), 6.79 (1 H, br d, J=7.7 Hz) 6.90 (1 H, dd, J=2.4,8.2 Hz), 7.04 (1 H, m), 7.17 (1 H, t, J=8.2 Hz), 9.59 (1 H, s)

Anal. Calcd for C$_{18}$H$_{29}$B$_{10}$NO$_2$0.2H$_2$O: C, 53.63; H, 7.35; N, 3.47. Found C, 53.56; H, 7.30; N, 3.36.

1,7-Bis(4-hydroxyphenyl)-1,7-dicarba-closo-dodecaborane was converted to 1-(4-hydroxyphenyl)-7-(4-dimethylaminoethoxyphenyl)-1,7-dicarba-closo-dodecaborane (BE262) by a similar procedure that used for BE162.

Colorless prisms (dichloromethane/n-hexane)

m.p.: 166–167° C.

$^1$H-NMR (DMSO-d$_6$) δ 1.40–3.80 (10 H, br m), 2.18 (6 H, s), 2.59 (2 H, t, J=5.8 Hz), 4.02 (2 H, t, J=5.8 Hz), 6.69 (2 H, d, J=8.8 Hz), 6.88 (2 H, d, J=8.8 Hz), 7.27 (2 H, d, J=8.8 Hz) 7.37 (2 H, d, J=8.8 Hz), 9.74 (1 H, s)

Anal. Calcd for C$_{18}$H$_{29}$B$_{10}$NO$_2$: C, 54.11; H, 7.32; N, 3.51. Found C, 53.84; H, 7.14; N, 3.21.

1,7-Bis(3-hydroxyphenyl)-1,7-dicarba-closo-dodecaborane was converted to 1-(3-hydroxyphenyl)-7-(3-dimethylaminoethoxyphenyl)-1,7-dicarba-closo-dodecaborane (BE272) by a similar procedure that used for BE162.

Colorless prisms (dichloromethane/n-hexane)

m.p.: 129–131° C.

$^1$H-NMR (DMSO-d$_6$) δ 1.40–3.80 (10 H, br m), 2.20 (6 H, s), 2.59 (2 H, t, J=5.8 Hz), 4.04 (2 H, t, J=5.8 Hz), 6.76 (1 H, dd, J=2.3,8.0 Hz), 6.88–6.94 (3 H, m), 6.98 (1 H, dd, J=2.6,8.0 Hz), 7.06 (1 H, br d, J=8.0 Hz), 7.13 (1 H, t, J=8.0 Hz), 7.26 (1 H, t, J=8.0 Hz), 9.68 (1 H, s)

Anal. Calcd for C$_{18}$H$_{29}$B$_{10}$NO$_2$: C, 54.11; H, 7.32; N, 3.51. Found C, 53.85; H, 7.17; N, 3.52.

To a mixture of 4-ethynylanisole (700 mg, 5.30 mmol), 4-iodoanisole (1.30 g, 5.55 mmol), (PPh$_3$)$_2$PdCl$_2$ (74.4 mg, 0.106 mmol), and CuI (10.1 mg, 0.053 mmol) in THF (7 ml), diisopropyl amine (1.13 g, 11.1 mmol) was added dropwise under ice cooling under argon atmosphere. After stirring at room temperature for 1 h, water was added, and the mixture was extracted with ethyl acetate. The organic layer was washed with water then saturated brine, dried over sodium sulfate and concentrated. The residue was purified by silica gel column chromatography (eluent: n-hexane/ethyl acetate=15/1) to give bis(4-methoxyphenyl)ethyne (95%).

$^1$H-NMR (CDCl$_3$) d 3.82 (6 H, m), 6.86 (4 H, d, J=8.9 Hz), 7.44 (4 H, d, J=8.9 Hz

A mixture of bis(4-methoxyphenyl) ethyne(700 mg, 2.94 mmol) and decaborane (14) (359 mg, 2.94 mmol) in acetonitrile (2 ml)/benzene (20 ml) was heated to reflux for 28 h under argon atmosphere. After cooling, methanol (20 ml) was added, and the mixture was stirred at room temperature for 12 h. Then, the mixture was concentrated, and the residue was purified by silica gel column chromatography (eluent: n-hexane/ethyl acetate=8/1) to give 1,2-bis(4-methoxyphenyl)-1,2-dicarba-closo-dodecaborane (31%).

$^1$H-NMR (CDCl$_3$) d 1.50–3.90 (10 H, br m), 3.72 (6 H, s), 6.63 (4 H, d, J=9.1 Hz), 7.34 (4 H, d, J=9.1 Hz)

To a solution of 1,2-bis(4-methoxyphenyl)-1,2-dicarba-closo-decaborane (293 mg, 0.882 mmol) in dichloromethane (10 ml), 1M BBr$_3$ dichloromethane solution (4.12 ml) was added dropwise at −78° C. Then, the mixture was stirred at room temperature for 4 h, poured into ice water, and extracted with ethyl acetate. The organic layer was washed with water then saturated brine, dried over sodium sulfate and concentrated. The residue was purified by silica gel column chromatography (eluent: n-hexane/ethyl acetate=3/1) to give 1,2-bis(4-hydroxyphenyl)-1,2-dicarba-closo-dodecaborane (100%).

Colorless prisms (n-hexane/ethyl acetate)

m.p.: 179–181° C.

$^1$H-NMR (DMSO-d$_6$) δ 1.40–3.80 (10 H, br m), 6.57 (4 H, d, J=8.8 Hz), 7.27 (4 H, d, J=8.8 Hz) 9.91 (2 H, s)

Anal Calcd for C$_{14}$H$_{20}$B$_{10}$O$_2$: C, 51.20; H, 6.14. Found C, 50.96; H, 6.15.

To a solution of 1,2-bis(4-hydroxyphenyl)-1,2-dicarba-closo-dodecaborane (150 mg, 0.457 mmol) and (CH$_3$)$_2$NCH$_2$CH$_2$Cl.HCl (65.8 mg, 0.457 mmol) in DMF, potassium carbonate (94.7 mg, 0.685 mmol) was added, and stirred at 65° C. for 20 h. Water was added, and the mixture was extracted with ethyl acetate. The organic layer was washed with water then saturated brine, dried over sodium sulfate and concentrated. The residue was purified by silica gel column chromatography (eluent: chloroform/methanol= 30/1→10/1) to give 1-(4-hydroxyphenyl)-2(4-dimethylamino-ethoxyphenyl)-1,2-dicarba-closo-dodecaborane (BE362)(16%).

Colorless needles (dichloromethane/n-hexane).

m.p.: 177–179° C.

$^1$H-NMR (DMSO-d$_6$) δ 1.50–3.60 (10 H, br m), 2.15 (6 H, s), 2.53 (2 H, t, J=5.9 Hz), 3.96 (2 H, t, J=5.9 Hz), 6.57 (2 H, d, J=8.6 Hz), 6.77 (2 H, d, J=8.6 Hz), 7.29 (2 H, d, J=8.6 Hz) 7.38 (2 H, d, J=8.6 Hz), 9.92 (1 H, s)

Anal. Calcd for C$_{18}$H$_{29}$B$_{10}$NO$_2$.0.2H$_2$O: C, 53.63; H, 7.35; N, 3.47. Found C, 53.45; H, 7.22; N, 3.27.

To a mixed solution of 3-ethynylanisole (347.0 mg, 2.63 mmol), 3-iodoanisole (670.0 mg, 2.86 mmol, 1.1 eq), (PPh$_3$)$_2$PdCl$_2$ (37.2 mg, 0.0530 mmol, 0.02 eq), CuI (5.1 mg, 0.0268 mmol, 0.01 eq) in THF (5 ml), diisopropylamine (0.57 g, 5.63 mmol, 2.1 eq) was added at 0° C., and stirred at room temperature for 1 h. Water was added to the reaction mixture, and the mixture was extracted with ethyl acetate. The organic layer was washed with saturated brine, dried over sodium sulfate and concentrated. The residue was purified by silica gel column chromatography (eluent: ethyl acetate/n-hexane=1/15) to give bis(3-methoxyphenyl) ethyne (594.4 mg, 95.0%).

Light yellow prisms (n-hexane)

m.p.: 61–62° C.

$^1$H-NMR (CDCl$_3$) d3.83 (6 H, s), 6.89 (2 H, ddd, J=1.0, 2.6,8.3 Hz), 7.06 (2 H, dd, J=1.3,2.6 Hz,), 7.13 (2 H, dt, J=1.2,7.7 Hz), 7.25 (2 H, t, J=8.0 Hz)

Anal. Calcd for $C_{16}H_{14}O_2$: C, 80.65; H, 5.92. Found C, 80.49; H, 6.01

HRMS Cacld for $C_{16}H_{14}O_2$ 238.0994, Found 238.1002

A solution of bis(3-methoxyphenyl)ethyne (501.6 mg, 2.10 mmol), decaborane (14)(258.1 mg, 2.11 mmol) in benzene (15 ml), and acetonitrile (1.5 ml) was refluxed for 46 h under argon atmosphere. After cooling to room temperature, the reaction mixture was diluted with methanol, stirred for 1 h and concentrated. The residue was purified by silica gel column chromatography (eluent: ethyl acetate/n-hexane)=1/8) to give 1,2-bis (3-methoxyphenyl)-1,2-dicarba-closo-dodecaborane (367.9 mg, 49.0%).

Colorless prisms (dichloromethane/n-hexane)

m.p.: 116–118° C.

$^1$H-NMR (CDCl$_3$) d1.7–3.6 (10 H, br m), 3.68 (6 H, s), 6.77 (2 H, ddd, J=1.8,2.3,7.5 Hz), 6.96 (2 H, t, J=2.0 Hz), 7.03(2 H, dt, J=1.8,7.9 Hz), 7.06 (2 H, t, J=7.6 Hz)

Anal. Calcd for $C_{16}H_{24}B_{10}O_2$: C, 53.91; H, 6.79. Found C, 3.61; H, 6.75.

HRMS Calcd for $C_{16}H_{24}{}^{10}B_2{}^{11}B_8O_2$ 366.2779, Found 356.2782

1,2-Bis(3-methoxyphenyl)-1,2-dicarba-closo-dodecaborane (317.7 mg, 0.891 mmol) was dissolved in dichloromethane (3 ml), cooled to −78° C., BBrs (1-dichloromethane solution) (2.67 ml, 2.67 mmol, 3 eq) was added to the solution and the mixture was stirred at room temperature for 1 h. The mixture was poured ino ice water, and the organic layer was washed with saturated brine, dried over sodium sulfate and concentrated. The residue was purified by silica gel column chromatography (eluent: ethyl acetate/n-hexane=1/1) to give 1,2-bis(3-hydroxyphenyl)-1,2-dicarba-closo-dodecaborane (BE370) (297.4 mg, 100%).

Colorless needles (dichloromethane/n-hexane)

m.p.: 202–203° C.

$^1$H-NMR (CDCl$_3$) d1.7–3.6 (10 H, br m), 4.90 (2 H, br s), 6.71 (2 H, m), 6.93 (2 H, t, J=1.3 Hz), 7.00 (2 H, m), 7.02 (2 H, t, J=7.6 Hz)

Anal. Calcd for $C_{14}H_{20}B_{10}O_2 \cdot 1/6H_2O$: C, 50.74; H, 6.18. Found C, 50.75; H, 6.14.

HRMS Calcd for $C_{14}H_{20}{}^{10}B_2{}^{11}B_8O_2$ 328.2466, Found 328.2436

To a solution of 1,2-bis(3-hydroxyphenyl)-1,2-dicarba-closo-dodecaborane (210.9 mg, 0.642 mmol) in DMF (7 ml), (CH$_3$)$_2$NCH$_2$CH$_2$Cl.HCl (92.5 mg, 0.642 mmol, 1 eq) and potassium carbonate (133.1 mg, 0.963 mmol, 1.5 eq) were added, and stirred at 65° C. for 24 h. Water was added to the reaction mixture, and the mixture was extracted with ethyl acetate. The organic layer was washed with saturated brine, dried over sodium sulfate and concentrated. The residue was purified by silica gel column chromatography (eluent: dichloromethane/methanol=10/1) to give 1-(3-hydroxyphenyl)-2-(3-dimethylaminoethoxyphenyl)-1,2-dicarba-closo-dodecaborane (BE372) (9.0 mg, 4%).

Colorless prisms (dichloromethane/n-hexane)

m.p.: 192–193° C.

$^1$H-NMR (DMSO-d$_6$) δ 1.6–3.5 (10 H, br m), 2.16 (6 H, s), 2.52 (2 H, t, J=5.7 Hz), 3.93 (2 H, t, J=5.9 Hz), 6.71 (1 H, d, J=7.9 Hz), 6.93 (4 H, m), 7.03 (1 H, t, J=8.0 Hz), 7.08 (1 H, d, J=8.1 Hz), 7.16 (1 H, t, J=8.1 Hz), 9.69 (1 H, br s)

HRMS Calcd for $C_{18}H_{29}{}^{10}B_2{}^{11}B_8NO_2$ 399.3201, Found 399.3209

Example 16

To a solution of 1-(4-methoxyphenyl)-1,7-dicarba-closo-dodecaborane (O-methyl-BE200) (550 mg, 2.20 mmol) in benzene (10 ml)-diethyl ether (5 ml), n-BuLi (1.57 M in hexane)(2.10 ml, 3.30 mmol, 1.5 eq) was added at 0° C. under argon atmosphere, then the mixture was stirred at room temperature for 30 min. After the treatment, 2-(11-bromo-n-undecanoyloxy) tetrahydro-2H-pyran (736.7 mg, 2.20 mmol, 1 eq) was added at 0° C., then stirred at room temperature for 20 h. Water was added to the mixture, and the mixture was extracted with ethyl acetate. The organic layer was washed with saturated brine, dried over magnesium sulfate and concentrated. The residue was purified by silica gel column chromatography (eluent: ethyl acetate/n-hexane=1/30) to give 1-(4-methoxyphenyl)-7-(11-tetrahydroxypyranyloxy-n-undecane-1-yl)-1,7-dicarba-closo-dodecaborane.(360.3 mg, 32.5%).

$^1$H-NMR (CDCl$_3$) d1.15–1.42 (16 H, m), 1.48–1.63 (6 H, m), 1.6–3.1 (10 H, br m), 1.71 (1 H, m), 1.82 (1 H, m), 1.96 (2 H, m), 3.38 (1 H, dt, J=6.6,9.5 Hz), 3.50 (1 H, m), 3.73 (1 H, dt, J=6.6,9.5 Hz), 3.77 (3 H, s), 3.87 (1 H, m), 4.57 (1 H, m), 6.75 (2 H, d, J=9.1 Hz), 7.32 (2 H, d, J=9.1 Hz)

1-(4-Methoxyphenyl)-7-(11-tetrahydropyranyloxy-n-undecane-1-yl)-1,7-dicarba-closo-dodecaborane (710 mg, 1.41 mmol) was dissolved in methanol (6 ml), p-toluene sulfonic acid hydrate (26.8 mg, 0.141 mmol, 0.1 eq) was added, and stirred at room temperature for 12 h. Saturated sodium hydrogencarbonate solution was added the mixture, and the mixture was extracted with dichloromethane. The organic layer was washed with saturated brine, dried over magnesium sulfate and concentrated. The residue was purified by silica gel column chromatography (eluent: dichloromethane/n-hexane=2/1) to give 1-(4-methoxyphenyl)-7-(11-hydroxy-n-undecane-1-yl)-1,7-dicarba-closo-dodecaborane (512.5 mg, 86.6%)

$^1$H-NMR (CDCl$_3$) d 1.15–1.42 (16 H, m), 1.20 (1 H, t, J=5.4 Hz), 1.50–1.61 (2 H, m), 1.6–3.1 (10 H, br m), 1.96 (2 H, m), 3.64 (2 H, td, J=5.5,6.5 Hz), 3.77 (3 H, s), 6.75 (2 H, d, J=9.0 Hz), 7.32 (2 H, d, J=9.0 Hz)

HRMS Calcd for $C_{20}H_{40}{}^{10}B2{}^{11}B_8O_2$ 420.4031, Found 420.4043

1-(4-Methoxyphenyl)-7-(11-hydroxy-n-undecane-1-yl)-1,7-dicarba-closo-dodecaborane (512.5 mg, 1.22 mmol) was dissolved in acetone (3 ml), CrO$_3$ (609.9 mg, 6.10 mmol, 5 eq)/20%sulfuric acid solution (3 ml) was added at 0° C., then stirred at room temperature for 3 h. The mixture was poured into ice water, and extracted with ethyl acetate. The organic layer was washed with saturated brine, dried over magnesium sulfate and concentrated. The residue was purified by silica gel column chromatography (eluent: ethyl acetate/n-hexane-1/2→chloroform/methanol=30/1) to give 11-{1-(4-methoxyphenyl)-1,7-dicarba-closo-dodecaboran-7-yl}-n-undecanoic acid 1-(4-methoxyphenyl)-7-(11-hydroxy-n-undecane-1-yl)-1,7-dicarba-closo-dodecaboranyl ester (295.5 mg, 57.9%) and 11-[1-(4-methoxy phenyl)-1,7-dicarba-closo-dodecaboran-7-yl]-n-undecanoic acid (54.0 mg, 10.2%). The ester was converted to the carboxylic acid by hydrolysis with sulfuric acid in dioxane (yield 24%)

$^1$H-NMR (CDCl$_3$) d 1.15–1.42 (14 H, m), 1.6–3.1 (10 H, br m), 1.63 (2 H, m), 1.96 (2 H, m), 2.35 (2 H, t, J=8.6 Hz), 3.77 (3 H, s), 6.75 (2 H, d, J=9.0 Hz), 7.32 (2 H, d, J=9.0 Hz)

11-[1-(4-Methoxyphenyl)-1,7-dicarba-closo-dodecaboran-7-yl]-n-undecanoic acid (100.0 mg, 0.230 mmol) was dissolved in dichloromethane (1 ml), cooled to −78° C., BBr$_3$ (1.0 M dichloromethane solution) (0.6 ml, 0.6 mmol, 2.6 eq) was added, and stirred at room temperature for 2 h. The mixture was poured in ice water, and extracted with ethyl acetate. The organic layer was washed with saturated brine, dried over magnesium sulfate and concentrated. The residue was purified by silica gel column chromatography (eluent: ethyl acetate/n-hexane=1/1) to give 11-[1-(4-hydroxyphenyl)-1,7-dicarba-closo-dodecaboran-7-yl]-n-undecanoic acid (69.0 mg, 71.3%).

$^1$H-NMR (CDCl$_3$) d1.15–1.42 (14 H, m), 1.6–3.1 (10 H, br m), 1.63 (2 H, quint, J=7.5 Hz), 1.96 (2 H, m), 2.35 (2 H, t, J=7.5 Hz), 6.69 (2 H, d, J=9.0 Hz), 7.28 (2 H, d, J=9.0 Hz)

HRMS Calcd for C$_{19}$H$_{36}$$^{10}$B$_2$$^{11}$B$_8$O$_3$ 420.3668, Found 420.3673

To a solution of 11-[1-(4-hydroxyphenyl)-1,7-dicarba-closo-dodecaboran-7-yl]-n-undecanoic acid (56.5 mg, 0.134 mmol) and n-butylamine (20.0 mg, 0.237 mmol, 2 eq) in dichloromethane (2 ml), a solution of dicyclohexylcarbodiimide (28.2 mg, 0.137 mmol, 1 eq) in dichloromethane (2 ml) was added at 0° C., then stirred at room temperature for 18 h. Insoluble substance was separated by filtration, and the filtrate was concentrated. The residue was purified by silica gel column chromatography (eluent: chloroform/methanol=30/1) to give N-n-butyl-11-[1-(4-hydroxyphenyl)-1,7-dicarba-closo-dodecaboran-7-yl]-n-undecanamide (BE520) (20.4 mg, 31.9%).

$^1$H-NMR (CDCl$_3$) d0.92 (3 H, t, J=7.3 Hz), 1.05–1.42 (18 H, m), 1.48 (2 H, quint, J=7.6 Hz), 1.6–3.1 (10 H, br m), 1.95 (2 H, m), 2.16 (2 H, t, J=7.6 Hz), 3.25 (2 H, dt, J=5.9,7.0 Hz), 5.44 (1 H, br s), 6.30 (1 H, br), 6.71 (2 H, d, J=8.8 Hz), 7.26 (2 H, d, J=8.8 Hz)

HRMS Calcd for C$_{23}$H$_{45}$$^{10}$B$_2$$^{11}$B$_8$NO$_2$ 476.4453, Found 475.4460

To a solution of 11-[1-(4-hydroxyphenyl)-1,7-dicarba-closo-dodecaboran-7-yl]-n-undecanoic acid (50.6 mg, 0.120 mmol), N-methyl-n-butylamine (20.9 mg, 0.240 mmol, 2 eq), and N-hydroxysuccinimide (13.9 mg, 0.121 mmol, 1 eq) in DMF (1.5 ml), and a solution of dicyclohexyl carbodiimide (25.0 mg, 0.121 mmol, 1 eq) in DMF (1.5 ml) was added at 0° C., then stirred at room temperature for 48 h. DMF was removed under reduced pressure, and ethyl acetate was added to the residue. After the insoluble substance was removed by filtration, the filtrate was concentrated. The residue was purified by silica gel column chromatography (eluent: chloroform/methanol=30/1) to give N-n-butyl-N-methyl-11-[1-(4-hydroxyphenyl)-1,7-dicarba-closo-dodecaboran-7-yl]-n-undecanamide (BE521) (17.1 mg, 29.0%).

$^1$H-NMR (CDCl$_3$) d 0.91, 0.95 (3 H, t×2, J=7.6 Hz), 1.05–1.42 (18 H, m), 1.45–1.60 (2 H, m), 1.6–3.1 (10 H, br m), 1.95 (2 H, m), 2.29, 2.31(2 H, t×2, J=7.4 Hz), 2.92, 2.98(3 H, s×2), 3.26, 3.36 (2 H, t×2; J=7.6 Hz), 6.72 (2 H, d, J=8.8 Hz), 7.25 (2 H, d, J=8.8 Hz) (1:1 mixture of cis, trans conformations of amide)

HRMS Calcd for C$_{24}$H$_{47}$$^{10}$B$_2$$^{11}$B$_8$NO$_2$ 489.4610, Found 489.4613

A solution of 4-ethynylanisole (2.70 g, 20.4 mmol) and decaborane (14)(2.50 g, 20.5 mmol) in benzene (100 ml) and acetonitrile (10 ml) was refluxed for 17 h under argon atmosphere. After cooling to room temperature, the mixture was diluted with methanol, stirred for 1 h and concentrated. The residue was purified by silica gel column chromatography (eluent: ethyl acetate/n-hexane=1/15) to give 1-(4-methoxyphenyl)-1,2-dicarba-closo-dodecaborane (1.26 g, 24.6%).

Colorless prisms (hexane)

m.p.: 109–111° C.

$^1$H-NMR (CDCl$_3$) d1.6–3.4 (10 H, br m), 3.80 (3 H, s), 3.87 (1 H, br s), 6.82 (2 H, d, J=9.1 Hz), 7.42 (2 H, d, J=9.2 Hz)

HRMS Calcd for C$_9$H$_{18}$$^{10}$B$_2$$^{11}$B$_8$O 250.2361, Found 250.2358

To a suspension of sodium hydride (60%)(302 mg, 7.55 mmol, 1.5 eq, washed with n-hexane) in DMF (6 ml), 1-(4-methoxyphenyl)-1,2-dicarba-closo-dodecaborane (1.26 g, 5.03 mmol) in DMF (30 ml) was added. After stirring at room temperature for 5 min, DMF solution (6 ml) of 2-(11-bromo-n-undecanoyloxy) tetrahydro-2H-pyran (1.69 g, 5.03 mmol) was added, and stirred at room temperature for 2 h. The reaction mixture was poured into 2N hydrochloric acid under ice cooling, and extracted with ether. The organic layer was washed with saturated brine, dried over sodium sulfate and concentrated. The residue was purified by silica gel column chromatography (eluent: ethyl acetate/n-hexane=1/30) to give 1-(4-methoxyphenyl)-2-(11-tetrahydropyranyloxy-n-undecane-1-yl)-1,2-dicarba-closo-dodecaborane (1.27 g, 50.0%).

$^1$H-NMR (CDCl$_3$) d1.00–1.40 (16 H, m), 1.48–1.62 (6 H, m), 1.6–3.1 (10 H, br m), 1.68–1.77 (3 H, m), 1.83 (1 H, m), 3.37 (1 H, dt, J=7.0,9.6 Hz), 3.50 (1 H, m); 3.72 (1 H, dt, J=7.0,9.6 Hz), 3.83 (3 H, s), 3.87 (1 H, m), 4.57 (1 H, m), 6.86 (2 H, d, J=9.0 Hz), 7.52 (2 H, d, J=9.0 Hz)

The protecting tetrahydropyranyl group of 1-(4-methoxyphenyl)-2-(11-tetrahydropyranyloxy-n-undecane-1-yl)-1,2-dicarba-closo-dodecaborane was deprotected by a similar procedure that used for 1-(4-methoxyphenyl)-7-(11-hydroxy-n-undecane-1-yl)-1,7-dicarba-closo-dodecaborane to give 1-(4-methoxyphenyl)-2-(11-hydroxy-n-undecane-1-yl)-1,2-dicarba-closo-dodeca borane (92.1%).

$^1$H-NMR (CDCl$_3$) d1.10–1.42 (16 H, m), 1.20 (1 H, t, J=5.4 Hz), 1.50–1.60 (2 H, m), 1.6–3.1 (10 H, br m), 1.74 (2 H, m), 3.63 (2 H, td, J=5.3, 6.6 Hz), 3.83 (3 H, s), 6.87 (2 H, d, J=9.0 Hz), 7.52 (2 H, d, J=9.0 Hz)

HRMS Calcd for C$_{20}$H$_{40}$$^{10}$B$_2$$^{11}$B$_8$O$_2$ 420.4031, Found 420.4062

1-(4-Methoxyphenyl)-2-(11-hydroxy-n-undecane-1-yl)-1,2-dicarba-closo-dodecaborane was converted to 11-{1-(4-methoxyphenyl)-1,2-dicarba-closo-dodecaboran-2-yl}-n-undecanoic acid (13.5 mg, 70.0%) by a similar procedure that used for 11-{1-(4-methoxyphenyl)-1,7-dicarba-closo-dodecaboran-7-yl]-n-undecanoic acid.

$^1$H-NMR (CDCl$_3$) d1.00–1.40 (14 H, m), 1.6–3.1 (10 H, br m), 1.61 (2 H, quint, J=8.6 Hz), 1.74 (2 H, m), 2.34 (2 H, t, J=8.6 Hz), 3.83 (3 H, s), 6.86 (2 H, d, J=9.0 H, d, J=9.0 Hz)

11-{1-(4-Methoxyphenyl)-1,2-dicarba-closo-dodecaboran-2-yl}-n-undecanoic acid was converted to 11-{1-(4-hydroxyphenyl)-1,2-dicarba-closo-dodecaboran-2-yl}-n-undecanoic acid (74.0%) by a similar procedure that used for 11-{1-(4-methoxyphenyl)-1,7-dicarba-closo-dodecaboran-7-yl}-n-undecanoic acid.

$^1$H-NMR (CDCl$_3$) d1.00–1.40 (14 H, m), 1.5–3.2 (10 H, br m), 1.62 (2 H, quint, J=7.5 Hz), 1.76 (2 H, m), 2.37 (2 H, t, J=7.3 Hz), 6.81 (2 H, d, J=9.0 Hz), 7.48 (2 H, d, J=8.8 Hz)

HRMS Calcd for C$_{19}$H$_{36}$$^{10}$B$_2$$^{11}$B$_8$O$_3$ 420.3668, Found 420.3655

To a solution of 11-{1-(4-hydroxyphenyl)-1,2-dicarba-closo-dodecaboran-2-yl}-n-undecanoic acid (29.8 mg, 0.0709 mmol) and n-butylamine (10.4 mg, 0.142 mmol, 2 eq) in acetonitrile (1 ml), a solution of dicyclohexylcarbodiimide (16.1 mg, 0.0780 mmol, 1.1 eq) in acetonitrile (1 ml) was added at 0° C., and stirred at room temperature for 6 h. Acetonitrile was removed under reduced pressure. Ethyl acetate was added to the residue to remove the insoluble substance by filtration, and the filtrate was concentrated. The residue was purified by silica gel column chromatography (eluent: chloroform/methanol=30/1), and further purified by silica gel column chromatography (eluent: ethyl acetate/n-hexane=1/2) to give N-n-butyl-11-{1-(4-hydroxyphenyl)-1,2-dicarba-closo-dodecaboran-2-yl}-n-undecanamide (BE530) (12.8 mg, 38.0%)

$^1$H-NMR (CDCl$_3$) d 0.85–1.40 (18 H, m), 0.95 (3 H, t, J=7.3 Hz), 1.50–1.60 (2 H, m), 1.5–3.2 (10 H, br m), 1.80 (2 H, m), 2.22 (2 H, t, J=7.3 Hz), 3.31 (2 H, dt, J=5.8,7.1 Hz), 5.60 (1 H, br s), 6.86 (2 H, d, J=8.8 Hz), 7.44 (2 H, d, J=9.0 Hz), 9.50 (1 H, br s)

HRMS Calcd for $C_{23}H_{45}{}^{10}B_2{}^{11}B_8NO_2$ 475.4453, Found 475.4450

To a solution of 11-{1-(4-hydroxyphenyl)-1,2-dicarba-closo-dodecaboran-2-yl}-n-undecanoic acid (79.4 mg, 0.189 mmol) and N-methyl-n-butylamine (32.9 mg, 0.378 mmol, 2 eq) in acetonitrile (2 ml), and a solution of dicyclohexylcarbodiimide (43.0 mg, 0.208 mmol, 1.1 eq) in acetonitrile (2 ml) was added at 0° C., and stirred at room temperature for 20 h. Acetonitrile was removed under reduced pressure. Ethyl acetate was added to the residue to remove the insoluble substance by filtration, and the filtrate was concentrated. The residue was purified by silica gel column chromatography (eluent: chloroform/methanol=30/1), and further purified by preparative thin-layer chromatography (eluent: dichloromethane/n-hexane=30/1) to give N-n-butyl-N-methyl-11-{1-(4-hydroxyphenyl)-1,2-dicarba-closo-dodecaboran-2-yl}-n-undecanamide (BE531)(24.8 mg, 26.8%).

$^1$H-NMR (CDCl$_3$) d0.85–1.40 (18 H, m), 0.94, 0.97 (3 H, t×2, J=7.3 Hz), 1.50–1.65 (2 H, m), 1.5–3.2 (10 H, br m), 1.79 (2 H, m), 2.35, 2.36 (3 H, t×2, J=7.3 Hz), 2.98, 3.02 (3 H, s×2), 3.30, 3.42 (3 H, t×2, J=7.5 Hz), 6.87, 6.88 (2 H, d×2, J=8.9 Hz), 7.43 (2 H, d, J=8.1 Hz), 9.79, 9.82 (1 H, br s×2) (1 to1 cis, trans conformational mixture of amide)

HRMS Calcd for $C_{24}H_{47}{}^{10}B_2{}^{11}B_8NO_2$ 489.4610, Found 489.4607

Test Example

Anti-leukemia activity test and estrogen activity test were performed on nuclear receptor regulators having a dicarba-closo-dodecaborane structure of the present invention obtained in the examples.

(1) Anti-leukemia Activity

Inhibitory activity against proliferation of human promyelocytic leukemia cell strain HL-60 was evaluated an index of anti-leukemia activity. Subcultured HL-60 cells were seeded with the initial cell number of $8 \times 10^4$ cells/ml in the RPMI 1640 medium containing bovine fetal serum and an antibiotics. Each test compound was added at various concentrations and the mixture was cultured at 37° C. Four days later, cell number was counted. Anti-leukemia activity of each test compound was shown in the tables as percentage values of differentiated cells, which cells were not differentiated in the absence of the test drug, in the presence of 1 mM of the test compound based on morphological change observation and NBT reducing ability of the cells as indexes. Table 1 shows the results obtained by experiments wherein only the test compounds were added. BR401, BR403, and BR453 were found to have strong differentiation inducing activities and the activities were maintained at 0.01 μM concentration of the test compounds.

Table 2 shows the results of experiments with coexistence of the compound AM80 as a differentiation inducing agent (4-[(5,6,7,8-tetrahydro-5,5,8,8-tetramethyl-2-naphthalenyl)carbamoyl]benzoic acid). As a result, BR201 was found to have a strong anti-differentiation activity. Table 3 shows the results of experiments with coexistence of the compound HX630 (4-[2,3-(2,5-dimethyl-2,5-hexano)dibenzo-[b,f]-[1,4]thiazepin-11-yl]benzoic acid) which is inactive per se but enhances the action of differentiation inducing substances. As a result, BR110, BR251, and BR350 were found to have differentiation inducing activities.

TABLE 1

| Test Compound 1 μM | No coexisting compound (control: <10) |
|---|---|
| BR10 | 8 |
| BR20 | 12 |
| BR30 | 7 |
| BR110 | 12 |
| BR201 | 11 |
| BR251 | 8 |
| BR300 | 6 |
| BR350 | 11 |
| BR401 | 70 |
| BR403 | 82 |
| BR431 | 10 |
| BR453 | 80 |
| BR401* | 26 |
| BR403* | 84 |
| BR453* | 80 |

*Test Compound 0.01 μM

TABLE 2

| Test Compound | Coexisting compound Am80 $3.3 \times 10^{-10}$M (control: 55) |
|---|---|
| BR10 | 65 |
| BR20 | 70 |
| BR30 | 66 |
| BR110 | 60 |
| BR201 | 5 |
| BR251 | 55 |
| BR300 | 37 |
| BR350 | 60 |
| BR401 | 60 |
| BR431 | 55 |

TABLE 3

| Test Compound | Coexisting Compound HX630 $1 \times 10^{-7}$M (control: <10) |
|---|---|
| BR10 | 7 |
| BR20 | 10 |
| BR30 | 9 |
| BR110 | 48 |
| BR201 | 12 |
| BR251 | 77 |
| BR300 | 8 |
| BR350 | 48 |
| BR401 | 75 |
| BR431 | 12 |

Table 4 shows the concentrations of the test compounds as IC$_{50}$ values which inhibited 50% of differentiation inducing activity when the compound Am80 as a differentiation inducing agent coexisted at $1 \times 10^{-9}$ M. BR630 and BR635 were found to have remarkable anti-differentiation activities.

TABLE 4

| Test Compound | IC$_{50}$ (mM)<br>Coexisting compound: Am80 1 × 10$^{-9}$M |
|---|---|
| BR630 | 0.025 |
| BR635 | 0.028 |
| BR638 | 0.61 |
| BR10 | inactive |
| BR20 | inactive |
| BR30 | inactive |

(2) Estrogenic Activity

As estrogenic activity, estrogen receptor-dependent transcriptional activation abilities of the test compounds were determined by the r porter gene assay using luciferase gene. COS-1 cells were cultured using a DMEM medium containing an antibiotics and 5% bovine fetal serum in the wells of 24 well plates (cell density: 5 to 6×10$^4$/well) at 37° C. for one night under 5% carbon dioxide. On the next day, the medium was changed to DMEM medium not containing Phenol Red. Using gene introducing reagent Tfx-20 (Promega), reporter plasmid EREx3-pGL-TK, in which rat estrogen receptor expression plasmid pCI-rER α and an estrogen responsive sequence were placed upstream of the luciferase gene, and β-galactosidase expression plasmid pCMV β used as an internal standard were introduced into cells. The cells were cultured for 2 h, and the medium was changed to DMEM not containing Phenol Red but containing active charcoal-treated serum.

The culture was added with each test compound dissolved in ethanol at various concentrations (final ethanol concentration at 0.5%) and then cultivation was continued at 37° C. for one night under 5% carbon dioxide. On the next day, the cells were lysed and enzymatic activity of luciferase expressed was measured by using a chemiluminometer. The values were standardized based on galactocidase enzymatic activity, and then compared with the values obtained by experiments using no test compound and used as values of activity at various concentrations. Table 4 shows estrogenic activities. The estrogenic activities in the table are shown as concentrations for 50% activity (EC$_{50}$ values) which give 50% activities relative to luciferase activity regarded as 100 that is expressed by treatment with the control compound β-estradiol at 10 nM. Each compound tested in this experiment has a high estrogenic activity. In particular, BE100, BE120, BE121, and BE140 have much higher activity than that of β-estradiol used as the control.

TABLE 5

| Test Compound | EC$_{50}$ Value (nM) |
|---|---|
| BE100 | 0.7 |
| BE110 | 2.0 |
| BE120 | 0.05 |
| BE121 | 1.0 |
| BE130 | 10 |
| BE140 | 0.5 |
| BE160 | 1.0 |
| BE200 | 2.0 |
| BE260 | 1.0 |

Estrogenic activities, i.e., estrogen receptor-dependent transcriptional abilities of test compounds, were determined by the reporter gene assay using the luciferase gene in the same manner as those described above. In this experiment (Table 6), estrogenic activities at 0.1 nM, 1 nM, and 10 nM of the test compounds are shown as relative values in view of the luciferase activity regarded as 100 which is expressed at the same amounts of β-estradiol as a control, and intensities of activities were compared. Each compound tested in this experiment has high estrogenic activity. In particular, BE119, BE120, and BE320 have much higher activities than that of β-estradiol as the control.

TABLE 6

| Test Compound | Relative Activity (%) at the Same Amount of β-estradiol | | |
|---|---|---|---|
|  | 0.1 nM | 1 nM | 10 nM |
| BE100 | 51 | 63 | 82 |
| BE119 | 133 | 132 | 120 |
| BE120 | 212 | 163 | 126 |
| BE122 | 83 | 98 | 104 |
| BE123 | 29 | 56 | 79 |
| BE200 |  | 45 | 72 |
| BE219 |  | 40 | 71 |
| BE220 |  | 57 | 116 |
| BE222 |  | 38 | 85 |
| BE223 |  | 20 | 51 |
| BE300 |  | 20 | 59 |
| BE319 |  | 53 | 72 |
| BE320 | 116 | 127 | 127 |
| BE322 |  | 43 | 85 |
| BE323 |  | 12 | 31 |
| BE400 |  | 11 | 38 |
| BE419 |  | 14 | 38 |
| BE420 |  | 18 | 59 |
| BE422 |  | 11 | 24 |
| BE423 |  | <10 | 15 |

(3) Antiestrogenic Activity

As antiestrogenic activities, estrogen receptor-dependent transcriptional activation abilities of the test compounds were measured by the reporter gene assay using luciferase gene in the same manner as the estrogen activity measurement. In Table 7, antiestrogenic activities of test compounds are indicated as IC$_{50}$ values as 50% inhibitory concentrations relative to the luciferase activity regarded as 100 which is expressed by β-estradiol at 1 nM coexisting in the experimental system. Each compound tested in this experiment has antiestrogenic activity. In particular, BE362 has strong activity comparable to that of antiestrogenic drug tamoxifen used as a control.

TABLE 7

| Test Compound | IC$_{50}$ Value (nM)<br>Coexisting compound:<br>β-estradiol 1 × 10$^{-9}$M |
|---|---|
| BR162 | 10* |
| BR172 | 600 |
| BR262 | 200 |
| BR272 | 500 |
| BR362 | 30 |
| BR372 | 200 |

*BE162 was found to achieve incomplete inhibition even at 1 mM (a partial inhibitor)

Industrial Applicability

The compounds represented by the aforementioned formula (I) or physiologically acceptable salts thereof have physiological activities such as retinoid activities, and therefore, medicaments of the present invention comprising said substance as an active ingredients are useful for the treatment of leukemia and the like.

What is claimed is:

1. A medicament composition comprising as an active ingredient a compound or a physiologically acceptable salt thereof represented by the following general formula (I):

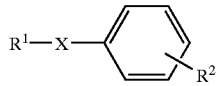
(I)

wherein $R^1$ represents a dicarba-closo-dodecaboran-yl group which may be substituted with a lower alkyl group; $R^2$ represents carboxyl group or a lower alkoxy carbonyl group; X represents a linking group selected from the group consisting of the groups represented by the following formulas:

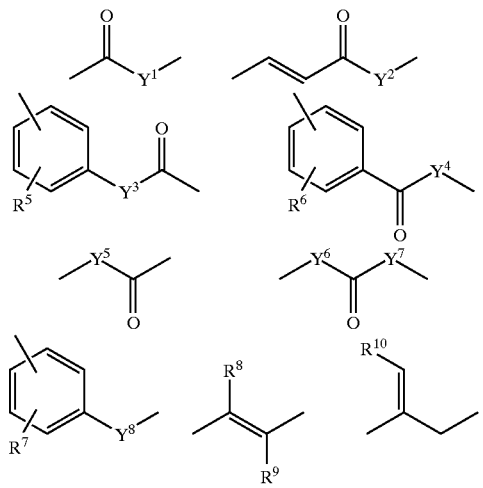

wherein, $Y^1$, $Y^2$, $Y^3$, $Y^4$, $Y^5$, $Y^6$, and $Y^7$ independently represent oxygen atom or —N($R^3$)— wherein $R^3$ represents hydrogen atom or a lower alkyl group; $Y^8$ represents oxygen atom, —N($R^4$)— wherein $R^4$ represents hydrogen atom or a lower alkyl group, —CO—, —CH$_2$—, or —C(=CH$_2$)—; $R^5$, $R^6$, and $R^7$ independently represents hydrogen atom or one or more substituents on the phenyl group; $R^8$ represents a lower alkyl group or an aryl group which may be substituted, $R^9$ represents a lower alkyl group, and $R^{10}$ represents an aryl group which may be substituted.

2. A compound or a salt thereof represented by the following general formula (I):

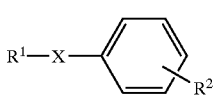
(I)

wherein $R^1$ represents a dicarba-closo-dodecaboran-yl group which may be substituted with a lower alkyl group; $R^2$ represents carboxyl group or a lower carbonyl group; X represents a linking group selected from the group consisting of the groups represented by the following formulas:

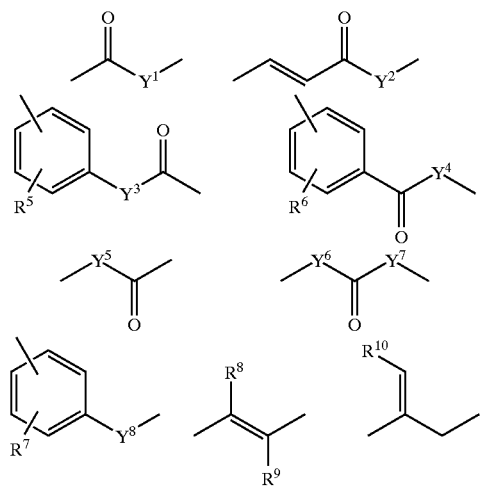

wherein, $Y^1$, $Y^2$, $Y^3$, $Y^4$, $Y^5$, $Y^6$, and $Y^7$ independently represents oxygen atom or —N($R^3$)— wherein $R^3$ represents hydrogen atom or a lower alkyl group; $Y^8$ represents oxygen atom, —N($R^4$)— wherein $R^4$ represents hydrogen atom or a lower alkyl group, —CO—, —CH$_2$—, or —C(=CH$_2$)—; $R^5$, $R^6$, and $R^7$ independently represents hydrogen atom or one or more substituents on the phenyl group, $R^8$ represents a lower alkyl group or an aryl group which may be substituted; $R^9$ represents a lower alkyl group; and $R^{10}$ represents an aryl group which may be substituted.

3. A method of binding a receptor and a ligand, comprising binding a nuclear receptor and a nuclear receptor ligand in the presence of a compound or a physiologically acceptable salt thereof represented by the general formula (I) as recited in claim 1.

* * * * *

UNITED STATES PATENT AND TRADEMARK OFFICE
CERTIFICATE OF CORRECTION

PATENT NO. : 6,838,574 B1
DATED : January 4, 3005
INVENTOR(S) : Y. Endo

It is certified that error appears in the above-identified patent and that said Letters Patent is hereby corrected as shown below:

Title page,
Item [54], Title, "DODECARBORANE" should be -- DODECABORANE --.

Column 6,
Line 47, "claim 1" should be -- claim 2 --.

Signed and Sealed this

Twenty-third Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,838,574 B1
DATED : January 4, 2005
INVENTOR(S) : Y. Endo

It is certified that error appears in the above-identified patent and that said Letters Patent is hereby corrected as shown below:

Title page,
Item [54], Title, "DODECARBORANE" should be -- DODECABORANE --.

Column 6,
Line 47, "claim 1" should be -- claim 2 --.

This certificate supersedes Certificate of Correction issued August 23, 2005.

Signed and Sealed this

Eighteenth Day of October, 2005

JON W. DUDAS
*Director of the United States Patent and Trademark Office*